US011100404B2

(12) United States Patent
Merriman et al.

(10) Patent No.: US 11,100,404 B2
(45) Date of Patent: *Aug. 24, 2021

(54) METHODS, APPARATUS AND SYSTEMS FOR AMPLIFICATION-FREE DNA DATA STORAGE

(71) Applicant: Roswell Biotechnologies, Inc., San Diego, CA (US)

(72) Inventors: Barry Merriman, San Diego, CA (US); Tim Geiser, San Diego, CA (US); Paul Mola, San Diego, CA (US); Gina Costa, San Diego, CA (US)

(73) Assignee: Roswell Biotechnologies, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/652,672

(22) PCT Filed: Oct. 10, 2018

(86) PCT No.: PCT/US2018/055264
§ 371 (c)(1),
(2) Date: Jun. 29, 2020

(87) PCT Pub. No.: WO2019/075100
PCT Pub. Date: Apr. 18, 2019

(65) Prior Publication Data
US 2020/0242482 A1 Jul. 30, 2020

Related U.S. Application Data

(60) Provisional application No. 62/570,458, filed on Oct. 10, 2017.

(51) Int. Cl.
*G06N 3/12* (2006.01)
*G16B 50/30* (2019.01)
*G16B 30/20* (2019.01)
*G16B 50/40* (2019.01)
*C12N 15/11* (2006.01)
*C12Q 1/6869* (2018.01)
*C12Q 1/6825* (2018.01)

(52) U.S. Cl.
CPC ............ *G06N 3/123* (2013.01); *C12N 15/11* (2013.01); *C12Q 1/6825* (2013.01); *C12Q 1/6869* (2013.01); *G16B 30/20* (2019.02); *G16B 50/30* (2019.02); *G16B 50/40* (2019.02)

(58) Field of Classification Search
None
See application file for complete search history.

(56) References Cited

U.S. PATENT DOCUMENTS

| 4,923,586 | A | 5/1990 | Katayama et al. |
| 5,082,627 | A | 1/1992 | Stanbro |
| 5,194,133 | A | 3/1993 | Clark et al. |
| 5,366,140 | A | 11/1994 | Koskenmaki et al. |
| 5,414,588 | A | 5/1995 | Barbee, Jr. |
| 5,486,449 | A | 1/1996 | Honso et al. |
| 5,532,128 | A | 7/1996 | Eggers et al. |
| 5,583,359 | A | 12/1996 | Ng et al. |
| 5,639,507 | A | 6/1997 | Galvagni et al. |
| 5,646,420 | A | 7/1997 | Yamashita |
| 5,767,687 | A | 6/1998 | Geist |
| 5,871,918 | A | 2/1999 | Thorp et al. |
| 5,881,184 | A | 3/1999 | Guidash |
| 5,965,452 | A | 10/1999 | Kovacs |
| 5,982,018 | A | 11/1999 | Wark |
| 6,051,380 | A | 4/2000 | Sosnowski et al. |
| 6,060,023 | A | 5/2000 | Maracas |
| 6,094,335 | A | 7/2000 | Early |
| 6,110,354 | A | 8/2000 | Saban |
| 6,123,819 | A | 9/2000 | Peeters |
| 6,144,023 | A | 11/2000 | Clerc |
| 6,238,927 | B1 | 5/2001 | Abrams et al. |
| 6,440,662 | B1 | 8/2002 | Gerwen et al. |

(Continued)

FOREIGN PATENT DOCUMENTS

| CN | 1795376 | 6/2006 |
| CN | 101231287 | 7/2008 |

(Continued)

OTHER PUBLICATIONS

Church et al. Next-Generation Digital Information Storage in DNA Science vol. 337, p. 1628 and supplementary information (Year: 2012).*
USPTO; Notice of Allowance dated May 11, 2020 in U.S. Appl. No. 16/073,706.
USPTO; Notice of Allowance dated Jun. 1, 2020 in U.S. Appl. No. 16/076,673.
USPTO; Non-Final Office Action dated Jun. 2, 2020 in U.S. Appl. No. 16/684,338.
USPTO; Non-Final Office Action dated Jun. 15, 2020 in U.S. Appl. No. 16/878,484.
USPTO; Non-Final Office Action dated Jun. 30, 2020 in U.S. Appl. No. 16/479,257.

(Continued)

*Primary Examiner* — John S Brusca
(74) *Attorney, Agent, or Firm* — Spectrum IP Law Group LLC

(57) ABSTRACT

In various embodiments, amplification-free DNA information methods, apparatus and systems are disclosed. A method of amplification-free information storage and retrieval comprises encoding digital data such as binary into nucleotide sequence motifs using an encoding scheme, and synthesizing replicate DNA molecules using an amplification-free DNA writing process. The amplification-free process of decoding the information stored in the DNA comprises exposing at least one of the replicate DNA molecules to a molecular electronics sensor that generates distinguishable signals in a measured electrical parameter of the sensor, wherein the distinguishable signals correspond to the sequence motifs, providing decoding back to the digital data.

20 Claims, 26 Drawing Sheets

Specification includes a Sequence Listing.

(56) References Cited

U.S. PATENT DOCUMENTS

| | | |
|---|---|---|
| 6,464,889 B1 | 10/2002 | Lee et al. |
| 6,506,564 B1 | 1/2003 | Mirkin et al. |
| 6,537,747 B1 | 3/2003 | Mills, Jr. et al. |
| 6,670,131 B2 | 12/2003 | Hashimoto |
| 6,673,533 B1 | 1/2004 | Wohlstadter et al. |
| 6,716,620 B2 | 4/2004 | Bashir et al. |
| 6,749,731 B2 | 6/2004 | Kobori |
| 6,762,050 B2 | 7/2004 | Fukushima et al. |
| 6,764,745 B1 | 7/2004 | Karasawa et al. |
| 6,790,341 B1 | 9/2004 | Saban |
| 6,824,974 B2 | 11/2004 | Pisharody et al. |
| 6,861,224 B2 | 3/2005 | Fujita et al. |
| 6,916,614 B1 | 7/2005 | Takenaka et al. |
| 6,958,216 B2 | 10/2005 | Kelley |
| 7,015,046 B2 | 3/2006 | Wohlstadter et al. |
| 7,075,428 B1 | 7/2006 | Oleynik |
| 7,169,272 B2 | 1/2007 | Fritsch et al. |
| 7,183,055 B2 | 2/2007 | Van Der Weide |
| 7,189,435 B2 | 3/2007 | Tuominen et al. |
| 7,202,480 B2 | 4/2007 | Yokoi et al. |
| 7,208,077 B1 | 4/2007 | Albers et al. |
| 7,276,206 B2 | 10/2007 | Augustine et al. |
| 7,399,585 B2 | 7/2008 | Gau |
| 7,432,120 B2 | 10/2008 | Mascolo et al. |
| 7,470,533 B2 | 12/2008 | Xu et al. |
| 7,507,320 B2 | 3/2009 | Hwang et al. |
| 7,531,120 B2 | 5/2009 | Van Rijn et al. |
| 7,579,823 B1 | 8/2009 | Ayliffe |
| 7,691,433 B2 | 4/2010 | Kronholz et al. |
| 7,785,785 B2 | 8/2010 | Pourmand et al. |
| 7,834,344 B2 | 11/2010 | Mascolo et al. |
| 7,851,045 B2 | 12/2010 | Gandon et al. |
| 7,886,601 B2 | 2/2011 | Merassi et al. |
| 7,901,629 B2 | 3/2011 | Calatzis et al. |
| 7,943,394 B2 | 5/2011 | Flandre et al. |
| 8,241,508 B2 | 8/2012 | D'Urso |
| 8,313,633 B2 | 11/2012 | Li et al. |
| 8,351,181 B1 | 1/2013 | Ahn |
| 8,591,816 B2 | 11/2013 | Calatzis et al. |
| 8,652,768 B1 | 2/2014 | Huber et al. |
| 8,753,893 B2 | 6/2014 | Liu et al. |
| 8,927,464 B2 | 1/2015 | Aizenberg et al. |
| 8,940,663 B2 | 1/2015 | Iqbal et al. |
| 9,070,733 B2 | 6/2015 | Rajagopal et al. |
| 9,108,880 B2 | 8/2015 | Jin et al. |
| 9,139,614 B2 | 9/2015 | Medintz |
| 9,306,164 B1 | 4/2016 | Chang et al. |
| 9,829,456 B1 | 11/2017 | Merriman et al. |
| 9,956,743 B2 | 5/2018 | Jin et al. |
| 10,036,064 B2 | 7/2018 | Merriman et al. |
| 10,125,420 B2 | 11/2018 | Jin et al. |
| 10,151,722 B2 | 12/2018 | Jin et al. |
| 10,508,296 B2 | 12/2019 | Merriman et al. |
| 10,526,696 B2 | 1/2020 | Jin et al. |
| 10,584,410 B2 | 3/2020 | Jin et al. |
| 10,597,767 B2 | 3/2020 | Merriman et al. |
| 10,712,334 B2 | 7/2020 | Choi et al. |
| 2002/0022223 A1 | 2/2002 | Connolly |
| 2002/0090649 A1 | 7/2002 | Chan et al. |
| 2002/0137083 A1 | 9/2002 | Kobori et al. |
| 2002/0138049 A1 | 9/2002 | Allen et al. |
| 2002/0142150 A1 | 10/2002 | Baumann et al. |
| 2002/0142477 A1 | 10/2002 | Lewis et al. |
| 2002/0172963 A1 | 11/2002 | Kelley et al. |
| 2002/0184939 A1 | 12/2002 | Yadav |
| 2003/0025133 A1 | 2/2003 | Brousseau |
| 2003/0040000 A1 | 2/2003 | Connolly et al. |
| 2003/0040173 A1 | 2/2003 | Fonash |
| 2003/0064390 A1 | 4/2003 | Schülein et al. |
| 2003/0087296 A1 | 5/2003 | Fujita et al. |
| 2003/0109031 A1 | 6/2003 | Chafin et al. |
| 2003/0141189 A1 | 7/2003 | Lee et al. |
| 2003/0141276 A1 | 7/2003 | Lee et al. |
| 2003/0186263 A1 | 10/2003 | Frey et al. |
| 2003/0224387 A1 | 12/2003 | Kunwar et al. |
| 2004/0014106 A1 | 1/2004 | Patno et al. |
| 2004/0023253 A1 | 2/2004 | Kunwar et al. |
| 2004/0038090 A1 | 2/2004 | Faris |
| 2004/0048241 A1 | 3/2004 | Freeman et al. |
| 2004/0063100 A1 | 4/2004 | Wang |
| 2004/0086929 A1 | 5/2004 | Weide et al. |
| 2004/0096866 A1 | 5/2004 | Hoffman et al. |
| 2004/0012161 A1 | 6/2004 | Chiu |
| 2004/0146863 A1 | 7/2004 | Pisharody et al. |
| 2004/0209355 A1 | 10/2004 | Edman et al. |
| 2004/0209435 A1 | 10/2004 | Patridge et al. |
| 2004/0229247 A1 | 11/2004 | DeBoer et al. |
| 2004/0235016 A1 | 11/2004 | Hamers |
| 2004/0248282 A1 | 12/2004 | Sobha |
| 2005/0029227 A1 | 2/2005 | Chapman |
| 2005/0067086 A1 | 3/2005 | Ito et al. |
| 2005/0074911 A1 | 4/2005 | Kornilovich et al. |
| 2005/0151541 A1 | 7/2005 | Brinz et al. |
| 2005/0156157 A1 | 7/2005 | Parsons et al. |
| 2005/0164371 A1 | 7/2005 | Arinaga |
| 2005/0172199 A1 | 8/2005 | Miller et al. |
| 2005/0181195 A1 | 8/2005 | Dubrow |
| 2005/0221473 A1 | 10/2005 | Dubin et al. |
| 2005/0227373 A1 | 10/2005 | Flandre et al. |
| 2005/0247573 A1 | 11/2005 | Nakamura et al. |
| 2005/0285275 A1 | 12/2005 | Son |
| 2005/0287548 A1 | 12/2005 | Bao et al. |
| 2005/0287589 A1 | 12/2005 | Connolly |
| 2006/0003482 A1 | 1/2006 | Chinthakindi et al. |
| 2006/0019273 A1 | 1/2006 | Connolly et al. |
| 2006/0024504 A1 | 2/2006 | Nelson et al. |
| 2006/0024508 A1 | 2/2006 | D'Urso et al. |
| 2006/0029808 A1 | 2/2006 | Zhai et al. |
| 2006/0051919 A1 | 3/2006 | Mascolo et al. |
| 2006/0051946 A1 | 3/2006 | Mascolo et al. |
| 2006/0105449 A1 | 5/2006 | Larmer et al. |
| 2006/0105467 A1 | 5/2006 | Niksa et al. |
| 2006/0128239 A1 | 5/2006 | Nun et al. |
| 2006/0147983 A1 | 7/2006 | O'uchi |
| 2006/0154489 A1 | 7/2006 | Tornow |
| 2006/0275853 A1 | 12/2006 | Matthew et al. |
| 2007/0026193 A1 | 2/2007 | Luzinov et al. |
| 2007/0048748 A1 | 3/2007 | Williams et al. |
| 2007/0140902 A1 | 6/2007 | Calatzis et al. |
| 2007/0148815 A1 | 6/2007 | Chao et al. |
| 2007/0186628 A1 | 8/2007 | Curry et al. |
| 2007/0184247 A1 | 9/2007 | Simpson et al. |
| 2007/0207487 A1 | 9/2007 | Emig et al. |
| 2007/0231542 A1 | 10/2007 | Deng |
| 2008/0012007 A1 | 1/2008 | Li et al. |
| 2008/0098815 A1 | 5/2008 | Merassi et al. |
| 2008/0149479 A1 | 6/2008 | Olofsson et al. |
| 2008/0199657 A1 | 8/2008 | Capron et al. |
| 2008/0199659 A1 | 8/2008 | Zhao |
| 2009/0011222 A1 | 1/2009 | Xiu et al. |
| 2009/0017571 A1 | 1/2009 | Nuckolls |
| 2009/0020428 A1 | 1/2009 | Levitan |
| 2009/0027036 A1 | 1/2009 | Nuckolls et al. |
| 2009/0062684 A1 | 3/2009 | Gregersen et al. |
| 2009/0152109 A1 | 6/2009 | Whitehead et al. |
| 2009/0162927 A1 | 6/2009 | Naaman et al. |
| 2009/0170716 A1 | 7/2009 | Su et al. |
| 2009/0178935 A1 | 7/2009 | Reymond et al. |
| 2009/0295372 A1 | 12/2009 | Krstic et al. |
| 2009/0297913 A1 | 12/2009 | Zhang et al. |
| 2009/0306578 A1 | 12/2009 | Sivan et al. |
| 2009/0324308 A1 | 12/2009 | Law et al. |
| 2010/0038342 A1 | 2/2010 | Lim et al. |
| 2010/0044212 A1 | 2/2010 | Kim et al. |
| 2010/0055397 A1 | 3/2010 | Kurihara et al. |
| 2010/0132771 A1 | 6/2010 | Lu |
| 2010/0142259 A1 | 6/2010 | Drndic et al. |
| 2010/0149530 A1 | 6/2010 | Tomaru |
| 2010/0167938 A1 | 7/2010 | Su et al. |
| 2010/0184062 A1 | 7/2010 | Steinmueller-Nethl et al. |
| 2010/0188109 A1 | 7/2010 | Edel et al. |
| 2010/0194409 A1 | 8/2010 | Gao et al. |
| 2010/0201381 A1 | 8/2010 | Iqbal et al. |
| 2010/0206367 A1 | 8/2010 | Jeong et al. |

(56) References Cited

U.S. PATENT DOCUMENTS

| | | |
|---|---|---|
| 2010/0227416 A1 | 9/2010 | Koh et al. |
| 2010/0280397 A1 | 11/2010 | Feldman et al. |
| 2010/0285275 A1 | 11/2010 | Baca et al. |
| 2010/0285601 A1 | 11/2010 | Kong et al. |
| 2010/0288543 A1 | 11/2010 | Hung et al. |
| 2010/0300899 A1 | 12/2010 | Levine et al. |
| 2011/0056845 A1 | 3/2011 | Stellacci |
| 2011/0065588 A1 | 3/2011 | Su et al. |
| 2011/0076783 A1 | 3/2011 | Liu et al. |
| 2011/0091787 A1 | 4/2011 | McGrath et al. |
| 2011/0160077 A1 | 6/2011 | Chaisson et al. |
| 2011/0166034 A1 | 7/2011 | Kwong et al. |
| 2011/0217763 A1 | 9/2011 | Rasooly et al. |
| 2011/0227558 A1 | 9/2011 | Mannion et al. |
| 2011/0229667 A1 | 9/2011 | Jin et al. |
| 2011/0233075 A1 | 9/2011 | Soleymani et al. |
| 2011/0248315 A1 | 10/2011 | Nam et al. |
| 2011/0287956 A1 | 11/2011 | Iqbal et al. |
| 2011/0291673 A1 | 12/2011 | Shibata et al. |
| 2011/0311853 A1 | 12/2011 | Fratti |
| 2011/0312529 A1 | 12/2011 | He et al. |
| 2012/0060905 A1 | 3/2012 | Fogel et al. |
| 2012/0122715 A1 | 5/2012 | Gao et al. |
| 2012/0220046 A1 | 8/2012 | Chao |
| 2012/0258870 A1 | 10/2012 | Schwartz et al. |
| 2012/0286332 A1 | 11/2012 | Rothberg et al. |
| 2012/0309106 A1 | 12/2012 | Eichen et al. |
| 2013/0049158 A1 | 2/2013 | Hong et al. |
| 2013/0071289 A1 | 3/2013 | Knoll |
| 2013/0108956 A1 | 5/2013 | Lu et al. |
| 2013/0109577 A1 | 5/2013 | Korlach et al. |
| 2013/0162276 A1 | 6/2013 | Lee et al. |
| 2013/0183492 A1 | 7/2013 | Lee et al. |
| 2013/0214875 A1 | 8/2013 | Duncan et al. |
| 2013/0239349 A1 | 9/2013 | Knights et al. |
| 2013/0245416 A1 | 9/2013 | Yarmush et al. |
| 2013/0273340 A1 | 10/2013 | Neretina et al. |
| 2013/0281325 A1 | 10/2013 | Elibol et al. |
| 2013/0331299 A1 | 12/2013 | Reda et al. |
| 2014/0001055 A1 | 1/2014 | Elibol et al. |
| 2014/0011013 A1 | 1/2014 | Jin |
| 2014/0018262 A1 | 1/2014 | Reda et al. |
| 2014/0048776 A1 | 2/2014 | Huang et al. |
| 2014/0054788 A1 | 2/2014 | Majima et al. |
| 2014/0057283 A1 | 2/2014 | Wang et al. |
| 2014/0061049 A1 | 3/2014 | Lo et al. |
| 2014/0079592 A1 | 3/2014 | Chang et al. |
| 2014/0027775 A1 | 6/2014 | Quick et al. |
| 2014/0170567 A1 | 6/2014 | Sakamoto et al. |
| 2014/0174927 A1 | 6/2014 | Bashir et al. |
| 2014/0197459 A1 | 7/2014 | Kis et al. |
| 2014/0218637 A1 | 8/2014 | Gao et al. |
| 2014/0235493 A1 | 8/2014 | Zang et al. |
| 2014/0253827 A1 | 9/2014 | Gao et al. |
| 2014/0284667 A1 | 9/2014 | Basker et al. |
| 2014/0320849 A1 | 10/2014 | Chou et al. |
| 2014/0367749 A1 | 12/2014 | Bai et al. |
| 2014/0377900 A1 | 12/2014 | Yann et al. |
| 2015/0005188 A1 | 1/2015 | Levner et al. |
| 2015/0017655 A1 | 1/2015 | Huang et al. |
| 2015/0049332 A1 | 2/2015 | Sun et al. |
| 2015/0057182 A1 | 2/2015 | Merriman et al. |
| 2015/0065353 A1 | 3/2015 | Turner et al. |
| 2015/0068892 A1 | 3/2015 | Ueno et al. |
| 2015/0077183 A1 | 3/2015 | Ciubotaru |
| 2015/0148264 A1 | 5/2015 | Esfandyarpour et al. |
| 2015/0177150 A1 | 6/2015 | Rothberg et al. |
| 2015/0191709 A1 | 7/2015 | Heron et al. |
| 2015/0263203 A1 | 9/2015 | Lewis et al. |
| 2015/0293025 A1 | 10/2015 | Ninomiya et al. |
| 2015/0294875 A1 | 10/2015 | Khondaker et al. |
| 2015/0344945 A1 | 12/2015 | Mandell et al. |
| 2016/0017416 A1 | 1/2016 | Boyanov et al. |
| 2016/0045378 A1 | 2/2016 | Geloen |
| 2016/0155971 A1 | 6/2016 | Strachan et al. |
| 2016/0187282 A1 | 6/2016 | Gardner et al. |
| 2016/0265047 A1 | 9/2016 | van Rooyen et al. |
| 2016/0284811 A1 | 9/2016 | Yu et al. |
| 2016/0290957 A1 | 10/2016 | Ram |
| 2016/0319342 A1 | 11/2016 | Kawai et al. |
| 2016/0377564 A1 | 12/2016 | Carmignani et al. |
| 2017/0023512 A1 | 1/2017 | Cummins et al. |
| 2017/0037462 A1 | 2/2017 | Turner et al. |
| 2017/0038333 A1 | 2/2017 | Turner et al. |
| 2017/0043355 A1 | 2/2017 | Fischer |
| 2017/0044605 A1 | 2/2017 | Merriman |
| 2017/0131237 A1 | 5/2017 | Ikeda |
| 2017/0184542 A1 | 6/2017 | Chatelier et al. |
| 2017/0234825 A1 | 8/2017 | Elibol et al. |
| 2017/0240962 A1 | 8/2017 | Merriman |
| 2017/0288017 A1 | 10/2017 | Majima et al. |
| 2017/0332918 A1 | 11/2017 | Keane |
| 2018/0014786 A1 | 1/2018 | Keane |
| 2018/0031508 A1 | 2/2018 | Jin |
| 2018/0031509 A1 | 2/2018 | Jin |
| 2018/0045665 A1 | 2/2018 | Jin |
| 2018/0259474 A1 | 9/2018 | Jin |
| 2018/0297321 A1 | 10/2018 | Jin et al. |
| 2018/0305727 A1 | 10/2018 | Merriman |
| 2018/0340220 A1 | 11/2018 | Merriman |
| 2019/0004003 A1 | 1/2019 | Merriman |
| 2019/0033244 A1 | 1/2019 | Jin |
| 2019/0039065 A1 | 2/2019 | Choi |
| 2019/0041355 A1 | 2/2019 | Merriman |
| 2019/0041378 A1 | 2/2019 | Choi |
| 2019/0094175 A1 | 3/2019 | Merriman |
| 2019/0194801 A1 | 6/2019 | Jin et al. |
| 2019/0355442 A1 | 11/2019 | Merriman et al. |
| 2019/0376925 A1 | 12/2019 | Choi et al. |
| 2019/0383770 A1 | 12/2019 | Choi et al. |
| 2020/0157595 A1 | 5/2020 | Merriman et al. |
| 2020/0217813 A1 | 7/2020 | Merriman et al. |
| 2020/0277645 A1 | 9/2020 | Merriman et al. |
| 2020/0385850 A1 | 12/2020 | Merriman et al. |
| 2020/0385855 A1 | 12/2020 | Jin et al. |
| 2020/0393440 A1 | 12/2020 | Jin et al. |

FOREIGN PATENT DOCUMENTS

| | | |
|---|---|---|
| CN | 102706940 | 10/2012 |
| CN | 104685066 | 6/2015 |
| CN | 104703700 | 6/2015 |
| CN | 108027335 | 5/2018 |
| DE | 102012008375 | 10/2012 |
| DE | 102013012145 | 1/2015 |
| EP | 2053383 | 4/2009 |
| EP | 3403079 | 11/2018 |
| EP | 3408219 | 12/2018 |
| EP | 3408220 | 12/2018 |
| EP | 3414784 | 12/2018 |
| EP | 3420580 | 1/2019 |
| GB | 2485559 | 5/2012 |
| JP | 0233981 | 7/1990 |
| JP | 2008-258594 | 10/2008 |
| JP | 2018-522236 | 8/2018 |
| KR | 20070059880 | 6/2007 |
| KR | 20110104245 | 9/2011 |
| WO | 2001044501 | 6/2001 |
| WO | 2002049980 | 6/2002 |
| WO | 2002074985 | 9/2002 |
| WO | 2003042396 | 5/2003 |
| WO | 2004096986 | 11/2004 |
| WO | 2004099307 | 11/2004 |
| WO | 2005108612 | 11/2005 |
| WO | 2007054649 | 5/2007 |
| WO | 2007102960 | 9/2007 |
| WO | 2007126432 | 11/2007 |
| WO | 2007128965 | 11/2007 |
| WO | 2009003208 | 1/2009 |
| WO | 2009035647 | 3/2009 |
| WO | 2010022107 | 2/2010 |
| WO | 2012083249 | 6/2012 |
| WO | 2012087352 | 6/2012 |
| WO | 2012152056 | 11/2012 |

(56) References Cited

FOREIGN PATENT DOCUMENTS

| WO | 2013096851 | 6/2013 |
|---|---|---|
| WO | 2014182630 | 7/2014 |
| WO | 2015167019 | 11/2015 |
| WO | 2015176990 | 11/2015 |
| WO | 2015188197 | 12/2015 |
| WO | 2016016635 | 2/2016 |
| WO | 2016100635 | 6/2016 |
| WO | 2016100637 | 6/2016 |
| WO | 2016196755 | 12/2016 |
| WO | 2016210386 | 12/2016 |
| WO | 2017027518 | 2/2017 |
| WO | 2017041056 | 3/2017 |
| WO | 2017042038 | 3/2017 |
| WO | 2017061129 | 4/2017 |
| WO | 2017123416 | 7/2017 |
| WO | 2017132567 | 8/2017 |
| WO | 2017132586 | 8/2017 |
| WO | 2017139493 | 8/2017 |
| WO | 2017147187 | 8/2017 |
| WO | 2017151680 | 9/2017 |
| WO | 2017184677 | 10/2017 |
| WO | 2018022799 | 2/2018 |
| WO | 2018026855 | 2/2018 |
| WO | 2018098286 | 5/2018 |
| WO | 2018132457 | 7/2018 |
| WO | 2018136148 | 7/2018 |
| WO | 2018200687 | 11/2018 |
| WO | 2018208505 | 11/2018 |
| WO | 2003091458 | 1/2019 |

OTHER PUBLICATIONS

USPTO; Non-Final Office Action dated Jun. 30, 2020 in U.S. Appl. No. 16/477,106.
EP; European Search Report dated Jun. 18, 2020 in Application No. 16815467.2.
CN; Office Action dated Jun. 5, 2020 in Chinese Patent Application No. 2017800204782.
EP; European Search Report dated Jun. 26, 2020 in Application No. 17874229.2.
Li et al., "Graphene Channel Liquid Container Field Effect Transistor as pH Sensor," Hindawi Publishing Corp., Journal of Nanomaterials 2014.
USPTO; Requirement for Restriction dated Nov. 2, 2011 in U.S. Appl. No. 12/667,583.
USPTO; Non-Final Office Action dated Sep. 28, 2018 in U.S. Appl. No. 12/667,583.
USPTO; Final Office Action dated Feb. 19, 2019 in U.S. Appl. No. 12/667,583.
USPTO; Non-Final Office Action dated Aug. 19, 2019 in U.S. Appl. No. 12/667,583.
USPTO; Requirement for Restriction dated Dec. 1, 2016 in U.S. Appl. No. 13/996,477.
USPTO; Non-Final Office Action dated May 5, 2017 in U.S. Appl. No. 13/996,477.
USPTO; Final Office Action dated Oct. 4, 2017 in U.S. Appl. No. 13/996,477.
USPTO; Notice of Allowance dated Jan. 3, 2018 in U.S. Appl. No. 13/996,477.
USPTO; Final Office Action date Dec. 30, 2016 in U.S. Appl. No. 15/050,270.
USPTO; Advisory Action dated Mar. 14, 2017 in U.S. Appl. No. 15/050,270.
USPTO; Non-Final Office Action dated Sep. 29, 2017 in U.S. Appl. No. 15/050,270.
USPTO; Final Office Action dated Jul. 10, 2018 in U.S. Appl. No. 15/050,270.
USPTO; Advisory Action dated Sep. 26, 2018 in U.S. Appl. No. 15/050,270.
USPTO; Non-Final Office Action dated Feb. 26, 2019 in U.S. Appl. No. 15/050,270.
USPTO; Final Office Action dated Jul. 10, 2019 in U.S. Appl. No. 15/050,270.
USPTO; Notice of Allowance dated Jan. 6, 2020 in U.S. Appl. No. 15/050,270.
USPTO; Non-Final Office Action dated Oct. 19, 2016 in U.S. Appl. No. 15/220,307.
USPTO; Notice of Allowance dated Jul. 28, 2017 in U.S. Appl. No. 15/220,307.
USPTO; Requirement for Restriction dated Jan. 17, 2017 in U.S. Appl. No. 15/336,557.
USPTO; Non-Final Office Action dated May 16, 2017 in U.S. Appl. No. 15/336,557.
USPTO; Final Office Action dated Mar. 8, 2018 in U.S. Appl. No. 15/336,557.
USPTO; Notice of Allowance dated May 25, 2018 in U.S. Appl. No. 15/336,557.
USPTO; Non-Final Office Action dated Feb. 9, 2018 in U.S. Appl. No. 15/728,400.
USPTO; Final Office Action dated Jul. 10, 2018 in U.S. Appl. No. 15/728,400.
USPTO; Advisory Action dated Oct. 12, 2018 in U.S. Appl. No. 15/728,400.
USPTO; Advisory Action dated Nov. 14, 2018 in U.S. Appl. No. 15/728,400.
USPTO; Notice of Allowance dated Dec. 6, 2018 in U.S. Appl. No. 15/728,400.
USPTO; Non-Final Office Action dated Feb. 23, 2018 in U.S. Appl. No. 15/728,412.
USPTO; Notice of Allowance dated Sep. 12, 2018 in U.S. Appl. No. 15/728,412.
USPTO; Final Office Action dated Jun. 13, 2018 in U.S. Appl. No. 15/728,412.
USPTO; Non-Final Office Action dated Feb. 23, 2018 in U.S. Appl. No. 15/796,080.
USPTO; Final Office Action dated Jun. 14, 2018 in U.S. Appl. No. 15/796,080.
USPTO; Advisory Action dated Sep. 4, 2018 in U.S. Appl. No. 15/796,080.
USPTO; Notice of Allowance dated Oct. 11, 2018 in U.S. Appl. No. 15/796,080.
USPTO; Non-Final Office Action dated Mar. 7, 2019 in U.S. Appl. No. 15/944,356.
USPTO; Non-Final Office Action dated Sep. 4, 2018 in U.S. Appl. No. 15/979,135.
USPTO; Non-Final Office Action dated Nov. 30, 2018 in U.S. Appl. No. 15/979,135.
USPTO; Final Office Action dated Mar. 1, 2019 in U.S. Appl. No. 15/979,135.
USPTO; Advisory Action dated May 22, 2019 in U.S. Appl. No. 15/979,135.
USPTO; Non-Final Office Action dated Jun. 25, 2019 in U.S. Appl. No. 15/979,135.
USPTO; Notice of Allowance dated Dec. 11, 2019 in U.S. Appl. No. 15/979,135.
USPTO; Non-Final Office Action dated Aug. 22, 2019 in the U.S. Appl. No. 16/011,065.
USPTO; Final Office Action dated Mar. 6, 2020 in U.S. Appl. No. 16/011,065.
USPTO; Requirement for Restriction dated Oct. 15, 2018 in U.S. Appl. No. 16/015,028.
USPTO; Non-Final Office Action dated Dec. 26, 2018 in U.S. Appl. No. 16/015,028.
USPTO; Final Office Action dated Apr. 15, 2019 in U.S. Appl. No. 16/015,028.
USPTO; Non-Final Office Action dated Jul. 30, 2019 in the U.S. Appl. No. 16/015,028.
USPTO; Notice of Allowance dated Nov. 8, 2019 in U.S. Appl. No. 16/015,028.
USPTO; Requirement for Restriction dated Dec. 17, 2018 in U.S. Appl. No. 16/015,049.
USPTO; Non-Final Office Action dated Mar. 6, 2019 in U.S. Appl. No. 16/015,049.

(56) References Cited

OTHER PUBLICATIONS

USPTO; Final Office Action dated Jun. 19, 2019 in U.S. Appl. No. 16/015,049.
USPTO; Non-Final Office Action dated Nov. 5, 2019 in U.S. Appl. No. 16/015,049.
USPTO; Notice of Allowance dated Feb. 20, 2020 in U.S. Appl. No. 16/015,049.
USPTO; Non-Final Office Action dated Apr. 13, 2020 in U.S. Appl. No. 16/070,133.
USPTO; Restriction Requirement dated Sep. 19, 2019 in U.S. Appl. No. 16/073,706.
USPTO; Non-Final Office Action dated Oct. 24, 2019 in U.S. Appl. No. 16/073,706.
USPTO; Non-Final Office Action dated Jan. 10, 2020 in U.S. Appl. No. 16/076,673.
USPTO; Non-Final Office Action dated Feb. 1, 2019 in U.S. Appl. No. 16/152,190.
USPTO; Notice of Allowance dated May 30, 2019, in U.S. Appl. No. 16/152,190.
USPTO; Restriction Requirement dated May 29, 2019 in U.S. Appl. No. 16/250,929.
USPTO; Notice of Allowance dated Oct. 23, 2019 in U.S. Appl. No. 16/250,929.
USPTO; Restriction Requirement dated Apr. 8, 2020 in U.S. Appl. No. 16/479,257.
PCT; International Search Report and Written Opinion dated Nov. 29, 2012 in Application No. PCT/US2011/001995.
PCT; International Search Report and Written Opinion dated Apr. 13, 2018 in Application No. PCT/US2018/013140.
PCT; International Search Report and Written Opinion dated Jan. 27, 2017 in Application No. PCT/US2017/015437.
PCT; International Search Report and Written Opinion dated Jan. 27, 2017 in Application No. PCT/US2017/015465.
PCT; International Search Report and Written Opinion dated Jul. 26, 2017 in Application No. PCT/US2017/017231.
PCT; International Search Report and Written Opinion dated May 25, 2017 in Application No. PCT/US2017/018950.
PCT; International Search Report and Written Opinion dated Jul. 20, 2018 in Application No. PCT/US2018/029382.
PCT; International Search Report and Written Opinion dated Jul. 20 ,2018 in Application No. PCT/US2018/029393.
PCT; International Search Report and Written Opinion dated Sep. 27, 2016 in Application No. PCT/US2016/039446.
PCT; International Search Report and Written Opinion dated Nov. 22, 2017 in Application No. PCT/US2017/044023.
PCT; International Search Report and Written Opinion dated Dec. 26, 2017 in Application No. PCT/US2017/044965.
PCT; International Search Report and Written Opinion received Nov. 9, 2018 in Application No. PCT/US2018/048873.
PCT; International Search Report and Written Opinion dated Apr. 8, 2010 in Application No. PCT/US2009/054235.
PCT; International Search Report and Written Opinion dated Jan. 18, 2019 in Application No. PCT/US2018/055264.
PCT; International Search Report and Written Opinion dated Mar. 12, 2018 in Application No. PCT/US2017/063025.
PCT; International Search Report and Written Opinion dated Mar. 7, 2018 in Application No. PCT/US2017/063105.
PCT; International Search Report and Written Opinion dated Apr. 18. 2017 in Application No. PCT/US2016/068922.
CN; Notice of the First Office Action dated Sep. 2, 2019 in Chinese Application No. 201680049272.8.
CN; Notice of the First Office Action dated Sep. 30, 2019 in Chinese Application No. 201780020478.2.
EP; European Search Report dated Jan. 30, 2019 in Application No. 16815467.2.
EP; European Search Report dated Aug. 2, 2019 in Application No. 16885434.7.
EP; European Search Report dated Jan. 29, 2020 in Application No. 17745013.7.
EP; European Search Report dated Aug. 2, 2019 in Application No. 17745026.9.
EP; European Search Report dated Jan. 29, 2020 in Application No. 17750776.1.
EP; European Search Report dated Oct. 24, 2019 in Application No. 17757146.0.
EP; European Search Report dated Mar. 6, 2020 in Application No. 17835231.6.
EP; European Search Report dated Feb. 7, 2020 in Application No. 17837566.3.
Ahn et al., "Electrical Immunosensor Based on a Submicron-Gap Interdigitated Electrode and Gold Enhancement," Biosensors and Bioelectronics, vol. 26, pp. 4690-4696, (2011).
Alayo et al., "Gold Interdigitated Nanoelectrodes as a Sensitive Analytical Tool for Selective Detection of Electroactive Species via Redox Cycling," Microchim Acta, vol. 183, pp. 1633-1639, (2016).
Antibody Structure Downloaded from https://absoluteantibody.com/antibody-resources/antibody-overview/antibody-structure/ (Mar. 1, 2019).
Bai et al., "Review: Gas Sensors Based on Conducting Polymers," Sensors, vol. 7, pp. 267-307, (2007).
Bailey et al., "DNA-Encoded Antibody Libraries: A Unified Platform for Multiplexed Cell Sorting and Detection of Genes and Proteins," Journal of American Chemical Society, vol. 129, pp. 1959-1967, (2007).
Bechelany et al. "Synthesis Mechanisms of Organized Nanoparticles: Influence of Annealing Temperature and Atmosphere," Crystal Growth and Design, vol. 10, pp. 587-596 (Oct. 21, 2010).
Berdat et al., "Label-Free Detection of DNA with Interdigitated Micro-Electrodes in a Fluidic Cell," Lab on a Chip, vol. 8, pp. 302-308, (2008).
Bhura, "3D Interdigitated Electrode Array (IDEA) Biosensor for Detection of Serum Biomarker," Master Thesis, Portland State University, 68 Pages, (2011).
Blossey, R., "Self-Cleaning Surfaces-Virtual Realities," Nature Materials, vol. 2(5), pp. 301-306, (May 2006).
Bonilla et al., "Electrical Readout of Protein Microarrays on Regular Glass Slides," Analytical Chemistry, vol. 83, pp. 1726-1731, (2011).
Botsialas et al., "A Miniaturized Chemocapacitor System for the Detection of Volatile Organic Compounds," Sensors and Actuators B, Chemical, vol. 177, pp. 776-784, (2013).
Branagan et al., "Enhanced Mass Transport of Electroactive Species to Annular Nanoband Electrodes Embedded in Nanocapillary Array Membranes," Journal of the American Chemical Society, vol. 134, pp. 8617-8624, (2012).
Braun et al., "DNA-Templated Assembly and Electrode Attachment of a Conducting Silver Wire," Letters to Nature, vol. 391(6669), pp. 775-778, (Feb. 1998).
Briglin et al., "Exploitation of Spatiotemporal Information and Geometric Optimization of Signal/Noise Performance Using Arrays of Carbon Black-Polymer Composite Vapor Detectors," Sensors and Actuators B, vol. 82, pp. 54-74, (2002).
Cassie, A.B.D. et al., "Wettability of Porous Surfaces," Transitions of the Faraday Society, vol. 40, pp. 546-551, (Jan. 1944) (Abstract Only).
Cerofolini et al., "A Hybrid Approach to Nanoelectronics: A Hybrid Approach to Nanoelectrics," Nanotechnology, Institute of Physics Publishing, GB, vol. 16, No. 8, pp. 1040-1047 (2005).
Chen, X. et al., "Electrical Nanogap Devices for Biosensing," Materials Today, vol. 13, pp. 28-41, (Nov. 2010).
Chen et al., "Electrochemical Approach for Fabricating Nanogap Electrodes with Well Controllable Separation," Applied Physics Letters, vol. 86, pp. 123105.1-123105.3, (2005).
Chen et al., "Fabrication of Submicron-Gap Electrodes by Silicon Volume Expansion for DNA-Detection," Sensors and Actuators A, vol. 175, pp. 73-77, (2012).
Choi, J. E. et al., "Fabrication of Microchannel with 60 Electrodes and Resistance Measurement," Flow Measurement and Instrumentation, vol. 21, pp. 178-183, (Sep. 2010) (Abstract Only).

(56) References Cited

OTHER PUBLICATIONS

Choi Y.S. et al., "Hybridization by an Electroatomical Genome on Detection on Using an Indicator-Free DNA on a Microelectrode-Array DNA Chip," Bulletin of the Korean Chemistry Society, vol. 26, pp. 379-383, (2005).
Choi, C. et al., "Strongly Superhydrophobic Silicon Nanowires by Supercritical CO2 Drying," Electronic Materials Letters, vol. 6 (2), pp. 59-64, (Jun. 2010).
Church et al., "Next-Generation Digital Information Storage in DNA," Science, vol. 337(6102), p. 6102, (Sep. 28, 2012).
Cosofret et al., "Microfabricated Sensor Arrays Sensitive to pH and K+ for Ionic Distribution Measurements in the Beating Heart," Analytical Chemistry, vol. 67, pp. 1647-1653, (1995).
Coulson S.R. et al., "Super-Repellent Composite Fluoropolymer Surfaces," The Journal of Physical Chemistry B., vol. 104(37), pp. 8836-8840, (Aug. 2000).
Dickey et al., "Electrically Addressable Parallel Nanowires with 30 NM Spacing from Micromolding and Nanoskiving," Nano Letters, vol. 8(12), pp. 4568-4573, (2008).
Fan et al., "Detection of MicroRNAs Using Target-Guided Formation of Conducting Polymer Nanowires in Nanogaps," Journal of the American Chemical Society, vol. 129, pp. 5437-5443, (2007).
Fink et al. "Electrical Conduction Through DNA Molecules," Nature, vol. 398, pp. 407-410 (Jan. 20, 1999).
Fuller et al., "Real-Time Single-Molecule Electronic DNA Sequencing by Synthesis Using Polymer-Tagged Nucleotides on a Nanopore Array," Proceedings of the National Academy of Sciences, vol. 113(19), pp. 5233-5523, (May 10, 2016).
Gapin, A.I. et al., "CoPt Patterned Media in Anodized Aluminum Oxide Templates," Journal of Applied Physics, vol. 99(8), pp. 08G902 (1-3), (Apr. 2006).
Ghindilis, A. et al., "Real Time Biosensor Platforms Fully Integrated Device for Impedimetric Assays," ECS Transactions, vol. 33, pp. 59-68, (2010).
Guo et al., "Conductivity of a single DNA duplex bridging a carbon nanotube gap," Nat. Nanotechnol., vol. 3, No. 3, pp. 1-12 (2008).
Han, "Energy Band Gap Engineering of Graphene Nanoribbons," Physical Review Letters, vol. 98, pp. 1-7, (May 16, 2007).
Han et al., "Redox Cycling in Nanopore-Confined Recessed Dual-Ring Electrode Arrays," Journal of Physical Chemistry C, vol. 120, pp. 20634-20641, (2016).
Hanief, Topic, Pineda-Vargas, "Solid State Dewetting of Continuous Thin Platinum Coatings," Nuclear Instruments and Methods in Physics Research, vol. 363, pp. 173-176, (2015).
Hashioka et al., "Deoxyribonucleic Acid Sensing Device with 40-NM-Gap-Electrodes Fabricated by Low-Cost Conventional Techniques," Applied Physics Letters, vol. 85(4), p. 687-688, (Jul. 2004).
He et al., "Electromechanical Fabrication of Atomically Thin Metallic Wires and Electrodes Separated with Molecular-Scale Gaps," Journal of Electroanalytical Chemistry, vol. 522, pp. 167-172, (Jan. 2002).
Heerema et al., "Graphene Nanodevices for DNA Sequencing," Nature Nanotechnology, vol. 11, pp. 127-136, (Feb. 3, 2016).
Henry et al., "Microcavities Containing Individually Addressable Recessed Microdisk and Tubular Nanoband Electrodes," Journal of the Electrochemical Society, vol. 146(9), pp. 3367-3373, (1999).
Hwang et al., "Electrical Transport Through 60 Base Pairs of Poly (dG)-Poly (dC) DNA Molecules," Applied Physics Letters, vol. 81(6), p. 1134-1136, (Aug. 2002).
Ino et al., "Addressable Electrode Array Device with IDA Electrodes for High-Throughput Detection," Lab on a Chip, vol. 11, p. 385-388, (2011).
Ino et al., "Local Redox-Cycling-Based Electrochemical Chip Device with Seep Microwells for Evaluation of Embryoid Bodies," Angewandte Chemie International Edition, vol. 51, pp. 6648-6652, (2012).
Iqbal et al., "Direct Current Electrical Characterization of ds-DNA in Nanogap Junctions," Applied Physics Letter, vol. 86, p. 153901-1-153901-3, (Apr. 2005).

Javey et al., "Layer-By-Layer Assembly of Nanowires for Three-Dimensional, Multifunctional Electronics," Nano Letters, vol. 7, pp. 773-777, (2007).
Khawli et al., "Charge Variants in IgG1-Isolation, Characterization, in Vitro Binding Properties and Pharmacokinetics in Rats," Landes Bioscience, vol. 2(6), pp. 613-623, (2010).
Kim, J. Y. et al., "Optically Transparent Glass with Vertically Aligned Surface Al2O3 Nanowires Having Superhydrophobic Characteristics," NANO: Brief Reports and Reviews, vol. 5(2), pp. 89-95, (Apr. 2010) (Abstract Only).
Kim et al., "Rapid Fabrication of Uniformly Sized Nanopores and Nanopore Arrays for Parallel DNA Analysis," Advances Materials, vol. 18, pp. 3149-3153, (Dec. 4, 2006).
Kitsara et al., "Single Chip Interdigitated Electrode Capacitive Chemical Sensor Arrays," Sensors and Actuators B, vol. 127, pp. 186-192, (2007).
Kitsara et al., "Small-Volume Multiparametric Electrochemical Detection at Low Cost Polymeric Devices Featuring Nanoelectrodes," SPIE, vol. 9518, 9 Pages, (2015).
Kraft, "Doped Diamond: A Compact Review on a New, Versatile Electrode Material," International Journal of Electrochemistry, vol. 2, pp. 355-385, (May 2007).
Kumar et al., "Terminal Phosphate Labeled Nucleotides: Synthesis, Applications and Linker Effect on Incorporation by DNA Polymerases," Nucleosides, Nucleotides and Nucleic Acids, Taylor and Francis, vol. 24, No. 5-7, pp. 401-408 (2005).
Lee, K. H. et al., "One-Chip Electronic Detection of DNA Hybridization using Precision Impedance-Based CMOS Array Sensor," Biosensors and Bioelectronics, vol. 26, pp. 1373-1379, (Dec. 15, 2010).
Lin et al., "An Addressable Microelectrode Array for Electrichemical Detection," Analytical Chemistry, vol. 80, pp. 6830-6833, (2008).
Liu et al., "Atomically Thin Molybdenum Disulfide Nanopores with High Sensitivity for DNA Translocation," ACS Nano, vol. 8, pp. 2504-2511, (Feb. 18, 2014).
Liu et al., "An Enzyme-Based E-DNA Sensor for Sequence-Specific Detection of Femtomolar DNA Targets," J. Am. Chem. Soc., vol. 130(21), pp. 6820-6825, (2008).
Liu et al., "Controllable Nanogap Fabrication on Microchip by Chronopotentiometry," Electrochimica Acta, vol. 50, pp. 3041-3047, (2005).
MacNaughton et al., "High-Throughput Heterogeneous Integration of Diverse Nanomaterials on a Single Chip for Sensing Applications," PLOS One, vol. 9(10), e111377, 7 Pages, (2014).
Mastrototaro et al., "Thin-Film Flexible Multielectrode Arrays for Voltage Measurements in the Heart," IEEE Engineering in Medicine & Biology Society 11th Annual International Conference, 1 Page, (1989).
Mastrototaro et al., "Rigid and Flexible Thin-Film Multielectrode Arrays for Transmural Cardiac Recording," IEEE Transactions on Biomedical Engineering, vol. 39, pp. 217-279, (1992).
Mirando-Castro et al., "Hairpin-DNA Probe for Enzyme-Amplified Electrochemical Detection of Legionella pnuemophila," Anal. Chem., vol. 79, pp. 4050-4055, (Jun. 1, 2007).
Nishida, et al. "Self-Oriented Immobilization of DNA Polymerase Tagged by Titanium-Binding Peptide Motif," Langmuir, vol. 31, pp. 732-740 (Dec. 17, 2014).
Niwa, O. et al., "Fabrication and Characteristics of Vertically Separated Interdigitated Array Electrodes," Journal of Electroanalytical Chemistry and Interfacial Electrochemistry, vol. 267 pp. 291-297, (Aug. 10, 1989) (Abstract Only).
Okinaka et al., ""Polymer" Inclusions in Cobalt-Hardened Electroplated Gold," Journal the of Electrochemical Society, vol. 125, p. 1745, (1978). (Abstract Only).
Park, S.J. et al., "Array-Based Electrical Detection of DNA with Nanoparticle Probes," Science, vol. 295, pp. 1503-1506, (Feb. 22, 2002).
Park, C.W. et al., "Fabrication of Poly-Si/ AU Nano-Gaps Using Atomic-Layer-Deposited $Al_2O_3$ as a Sacrificial Layer," Nanotechnology, vol. 16, pp. 361-364, (Feb. 1, 2005) (Abstract Only).
Parkin, I. P. et al., "Self-Cleaning Coatings," Journal of Materials Chemistry, vol. 15(17), pp. 1689-1695, (Dec. 2004).

(56) References Cited

OTHER PUBLICATIONS

Prins et al., "Room-Temperature Gating of Molecular Junctions Using Few-Layer Graphene Nanogap Electrodes," Nano Letters, vol. 11, pp. 4607-4611, (Oct. 21, 2011).
Pugliese et al., "Processive Inforporation of Deoxynucleoside Triphosphate Analogs by Single-Molecule DNA Polymerase I (Klenow Fragment) Nanocircuits," Journal of the American Chemical Society, vol. 137, No. 30, pp. 9587-9594 (2015).
Qing et al., "Finely Tuning Metallic Nanogap Size with Electrodeposition by Utilizing High-Frequency Impedance in Feedback," Angewandte Chemie Int ed, vol. 44, pp. 7771-7775, (2005).
Reed et al., "Conductance of a Molecular Junction Reports," Science, vol. 278, pp. 252-254, (Oct. 1997).
Reichert et al., "Driving Current Through Single Organic Molecules," Physical Review Letters, vol. 88(17), pp. 176804-1-176804-4, (Apr. 2002).
Roppert et al., "A New Approach for an Interdigitated Electrodes DNA-Sensor," XVIIIth International Symposium on Bioelectrochemistry and Bioenergetics, Bioelectrochemistry, p. 143, (2005).
Roy, S. et al., "Mass-Produced Nanogap Sensor Arrays for Ultra-Sensitive Detection of DNA," Journal of the American Chemical Society, vol. 131, pp. 12211-12217, (Aug. 5, 2009) (Abstract Only).
Ruttkowski, E. et al., "CMOS based Arrays of Nanogaps Devices for Molecular Devices," Proceedings of 2005 5th IEEE Conference on Nanotechnology, vol. 1, pp. 438-441, (Jul. 2005) (Abstract Only).
Sanguino et al., "Interdigitated Capacitive Immunosensors with PVDF Immobilization Layers," IEEE Sensors Journal, vol. 14(4), pp. 1260-1265, (Apr. 2014).
Santschi et al., "Interdigitated 50nm Ti Electrode Arrays Fabricated using $XeF_2$ Enhanced Focused Ion Beam Etching," Nanotechnology, vol. 17, pp. 2722-2729, (2006).
Schaefer et al., "Stability and Dewetting Kinetics of Thin Gold Films on Ti, TiOx, and ZnO Adhesion Layers," Acta Materialia, vol. 61, pp. 7841-7848, (2013).
Schrott, W. et al., "Metal Electrodes in Plastic Microfluidic Systems," Microelectronic Engineering, vol. 86, pp. 1340-1342, (Jun. 2009).
Shimanovsky et al., "Hiding Data in DNA," International Workshop on Information Hiding, Lecture Notes in Computer Science, pp. 373-386, (Dec. 18, 2012).
Shimoda, T. et al., "Solution-Processed Silicon Films and Transistors," Nature, vol. 440(7085), pp. 783-786, (Apr. 2006).
Sholders et al., "Distinct Conformations of a Putative Translocation Element in Poliovirus Polymerase," Journal of Molecular Biology, vol. 426(7), pp. 1407-1419, (Apr. 3, 2014).
Singh et al., "3D Nanogap Interdigitated Electrode Array Biosensors," Analytical and Bioanalytical Chemistry, vol. 397, pp. 1493-1502, (2010).
Singh et al., "Evaluation of Nanomaterials-Biomolecule Hybrids for Signals Enhancement of Impedimetric Biosensors," 11th IEEE International Conference on Nanotechnology, pp. 707-710, (2011).
Singh et al., "Nanoparticle-Enhanced Sensitivity of a Nanogap-Interdigitated Electrode Array Impedimetric Biosensor," Langmuir, vol. 27, pp. 13931-13939, (2011).
Stagni, C. et al., "CMOS DNA Sensor Array with Integrated A/D Conversation Based on Label-Free Capacitance Measurement," IEEE Journal of Solid-State Circuits, vol. 41, pp. 2956-2964, (Nov. 20, 2006).
Stenning, "The Investigation of Grain Boundary Development and Crystal Synthesis of Thin Gold Films on Silicon Wafers," http://www.ucl.ac.uk/~ucapikr/projects, (March 31, 2009).
Su, Y., "Modeling and Characteristic Study of Thin Film Based Biosensor Based on COMSOL," Mathematical Problems in Engineering, Article 581063 (6 Pages), (Apr. 7, 2014).
Thompson, "Solid-State Dewetting of Thin Films," Department of Materials Science and Engineering, vol. 42, pp. 399-434, (2012).
Urban, M. et al., "A Paralleled Readout System for an Electrical DNA-Hybridization Assay Based on a Microstructured Electrode Array," Review of Scientific Instruments, vol. 74, pp. 1077-1081, (Jan. 2003) (Abstract Only).
Van Gerwin et al., "Nanoscaled Interdigitated Electrode Arrays for Biochemical Sensors," Sensors and Actuators B, vol. 49, pp. 73-80, (1998).
Van Megan et al., "Submicron Electrode Gaps Fabricated by Gold Electrodeposition at Interdigitated Electrodes," Key Engineering Materials, vol. 605, pp. 107-110, (2014).
Wang et al., "Electronics and Optoelectronics of Two-Dimensional Transition Metal Dichalcogenides," Nature Nanotechnology, vol. 7, pp. 699-712, (Nov. 6, 2012).
Xu et al., "Fabrication of Complex Metallic Nanostructures by Nanoskiving," American Chemical Society Nano, vol. 1(3), pp. 215-227, (2007).
Zafarani et al., "Electrochemical Redox Cycling in a New Nanogap Sensor: Design and Simulation," Journal of Electroanalytical Chemistry, vol. 760, pp. 42-47, (2015).
USPTO; Non-Final Office Action dated Sep. 22, 2020 in U.S. Appl. No. 16/639,716.
USPTO; Non-Final Office Action dated Oct. 2, 2020 in U.S. Appl. No. 16/073,693.
USPTO; Non-Final Office Action dated Nov. 9, 2020 in U.S. Appl. No. 16/731,749.
PCT; International Search Report and Written Opinion dated Jun. 9, 2020 in Application No. PCT/US2020/13218.
PCT; International Search Report and Written Opinion dated Aug. 6, 2020 in Application No. PCT/US2020/25068.
PCT; International Search Report and Written Opinion dated Sep. 4, 2020 in Application No. PCT/US2020/28004.
EP; European Search Report dated Sep. 30, 2020 in Application No. 17893481.6.
JP; Office Action dated Aug. 13, 2020 in Japanese Application No. 2017-566864.
CN; Office Action dated Aug. 14, 2020 in Chinese Patent Application No. 201680083636.4.
Yang et al., "Two-Dimensional Graphene Nanoribbons," J. Am. Chem. Soc. vol. 130, Issue 13 (2008).
USPTO; Notice of Allowance dated Nov. 24, 2020 in U.S. Appl. No. 16/477,106.
USPTO; Notice of Allowance dated Dec. 7, 2020 in U.S. Appl. No. 16/878,484.
USPTO; Final Office Action dated Dec. 14, 2020 in U.S. Appl. No. 16/684,338.
USPTO; Final Office Action dated Jan. 6, 2021 in U.S. Appl. No. 16/070,133.
USPTO; Final Office Action dated Jan. 11, 2021 in U.S. Appl. No. 16/479,257.
USPTO; Non-Final Office Action dated Dec. 15, 2020 in U.S. Appl. No. 16/831,722.
JP; Office Action dated Dec. 2, 2020 in Japanese Patent Application No. 2018-536737.
EP; European Search Report dated Dec. 23, 2020 in Application No. 18790713.4.
EP; European Search Report dated Nov. 19, 2020 in Application No. 18739158.6.
EP; European Search Report dated Dec. 14, 2020 in Application No. 18799263.1.
Ali et al., "DNA hybridization detection using less than 10-nm gap silicon nanogap structure," Sensors and Actuators A. vol. 199, pp. 304-309 (2013).
Bornholt et al., "A DNA-Based Archival Storage System", Architectural Support for Programming Languages and Operating Systems, pp. 637-649 (2016).
Chen et al., "Silicon nanowire field-effect transistor-based biosensors for biomedical diagnosis and cellular recording investigation", Nano Today, Elsevier, Amsterdam, NL, vol. 6, No. 2, pp. 131-154 (2011).
Grass et al., "Robust Chemical Preservation of Digital Information on DNA in Silica with Error-Correcting Codes", Angewandte Chemie International Edition, vol. 54, No. 8, pp. 2552-2555 (2015).

(56) References Cited

OTHER PUBLICATIONS

Hatcher et al., "PNA versus DNA: Effects of Structural Fluctuations on Electronic Structure and Hole-Transport Mechanisms," J. Amer. Chem. Soc., 130, pp. 11752-11761 (2008).
Korlach et al., "Real-time DNA sequencing from single polymerase molecules,"11, Methods in Enzymology, Academy Press, vol. 472, pp. 431-455 (2010).
Paul et al., "Charge transfer through Single-Stranded Peptide Nucleic Acid Composed of Thymine Nucleotides," J. Phy. Chem. C 2008, 112, pp. 7233-7240 (2008).
Shin et al., "Distance Dependence of Electron Transfer Across Peptides with Different Secondary Structures: The Role of Peptide Energetics and Electronic Coupling," J. Amer. Chem. Soc. 2003, 125, pp. 3722-3732 (2003).
Venkatramani et al., "Nucleic Acid Charge Transfer: Black, White and Gray," Coard Chem Rev., 255(7-8): pp. 635-648 (2011).

\* cited by examiner

EXAMPLE BINARY DATA PAYLOAD  00101001100111001111101000101101

EXAMPLE BINARY ENCODING SCHEMES (BES)

| BES1 | BES2 | BES3 | BES4 | BES5 | BES6 |
|---|---|---|---|---|---|
| 00 → A | 0 → T | 0 → AA | 0 → X | 000 → A | 0 → GATT |
| 01 → C | 1 → G | 1 → CCC | 1 → Y | 001 → C | 1 → ACA |
| 10 → G | | | | 010 → G | |
| 11 → T | | | | 011 → T | |
| | | | | 100 → X | |
| | | | | 101 → Y | |
| | | | | 110 → W | |
| | | | | 111 → Z | |

BES1  00101001100111001111101000101101
      A C G C T A T T G G A G T C

BES2  00101001100111001111101000101101
      AACACAACCAACCCCACAAACACCAC

BES3  00101001100111001111101000101101
      AAAACCCAACCCCCAAAACCCCCCCAACCCCCCCAACCCCCCAACCCAACCC

BES5  00101001100111001111101000101101
      C G T C W T Z G C T T

FIG.4

METHODS, APPARATUS AND SYSTEMS FOR AMPLIFICATION-FREE DNA DATA STORAGE

CROSS-REFERENCE TO RELATED APPLICATIONS

This application claims priority to and the benefit of U.S. Provisional Patent Application Ser. No. 62/570,458, filed Oct. 10, 2017 and entitled "Methods, Apparatus and Systems for Amplification-Free DNA Data Storage," the disclosure of which is incorporated herein by reference in its entirety.

FIELD

The present disclosure generally relates to electronic data storage and retrieval, and more particularly to an amplification-free DNA information storage and retrieval system for storing and retrieving digital data using DNA molecules.

BACKGROUND

The advent of digital computing in the $20^{th}$ Century created the need for archival storage of large amounts of digital or binary data. Archival storage is intended to house data for long periods of time, e.g., years, decades or longer, in a way that is very low cost, and that supports the rare need to re-access the data. Although an archival storage system may feature the ability to hold unlimited amounts of data at very low cost, such as through a physical storage medium able to remain dormant for long periods of time, the data writing and recovery in such a system can be the relatively slow or otherwise costly processes. The dominant forms of archival digital data storage that have been developed to date include magnetic tape, and, more recently, compact optical disc (CD). However, as data production grows, there is a need for even higher density, lower cost, and longer lasting archival digital data storage systems.

It has been observed that in biology, the genomic DNA of a living organism functions as a form of digital information archival storage. On the timescale of the existence of a species, which may extend for thousands to millions of years, the genomic DNA in effect stores the genetic biological information that defines the species. The complex enzymatic, biochemical processes embodied in the biology, reproduction and survival of the species provide the means of writing, reading and maintaining this information archive. This observation has motivated the idea that perhaps the fundamental information storage capacity of DNA could be harnessed as the basis for high density, long duration archival storage of more general forms of digital information.

What makes DNA attractive for information storage is the extremely high information density resulting from molecular scale storage of information. In theory for example, all human-produced digital information recorded to date, estimated to be approximately 1 ZB (ZettaByte) (~$10^{21}$ Bytes), could be recorded in less than $10^{22}$ DNA bases, or $\frac{1}{60}^{th}$ of a mole of DNA bases, which would have a mass of just 10 grams. In addition to high data density, DNA is also a very stable molecule, which can readily last for thousands of years without substantial damage, and which could potentially last far longer, for tens of thousands of years, or even millions of years, such as observed naturally with DNA frozen in permafrost or encased in amber.

In spite of these attractions, using a single molecule of DNA for digital information storage and retrieval could be inefficient or even impossible due to the many sources of molecular structure errors in synthesizing a DNA molecule, loss/degradation of the molecule, and limits of signal detection from DNA sequencers used to sequence the molecule. Thus, it is frequently proposed that amplification be incorporated to provide many more molecules to engage in all these processes. However, amplification will add cost, time and operational complexity to the DNA information system. Therefore what are needed are specific processes that individually or collectively remove the need for amplification steps in the various processes that comprise a DNA data storage system.

SUMMARY

In various embodiments, an amplification-free DNA information storage and retrieval system is disclosed. In various aspects, the system comprises a DNA reading device, a digital data encoding/decoding algorithm, and a DNA writing device, wherein the properties of these three elements are co-optimized to minimize or reduce various cost metrics and increase overall system performance. In various aspects, the co-optimization may comprise reducing the error rate of the system, through balancing, avoiding, or correcting the errors in DNA reading and writing. In other instances, the co-optimization may comprise reducing the DNA reading or writing time in the system, e.g., by avoiding the use of slower speed DNA sequence motifs, and/or by using error correction/avoidance to compensate for errors incurred from rapid operation of the system.

In various embodiments of the present disclosure, a method of archiving information is described. The method comprises: converting the information into one or more nucleotides using an encoding scheme, the nucleotides predetermined to generate distinguishable signals relating to the information in a measurable electrical parameter of a molecular electronics sensor; assembling the one or more nucleotides into a nucleotide sequence; and synthesizing a pool of replicate DNA molecules without amplification of the DNA molecules, wherein each replicate DNA molecule incorporates the nucleotide sequence.

In various embodiments, the information comprises a string of binary data.

In various embodiments, the encoding scheme converts one or more 0/1 bits of binary data within the string of binary data into a sequence motif comprising more than one nucleotide.

In various embodiments, the step of converting the information comprises dividing the string of binary data into segments, wherein each segment encodes one sequence motif.

In various embodiments, the binary data bit 0 encodes a homopolymer of A, and the binary data bit 1 encodes a homopolymer of C.

In various embodiments, one or more of the nucleotides comprises a modified nucleotide.

In various embodiments, the one or more nucleotides comprise nucleotides that are resistant to secondary structure formation in the replicate DNA molecules compared to a variant of the same nucleotides.

In various embodiments, the encoding scheme comprises any one or combination of BES1, BES2, BES3, BES4, BES5 and BES6 illustrated in FIG. 4.

In various embodiments, the method of archiving information further comprises: exposing at least one of the replicate DNA molecules to the molecular electronics sensor without prior amplification of the DNA molecules; generating the distinguishable signals; and converting the distinguishable signals into the information, wherein the molecular electronics sensor comprises a pair of spaced-apart electrodes and a molecular sensor complex attached to each electrode to form a sensor circuit, wherein the molecular sensor complex comprises a bridge molecule electrically wired to each electrode in the pair of spaced-apart electrodes and a probe molecule conjugated to the bridge molecule.

In various embodiments, the step of exposing at least one of the replicate DNA molecules to the molecular electronics sensor comprises suspending the pool of DNA molecules in a buffer, taking an aliquot of the buffer, and providing the aliquot to the sensor.

In various embodiments, the buffer solution comprises modified dNTPs.

In various embodiments, the measurable electrical parameter of the sensor comprises a source-drain current between the spaced-apart electrodes and through the molecular sensor complex.

In various embodiments, the probe molecule for the sensor comprises a polymerase and the measurable electrical parameter of the sensor is modulated by enzymatic activity of the polymerase while processing any one of the replicate DNA molecules.

In various embodiments, the polymerase comprises the Klenow Fragment of *E. coli* Polymerase I, and the bridge molecule comprises a double-stranded DNA molecule.

In various embodiments of the present disclosure, a method of archiving and retrieving a string of binary data in an amplification-free DNA information storage and retrieval system is described. The method comprises: dividing the string of binary data into segments of at least one binary bit; assigning each segment to a sequence motif, each sequence motif comprising at least two nucleotides, the sequence motifs predetermined to generate distinguishable signals in a measurable electrical parameter of a molecular electronics sensor; assembling the sequence motifs into a nucleotide sequence; synthesizing a pool of replicate DNA molecules using an amplification-free DNA writing method on a solid support, each replicate DNA molecule incorporating the nucleotide sequence; suspending the pool of DNA molecules in a buffer; taking an aliquot of the buffer; providing the aliquot to the sensor without prior amplification of the DNA molecules; generating the distinguishable signals; and converting the distinguishable signals into the string of binary data, wherein the sensor comprises a pair of spaced apart electrodes and a molecular sensor complex attached to each electrode to form a molecular electronics circuit, wherein the molecular sensor complex comprises a bridge molecule electrically wired to each electrode in the pair of spaced-apart electrodes and a probe molecule conjugated to the bridge molecule.

BRIEF DESCRIPTION OF THE DRAWING FIGURES

Figure 5:
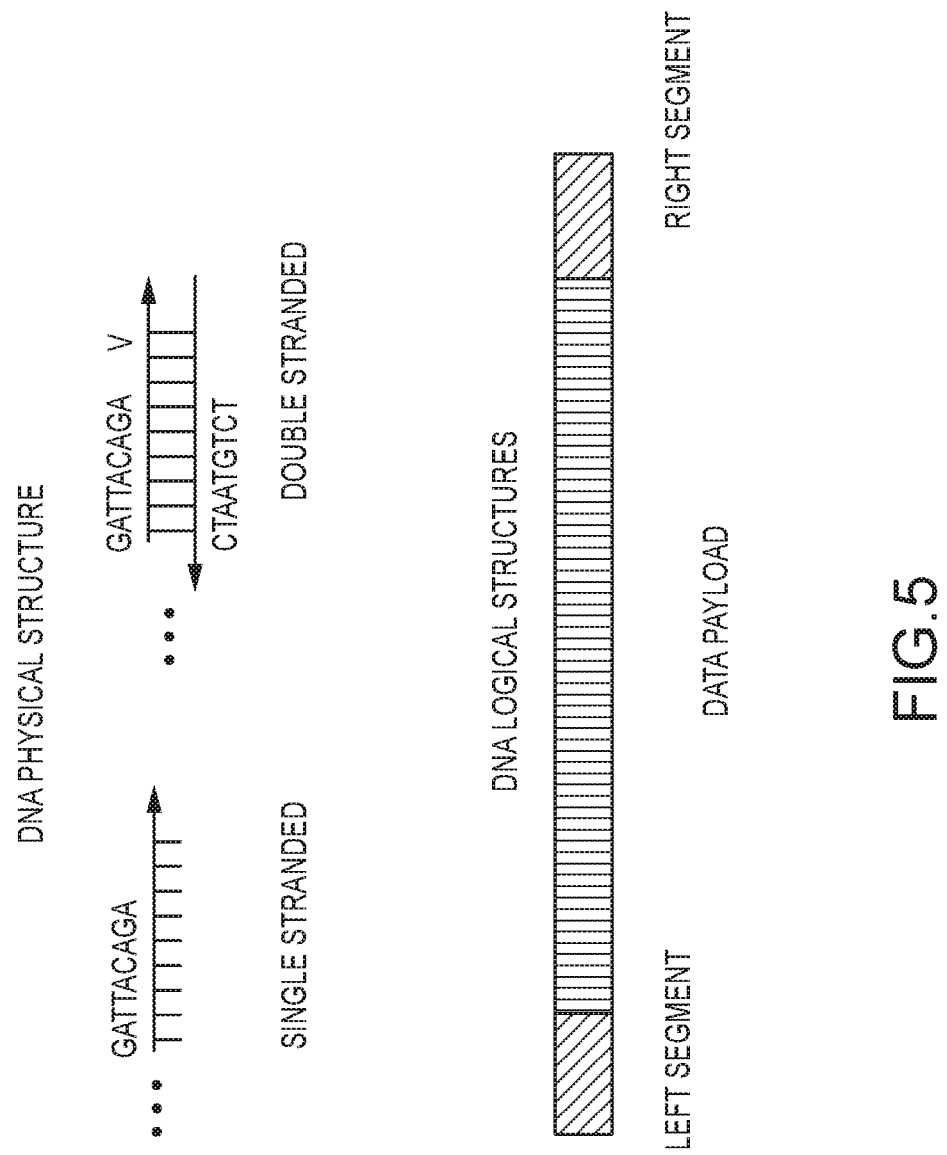
Figure 6:
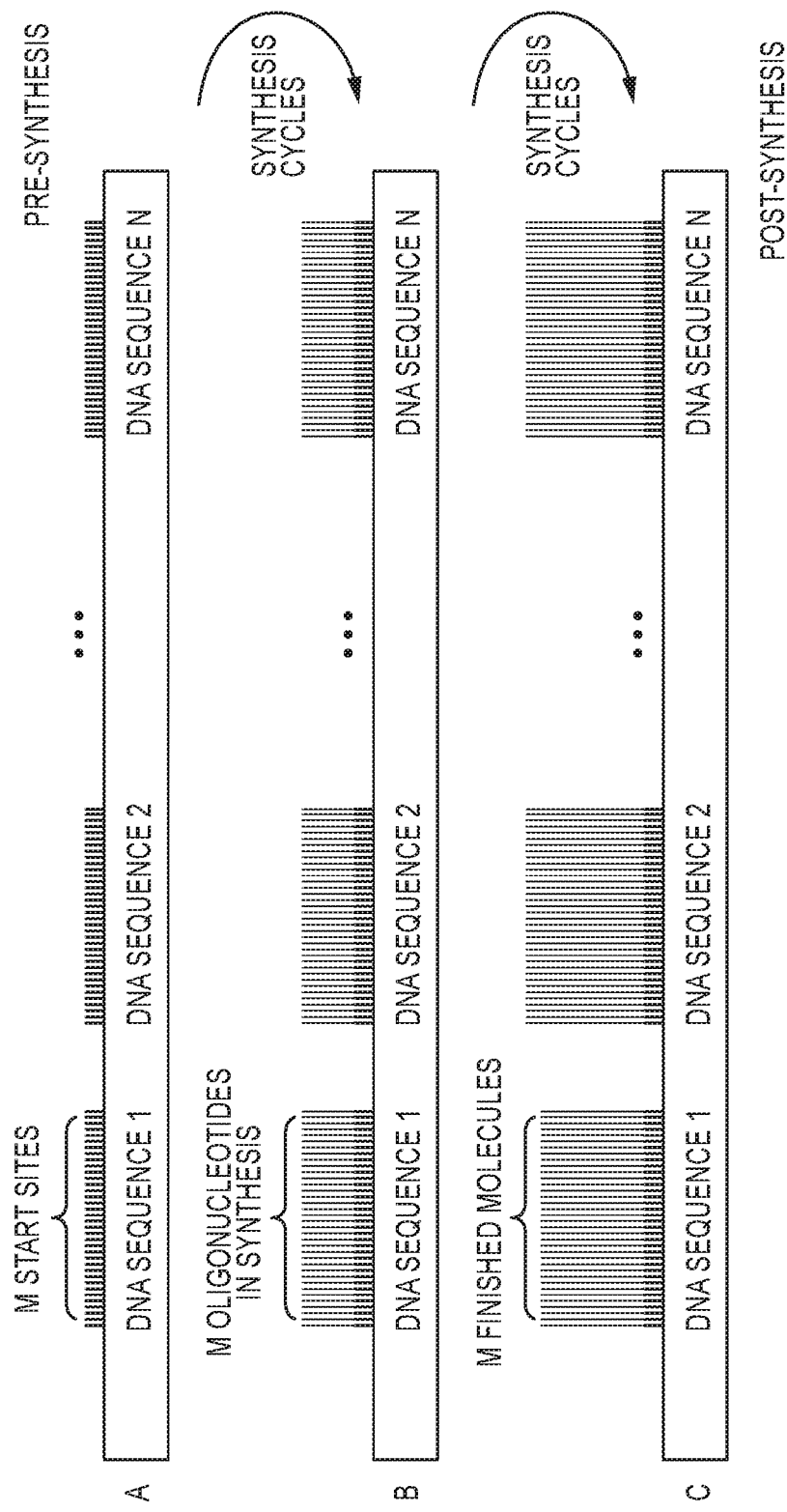
Figure 7:
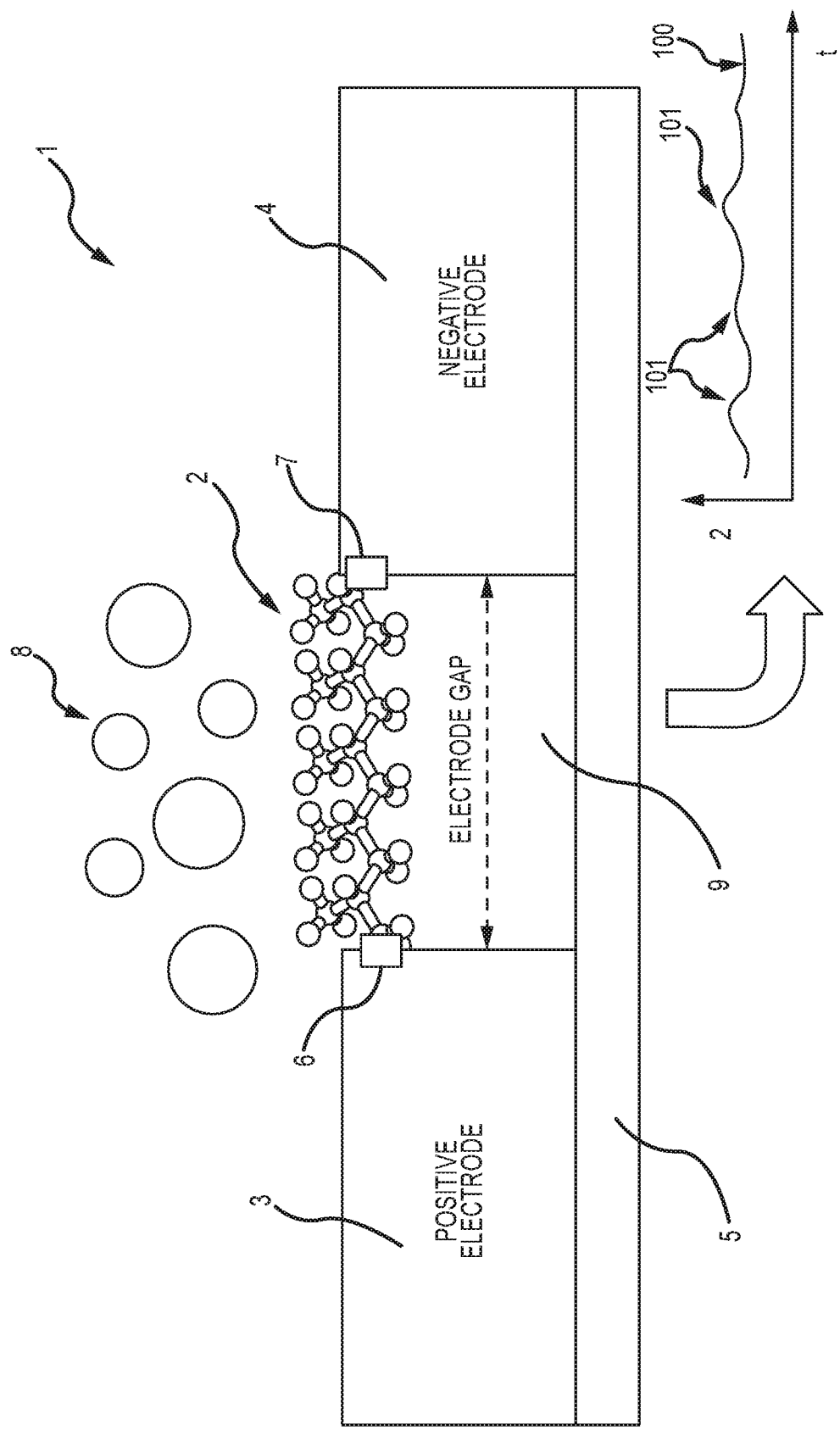
Figure 8:
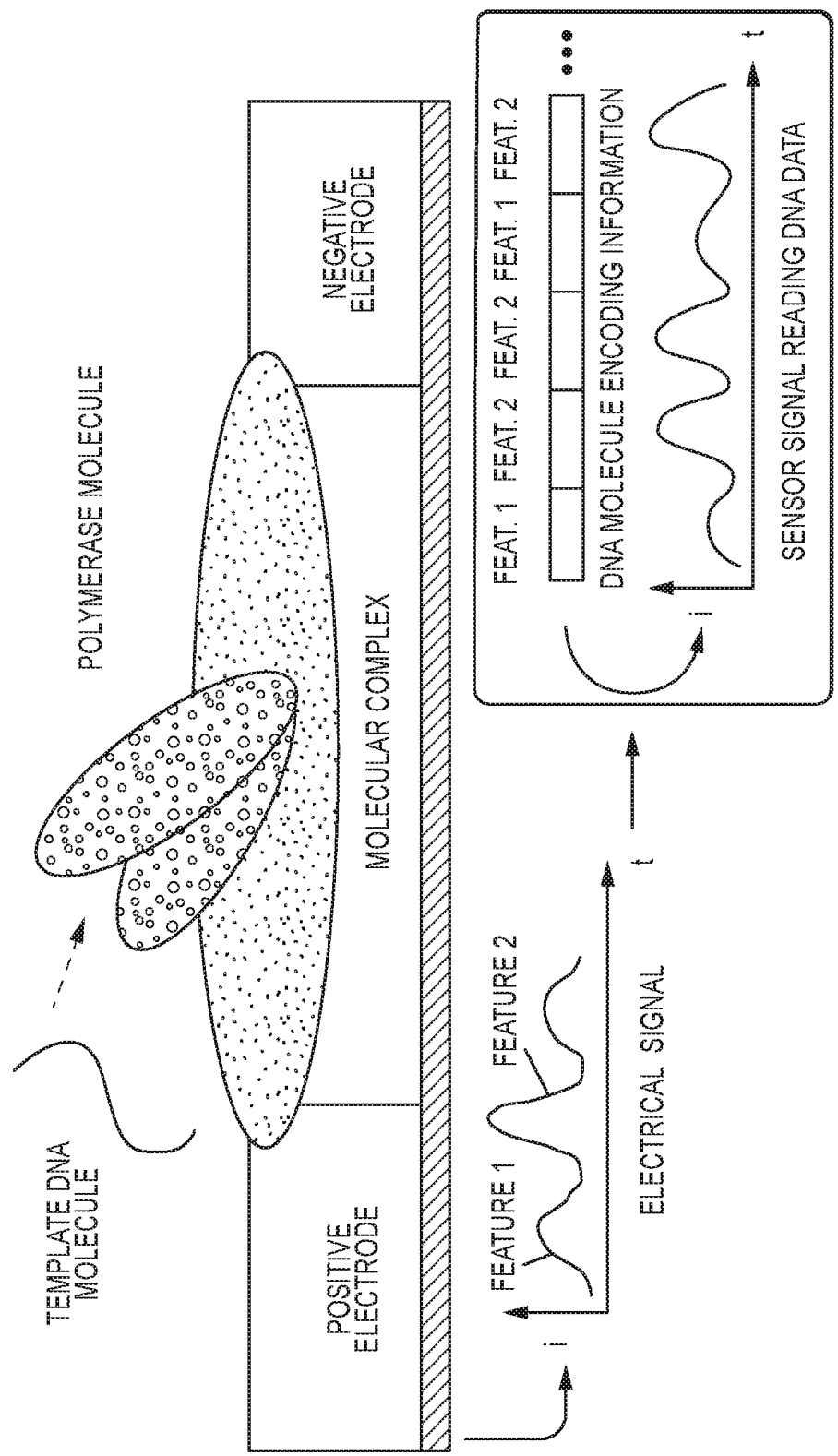
Figure 9:
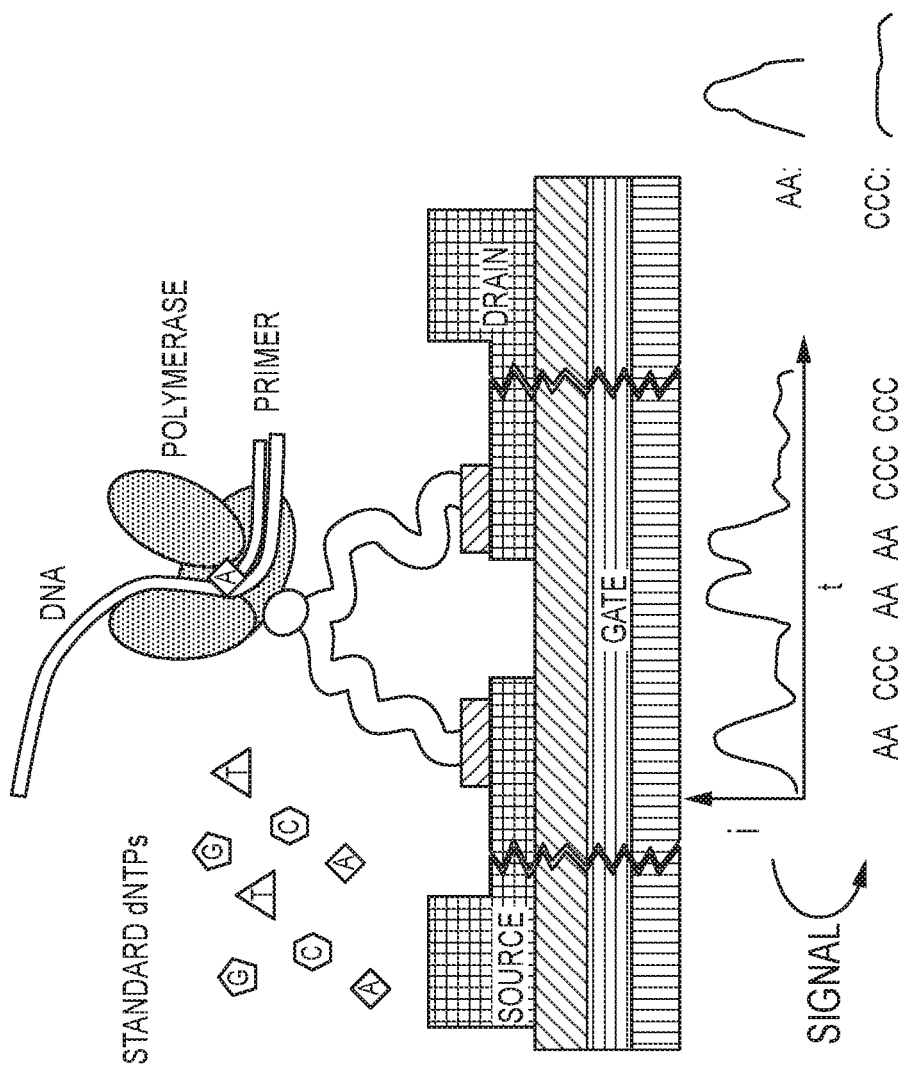
Figure 10:
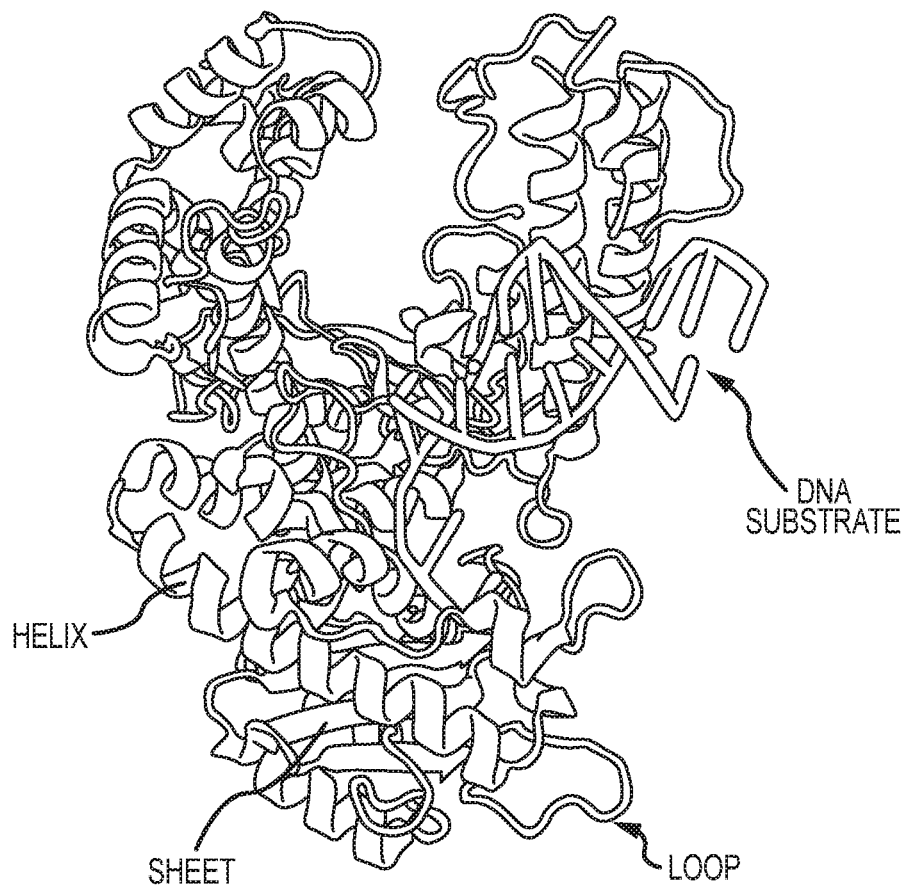
Figure 11:
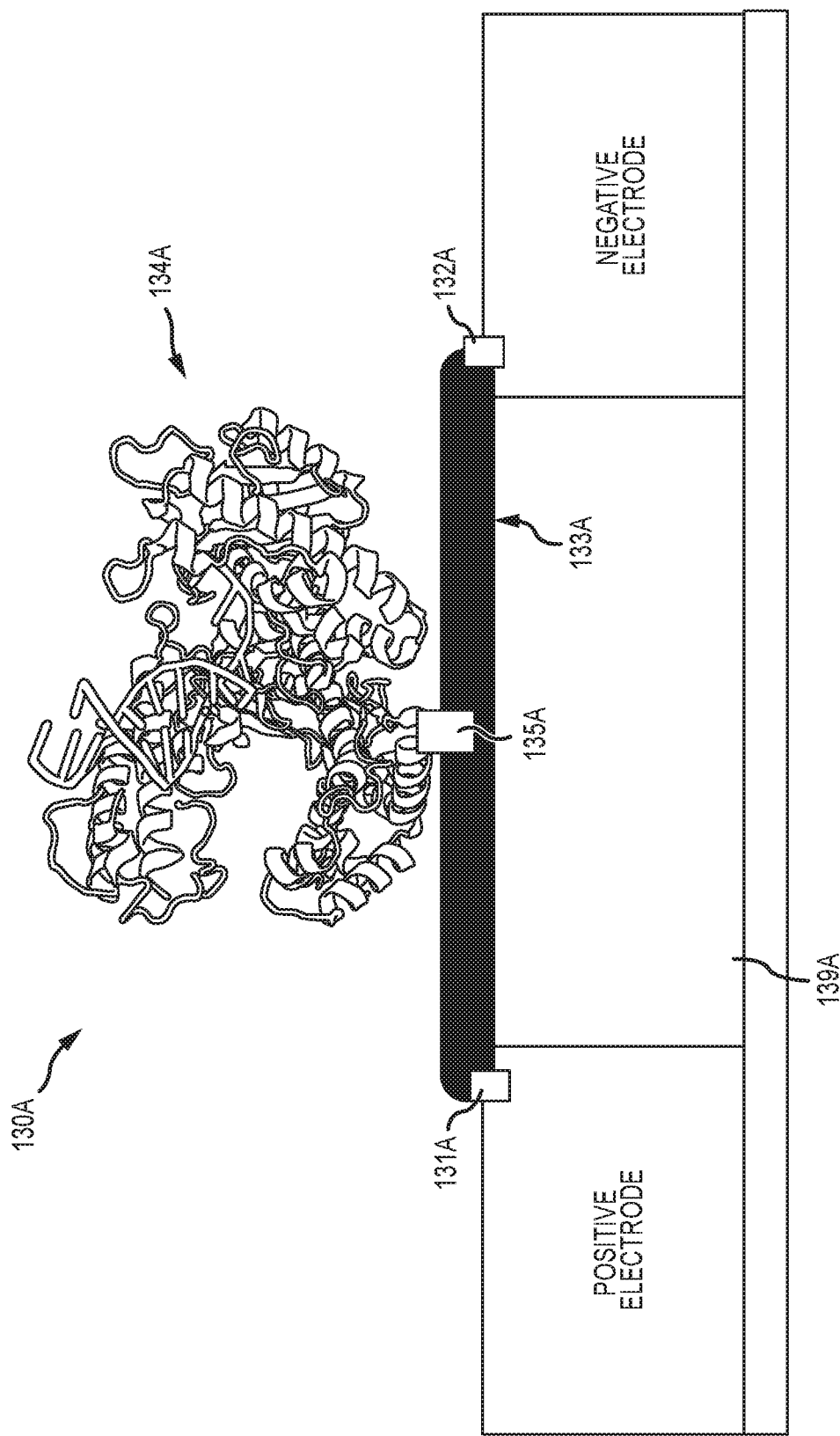
Figure 12:
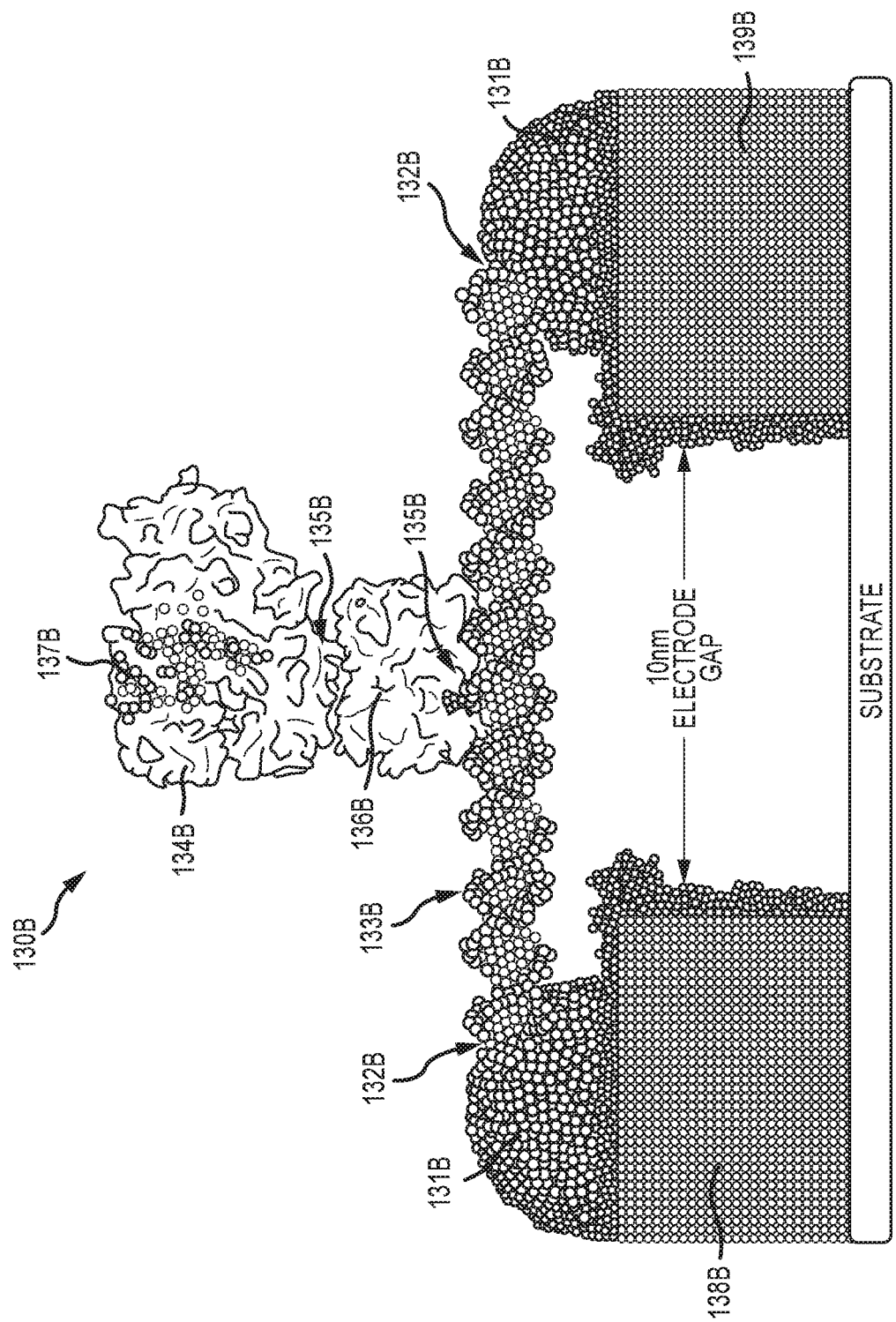
Figure 13:
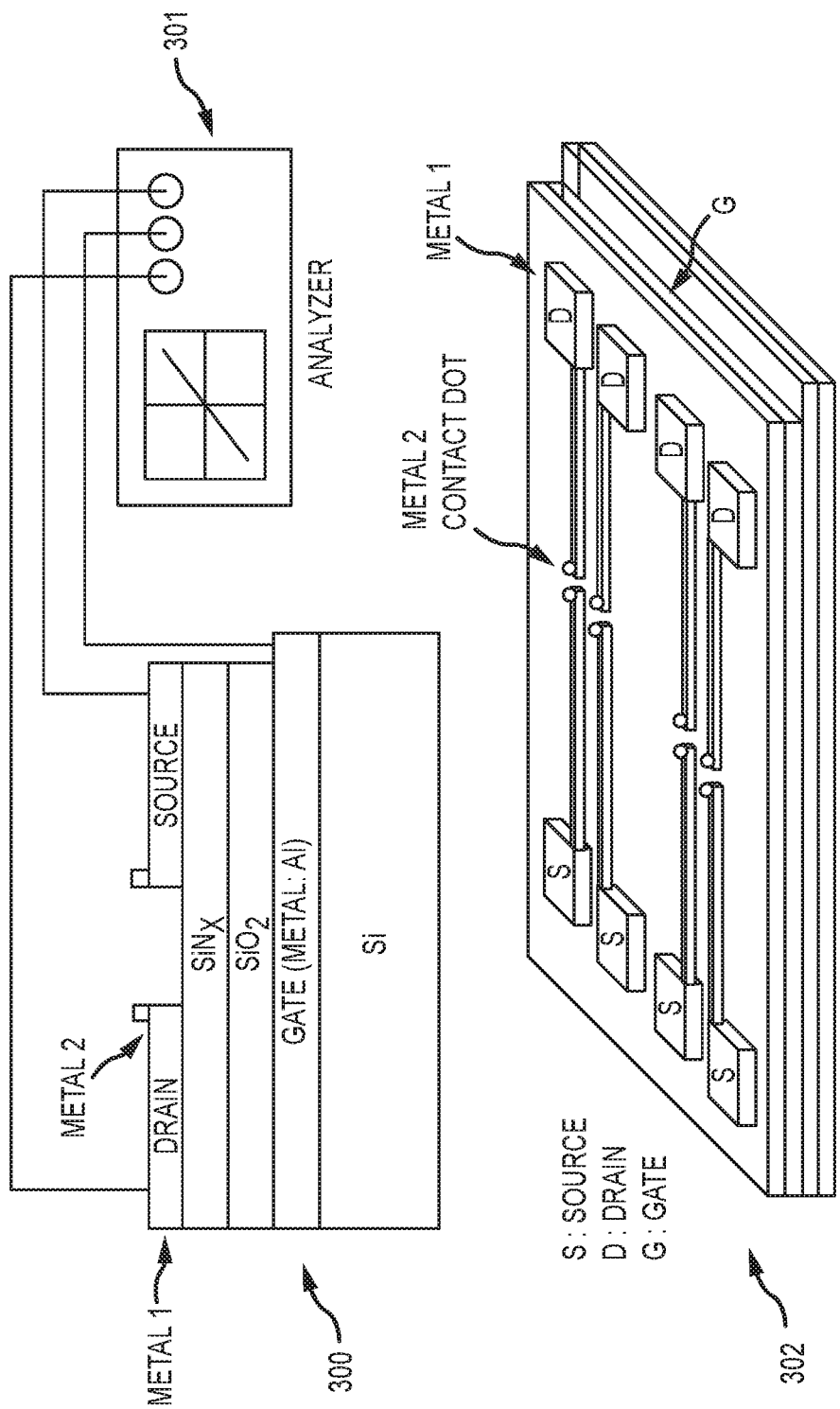
Figure 14:
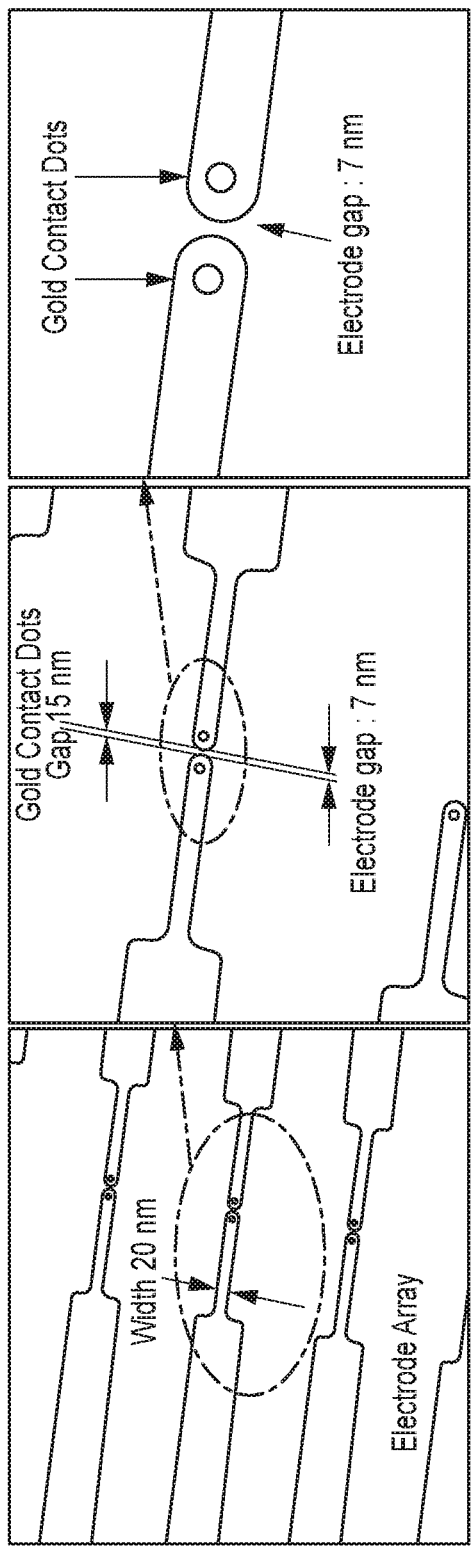
Figure 15:
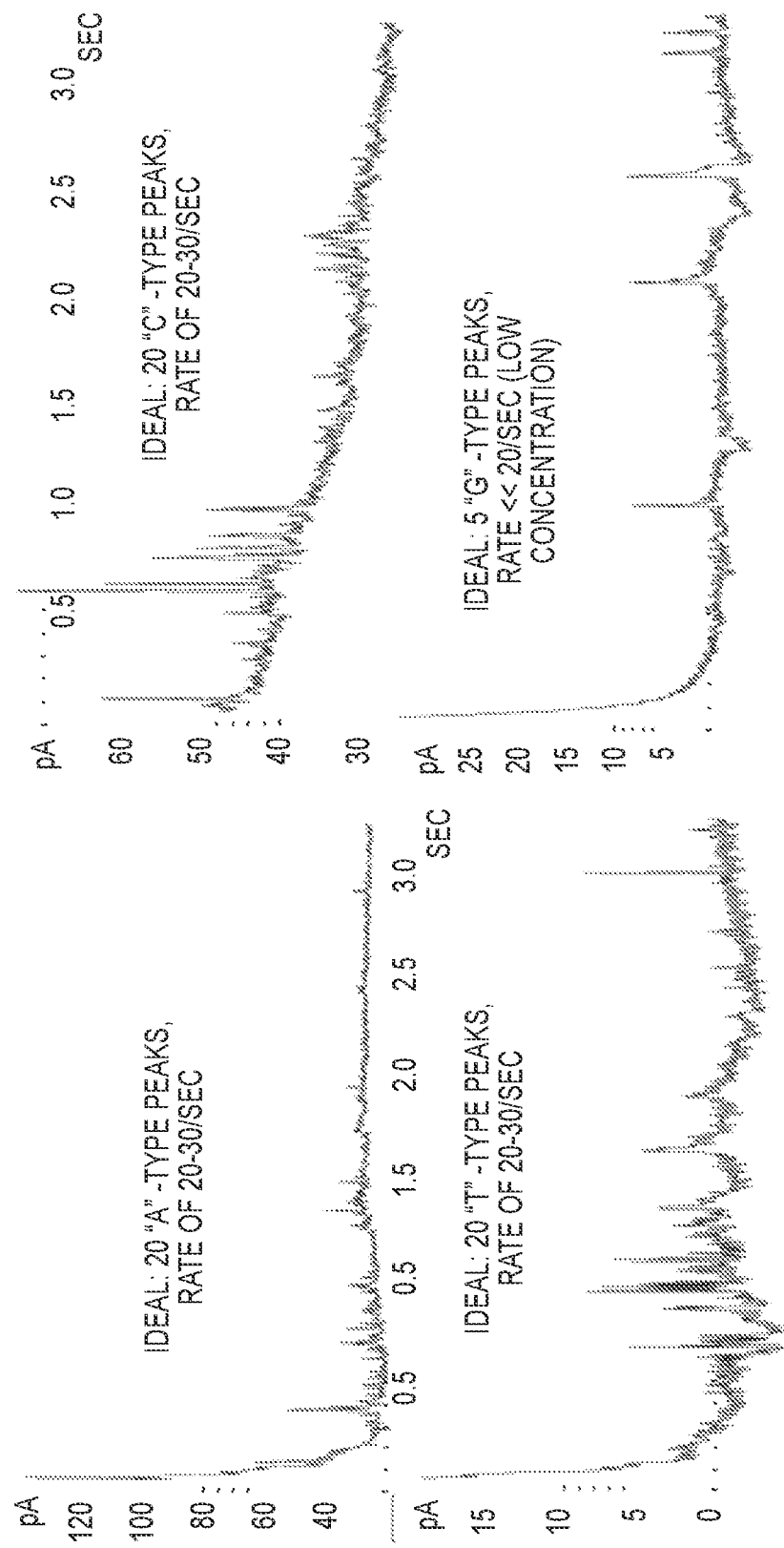
Figure 16:
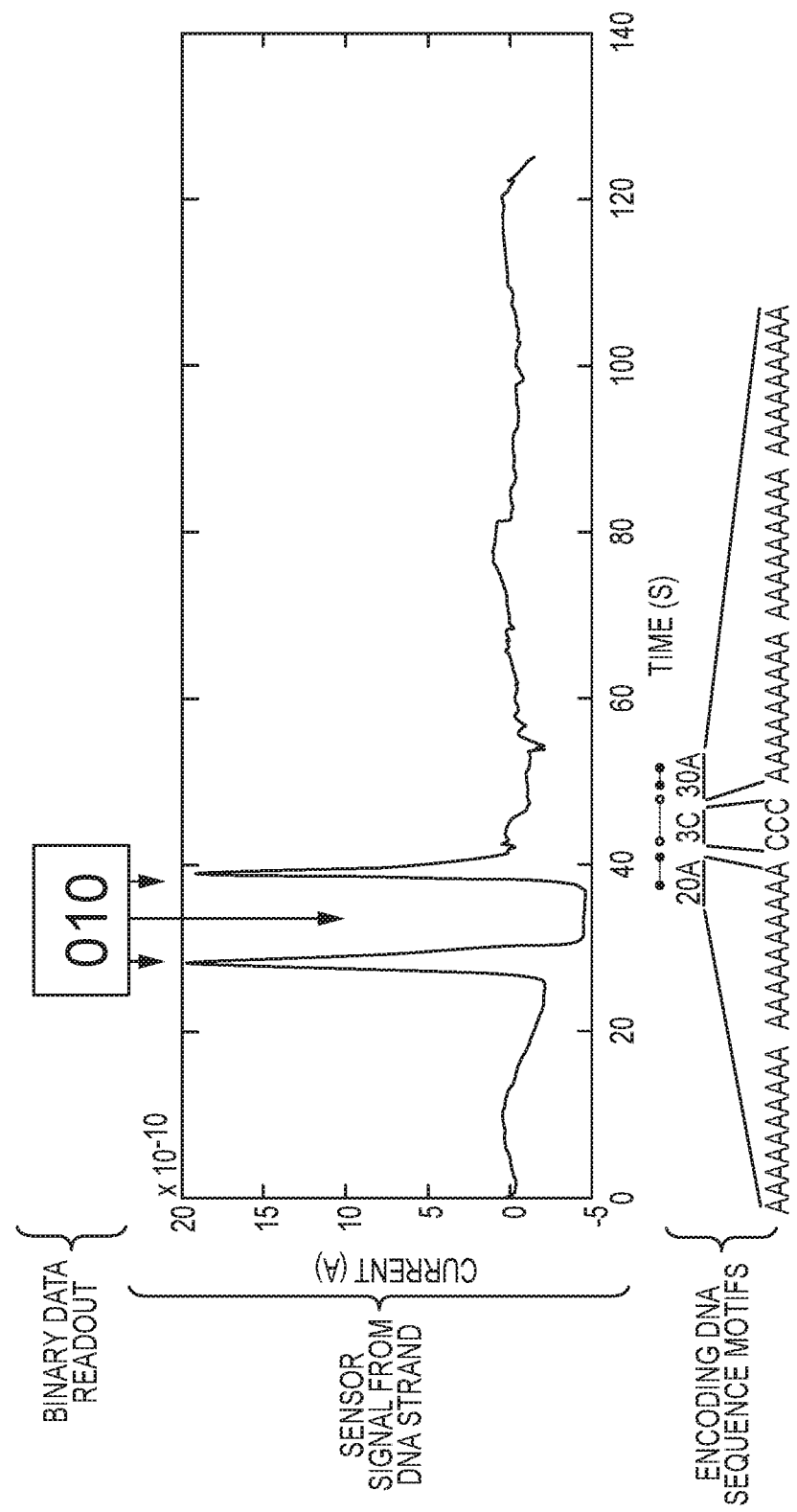
Figure 17:
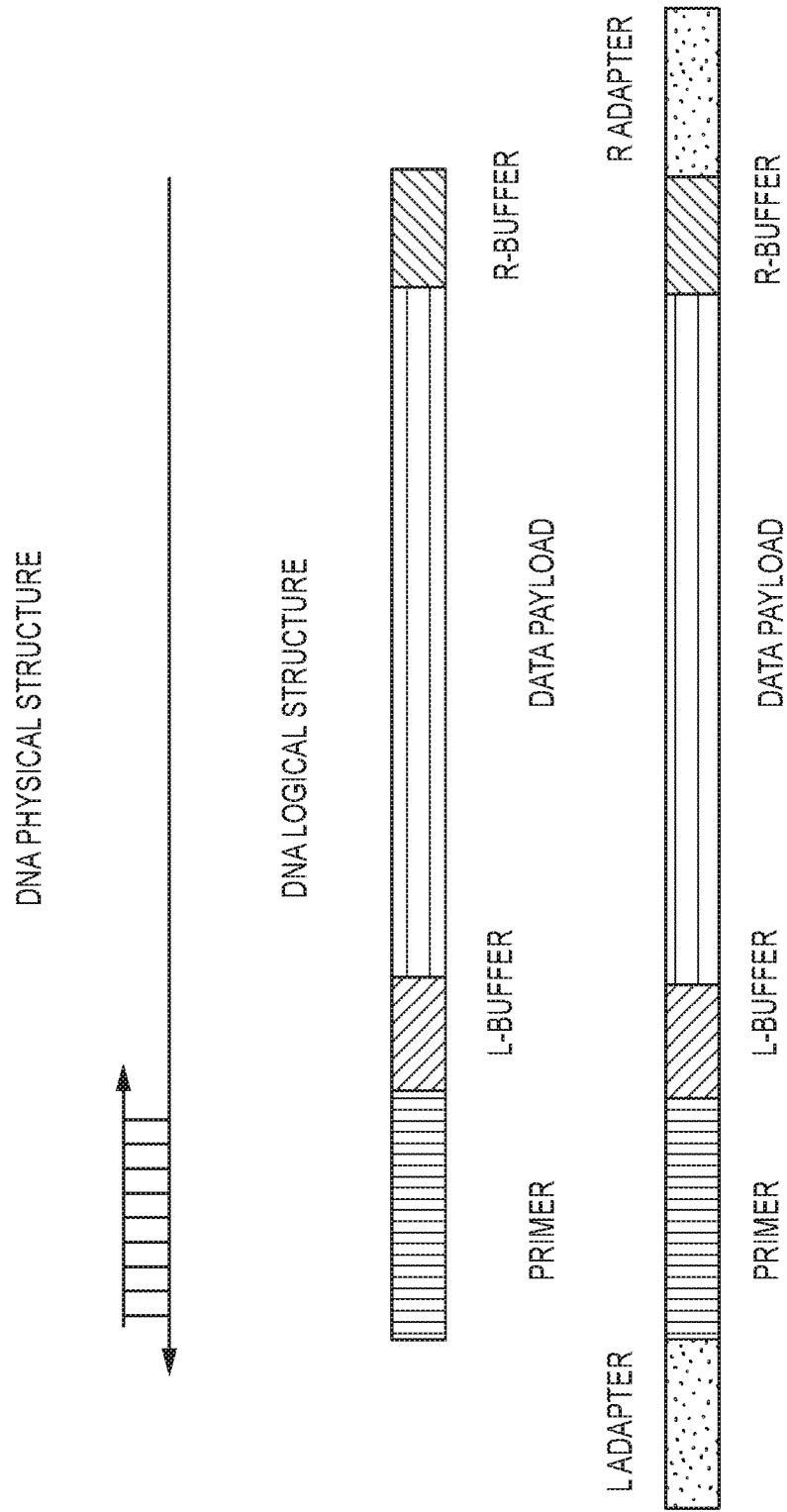
Figure 18:
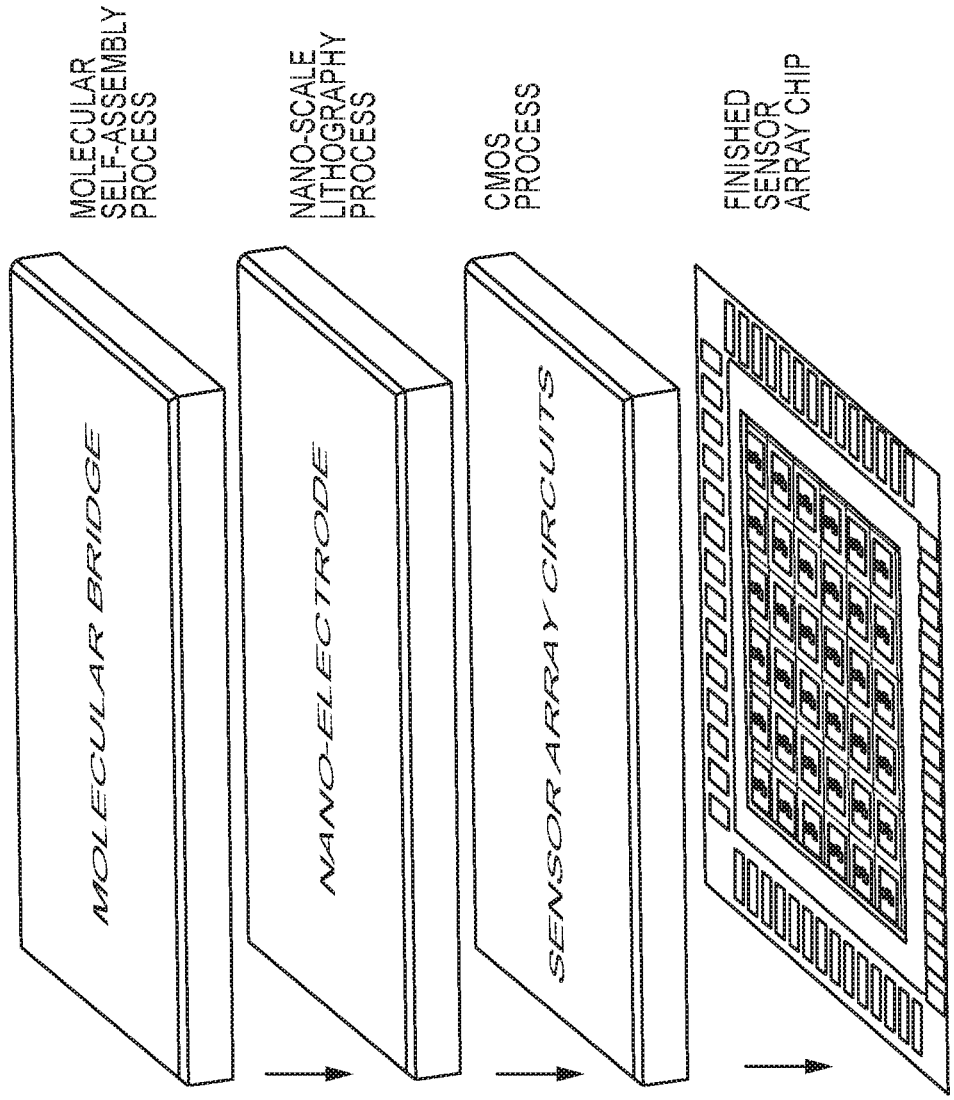
Figure 19:
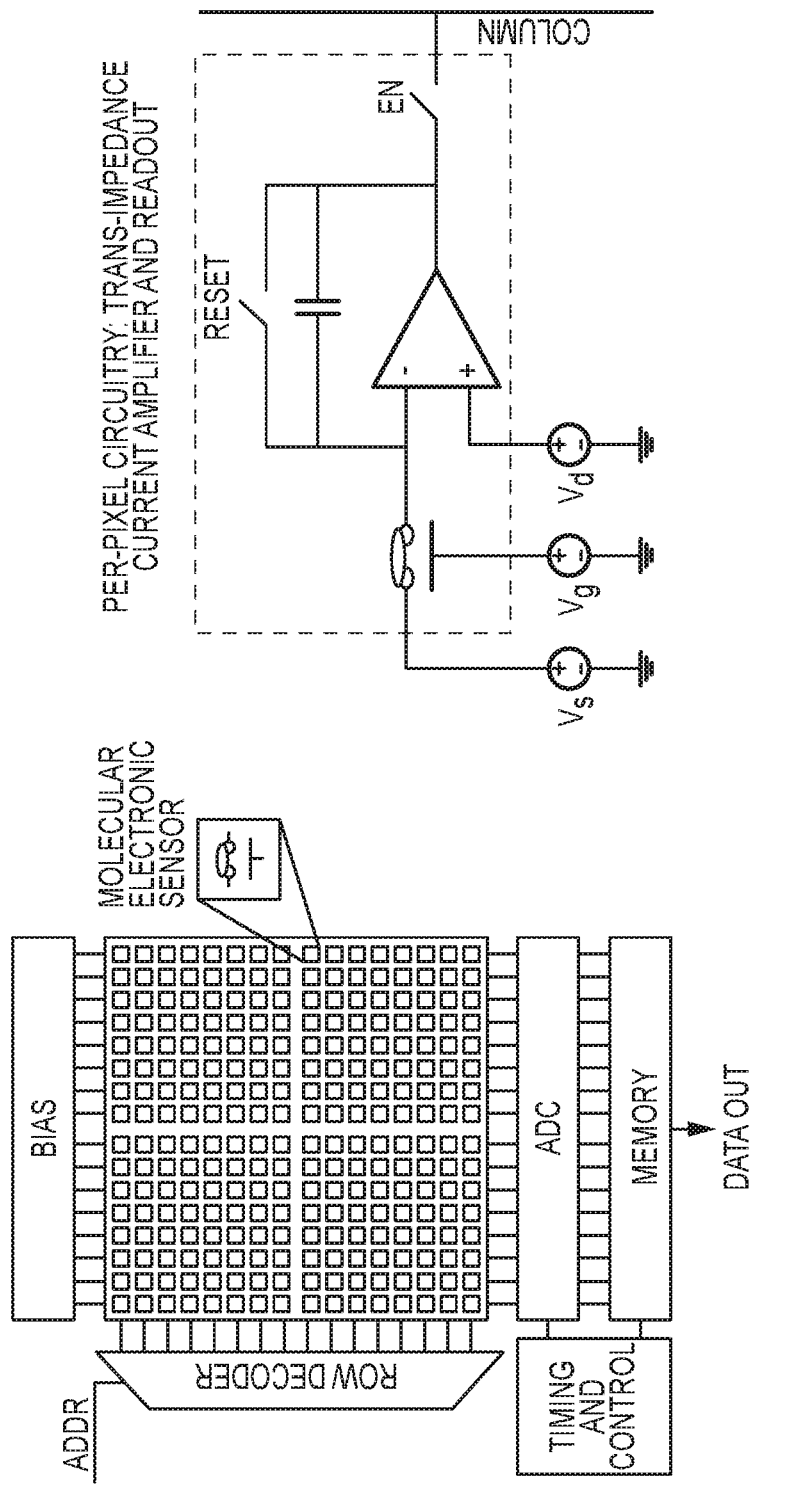
Figure 20:
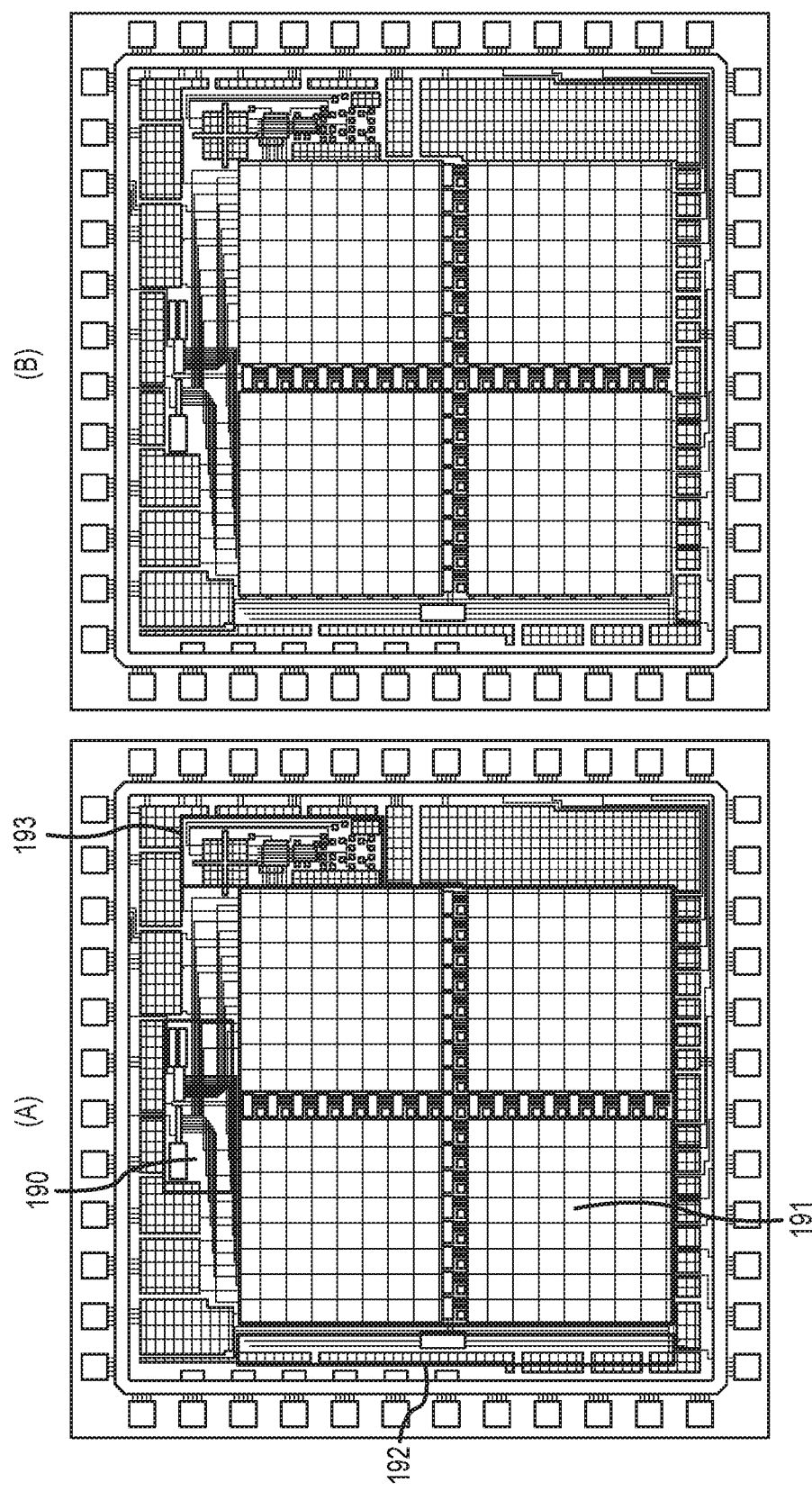
Figure 21:
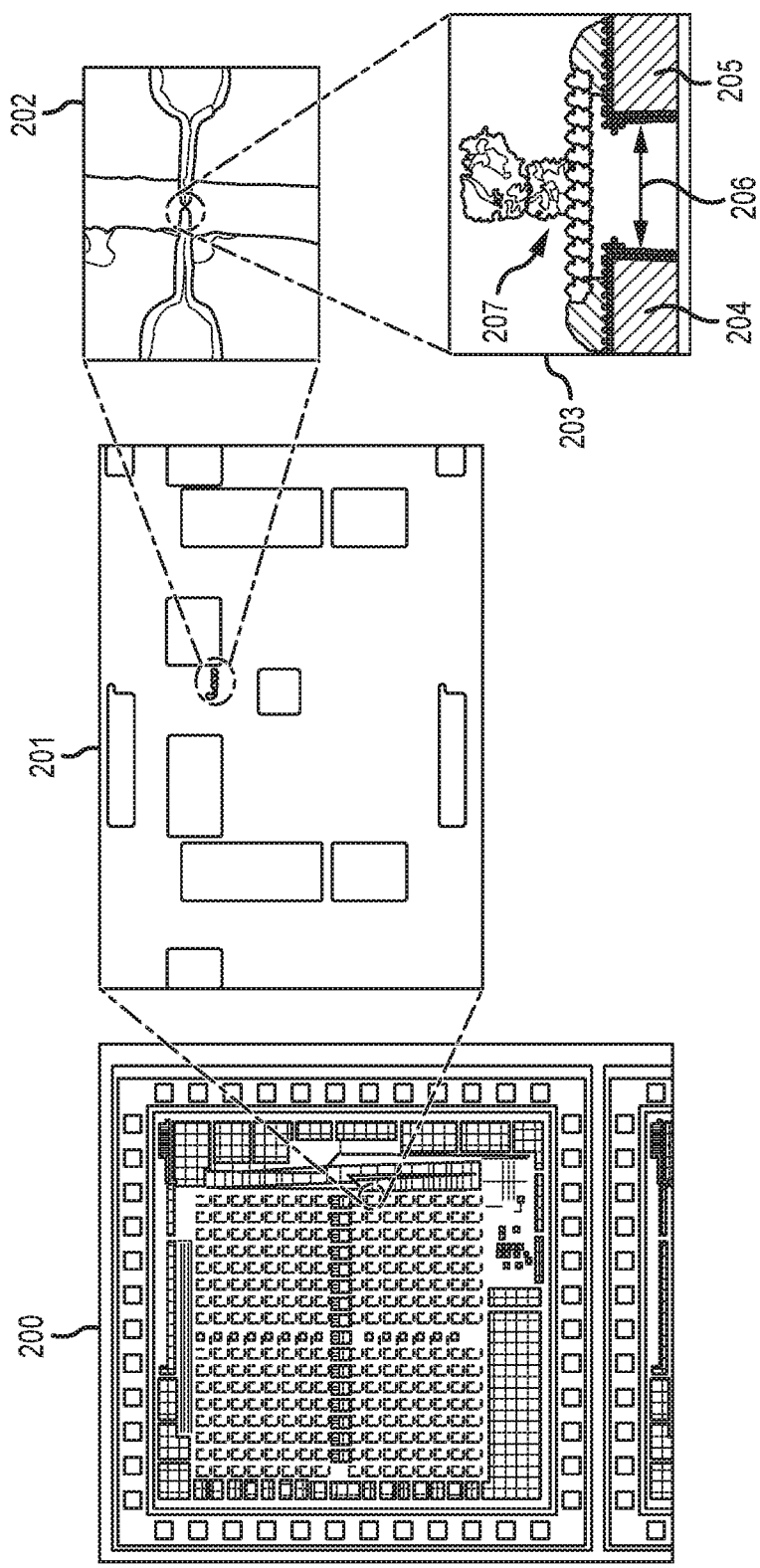
Figure 22:
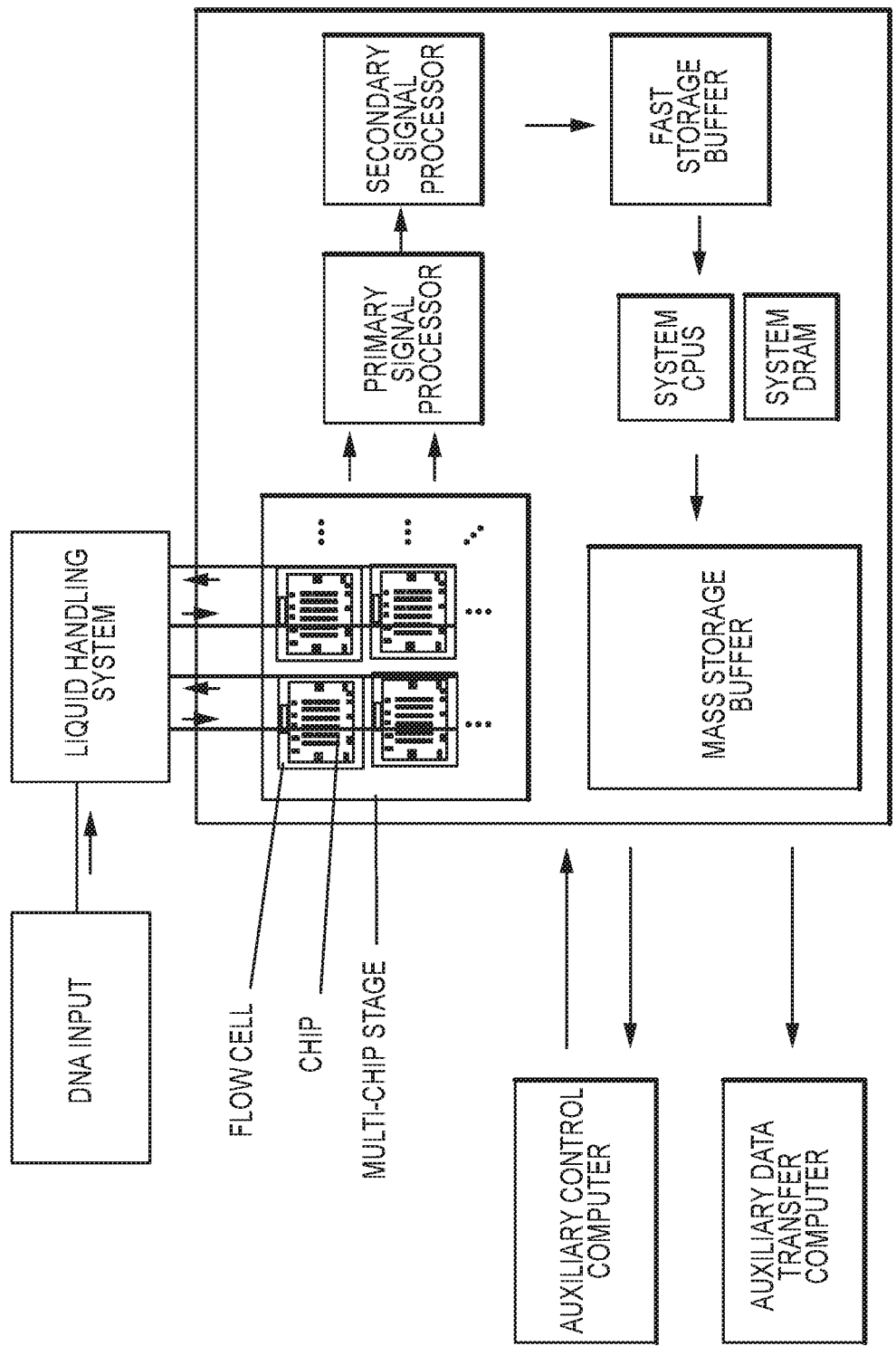
Figure 23:
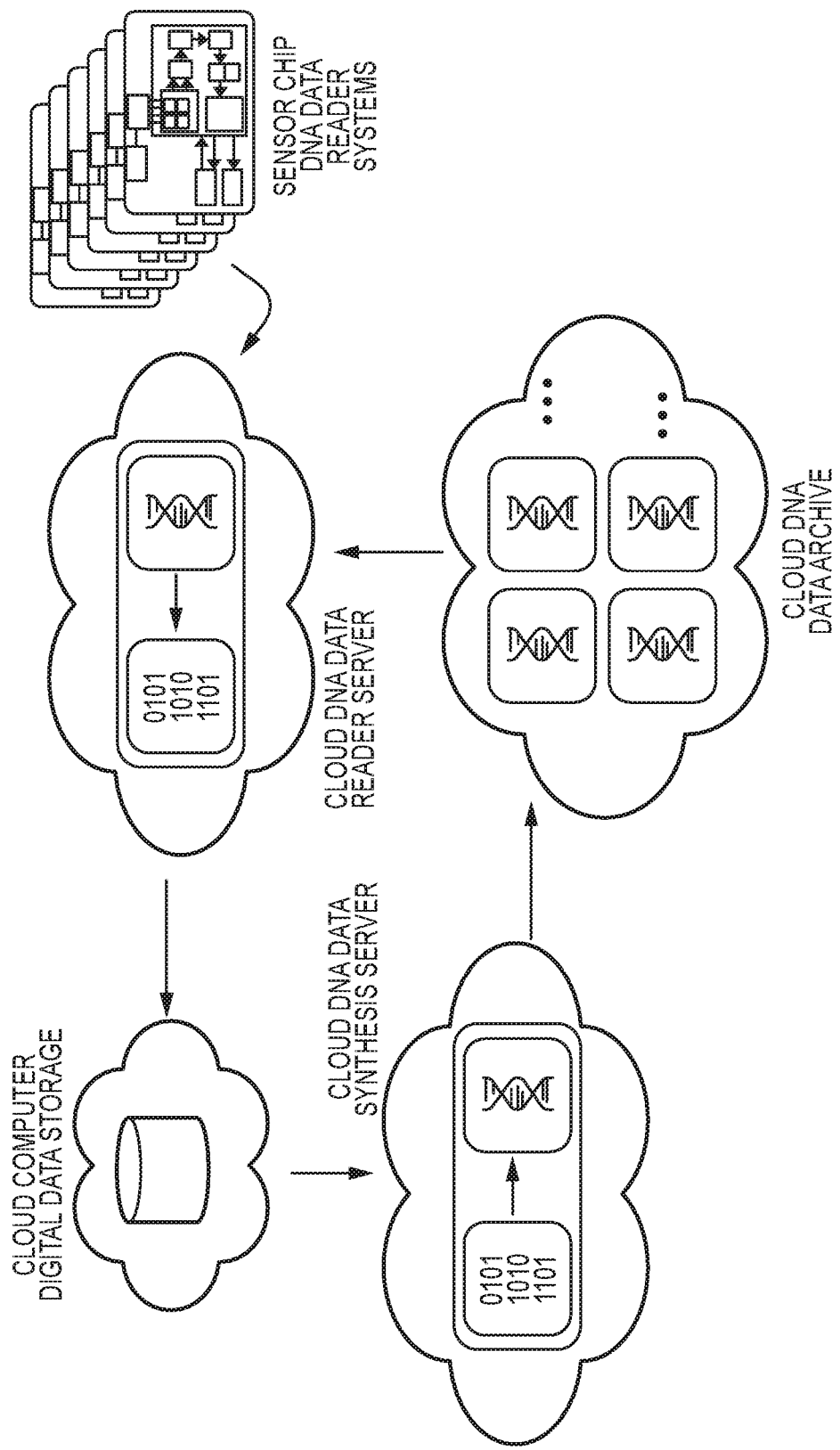
Figure 24:
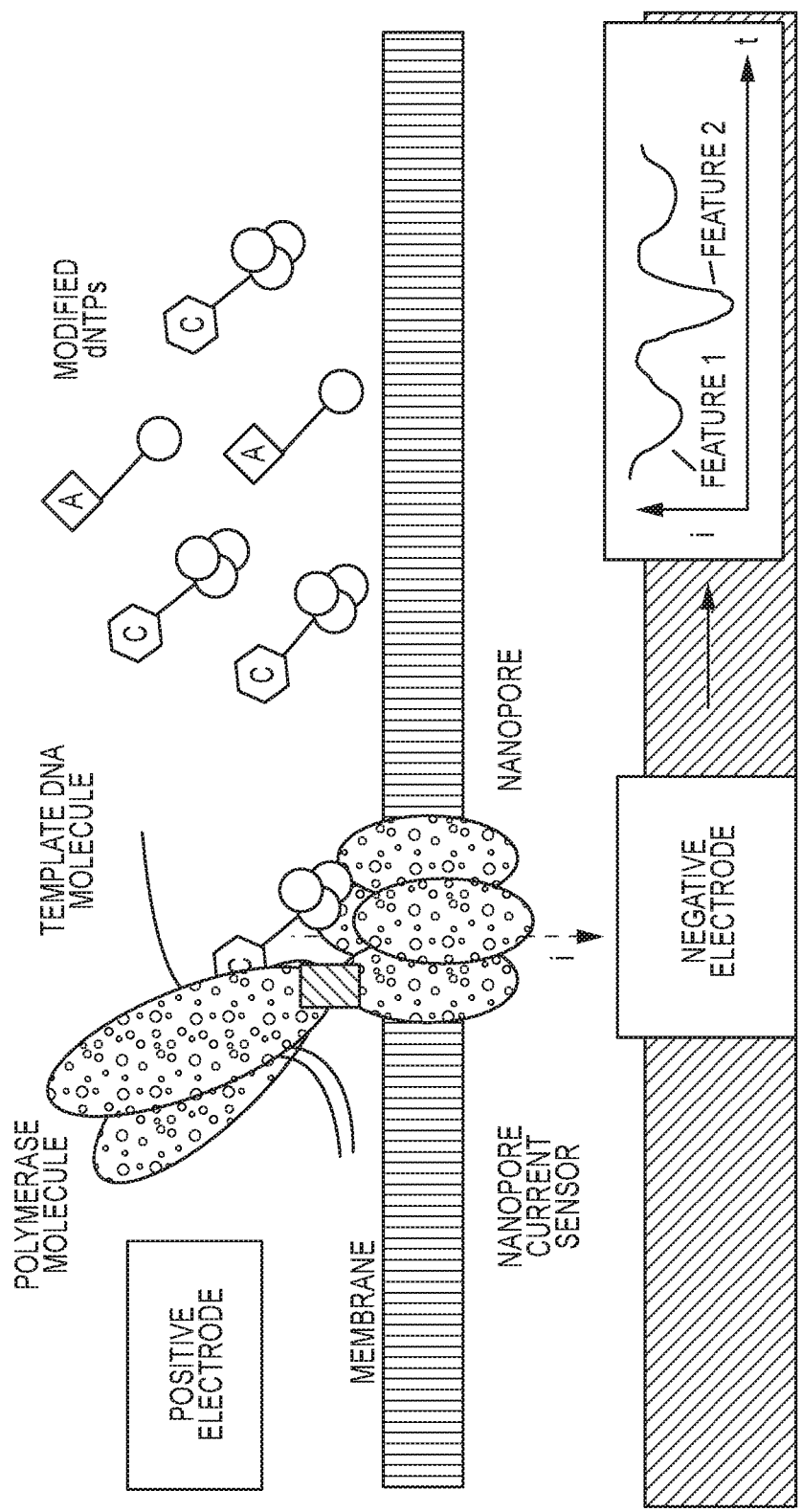
Figure 25:
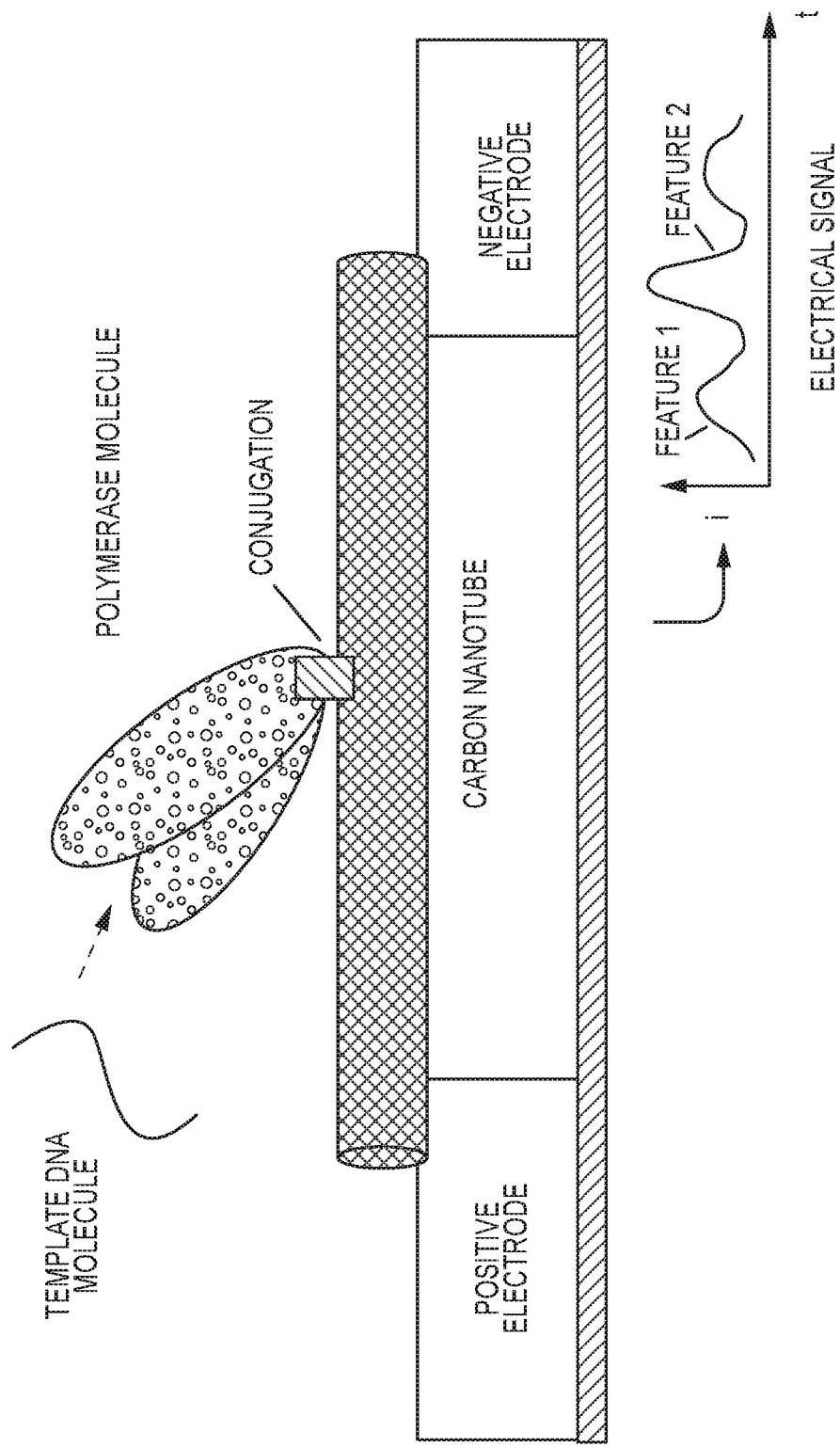
Figure 26:
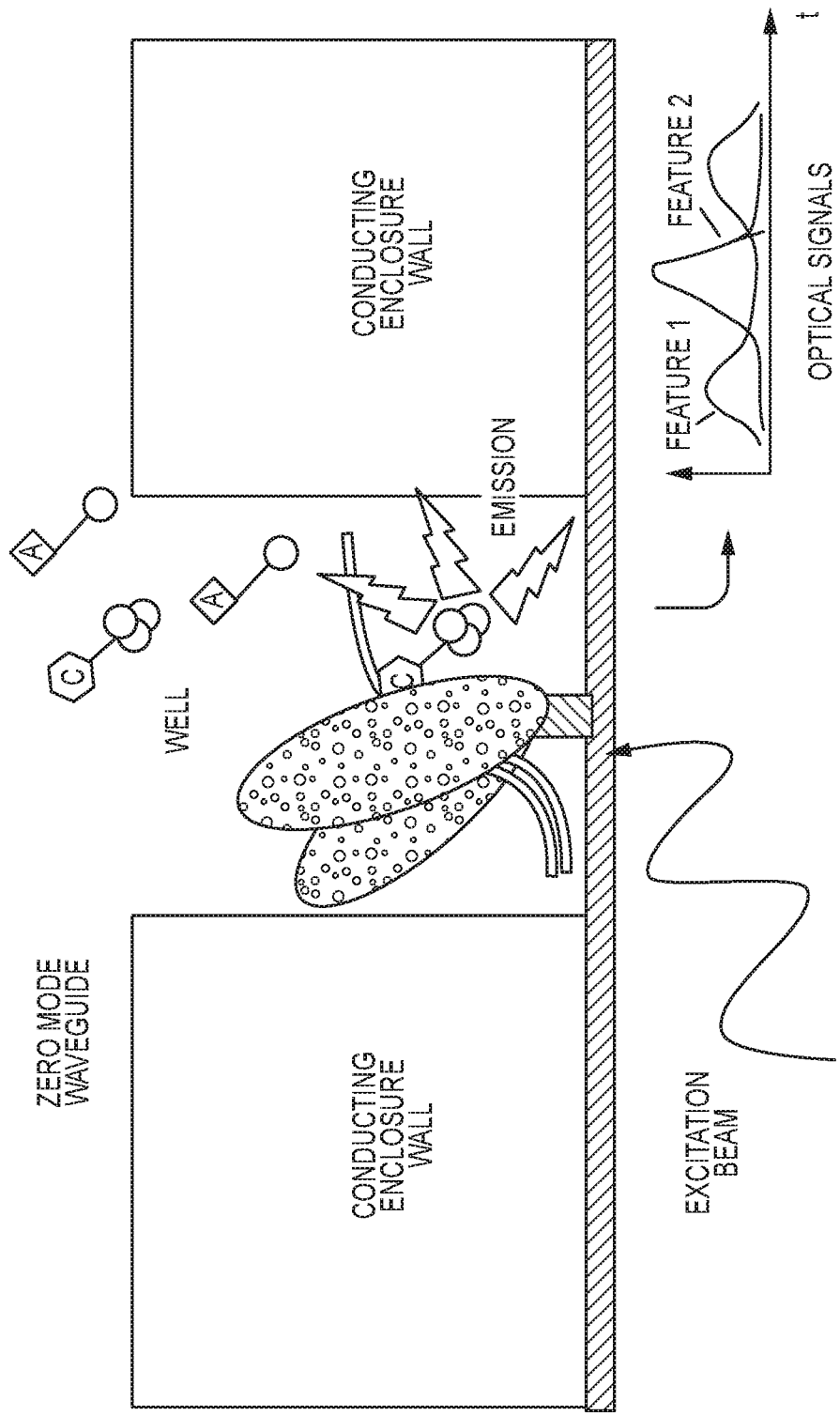

FIG. 4 illustrates embodiments of binary data encoding schemes (BES) for use with DNA where BES1 encodes a 32-bit word (00101001100111001111101000101101) using 2 bits of data into 1 DNA letter as shown by the DNA sequence ACGCGCTATTGGAGTC (SEQ ID NO:5). BES2 is the encoding of two binary digits into two bases in the word (00101001100111001111101000101101) into 2 bases of DNA (one DNA letter per one binary bit) in the sequence AACACAACCAACCCCAACCCCCACAAACACCAC (SEQ ID NO:5). BES3 encodes two binary digits into two runs of bases, AA and CCC where the digits 00101001100111001111101000101101 as represented by the nucleic acid sequence AAAACCCAAC CCAAAACCCC CCAAAACCCC CCCCCAAAAC CCCCCCCCCC CCCCAACCCA AAAAACCCAA CCCCCCAACC C (SEQ ID NO:7). BES5 illustrates the use of one DNA or modified base per 3-bits of data where the digits 00101001100111001111101000101101 are represented by the nucleic acid sequence CGTCWTZGCTT (SEQ ID NO:8);

FIG. 5 illustrates examples of DNA physical and logical structures for DNA molecules used for digital data storage;

FIG. 6 illustrates embodiments of various DNA synthesis processes capable of producing many distinct sequences within molecular replicates of each sequence, wherein N sequences with M synthesis start sites are provided per sequence;

FIG. 7 illustrates an embodiment of a molecular electronic sensing circuit in which a bridge molecule completes an electrical circuit and an electrical circuit parameter is measured versus time, wherein variations in the measured parameter comprise signals corresponding to interactions of the bridge molecule with other interacting molecules in the environment;

FIG. 8 illustrates an embodiment of a polymerase-based molecular sensor usable as a reader of data encoded into synthetic DNA molecules. A sensor comprising a polymerase produces distinguishable signals in a monitored electrical parameter corresponding to distinct DNA molecular features, wherein such features can be used to encode information into synthetic DNA molecules, which in turn can be read by the sensor;

FIG. 9 illustrates an embodiment of a polymerase-based molecular sensor, wherein the polymerase molecule is attached to a bridge molecule connecting source and drain electrodes, and wherein two different sequence motifs AA and CCC produce two distinguishable signals in the monitored electrical parameter of the sensor;

FIG. 10 illustrates a detailed protein structure of the Klenow Fragment of *E. coli* Polymerase I, a specific polymerase molecule of use herein in a DNA reading device;

FIG. 11 illustrates an embodiment of a molecular electronic sensor wherein a polymerase is conjugated from a specific position on the polymerase to a bridge molecule that connects between electrodes;

FIG. 12 illustrates a specific embodiment of the molecular sensor of FIG. 11, wherein the bridge molecule comprises double-stranded DNA, the polymer-bridge conjugation comprises biotin-streptavidin binding, and wherein the electrodes comprise gold-on-titanium in order to support thiol-gold bonding from the bridge molecule to each of the electrodes;

FIG. 13 illustrates an embodiment of a nano-electrode test chip and test set-up used in basic sensor experiments herein;

FIG. 14 illustrates an embodiment of metal nano-electrodes further comprising gold nano-dot contacts, which was used in various sensor experiments;

FIG. 15 illustrates experimental current traces obtained by processing homopolymer sequences of A, T, C and G;

FIG. 16 illustrates experimental data produced by the sensor of FIG. 12 in which specific sequence motifs of poly-A and poly-C are shown to produce distinguishable signals, demonstrating potential to encode binary data illustrated by the nucleic acid sequence AAAAAAAAAA AAAAAAAAAA CCCAAAAAAA AAAAAAAAAA AAAAAAAAAA AAA (SEQ ID NO:10);

FIG. 17 illustrates a relationship between physical DNA structure and the logical structure of a DNA data storage molecule that comprises suitable adaptors, a primer segment, buffer segments, and a data payload segment;

FIG. 18 illustrates an embodiment of a fabrication stack used to place DNA reader sensors on a chip for a low-cost massively parallel configuration;

FIG. 19 illustrates conceptual architecture for a chip-based array of polymerase sensors and an exemplary single pixel circuit comprising a trans-impedance amplifier;

FIG. 20 illustrates an embodiment of a completed, annotated chip design, and an optical microscope image of the fabricated chip, for an embodiment of the pixel array chip of FIG. 19, having an array of 256 pixels;

FIG. 21 illustrates a representation of an electron microscope image of the fabricated chip of FIG. 20, including insets of the nano-electrode with a polymerase molecular complex in position;

FIG. 22 illustrates a schematic of an embodiment of a complete system for reading DNA data with chip-based DNA reader sensors, which is free of amplification;

FIG. 23 illustrates a schematic of an embodiment of a cloud-based DNA data archival storage system in which a multiplicity of the DNA reading system of FIG. 22 are aggregated to provide the data reader server, and in which the system is free of amplification;

FIG. 24 illustrates an alternative embodiment of a DNA data reader sensor comprising a nanopore ion current sensor that produces distinguishable signal features in the nanopore ion current while processing DNA;

FIG. 25 illustrates an embodiment of a DNA data reader sensor comprising a polymerase complexed to a carbon nanotube molecular wire spanning positive and negative electrodes, which produces distinguishable signal features in the measured current passing through the carbon nanotube; and FIG. 26 illustrates an embodiment of a zero mode waveguide sensor complexed with a single polymerase, shown in cross section, which produces distinguishable optical signals corresponding to DNA features.

DETAILED DESCRIPTION

In various embodiments, methods, apparatus and systems are disclosed that utilize DNA molecules as a general purpose means of digital information storage without amplification of the DNA. In various aspects, the physical DNA does not require amplification in any aspect of the entire information storage system or in any specific subsystems of the information storage system herein. Amplification processes can impose burdens of cost, time, complexity, performance variability, and other limitations to a DNA information storage system. Further, amplification is incompatible with DNA comprising modified bases. Therefore, methods, apparatus, and systems for DNA information storage in accordance with the present disclosure are configured to avoid DNA amplification.

In various embodiments, a DNA data storage system utilizing DNA molecules as a general purpose means of digital information storage is disclosed. In certain aspects, a system for digital information storage comprises a DNA reading device, an information encoder/decoder algorithm, and a DNA writing device. In various aspects, the system further comprises a subsystem for managing physical DNA molecules to support data archival operations. The interrelation of these elements and their co-optimization are disclosed.

In various embodiments, a data reader for a DNA data storage system is disclosed. In various aspects, a DNA reading device comprises a sensor that extracts information from a single DNA molecule, thus not requiring DNA amplification. The sensor may be deployed in a chip-based format. In various examples, data reading systems that support such a chip-based sensor device are disclosed.

Definitions

As used herein, the term "DNA" may refer not only to a biological DNA molecule, but also to fully synthetic versions, made by various methods of synthetic chemistry, such as nucleotide phosphoramidite chemistry, or by serial ligation of DNA oligomers, and also to forms made with chemical modifications present on the bases, sugar, or backbone, of which many are known to those skilled in nucleic acid biochemistry, including methylated bases, adenylated bases, other epigenetically marked bases, or also including non-standard or universal bases, such as inosine or 3-nitropyrrole, or other nucleotide analogues, or ribobases, or abasic sites, or damaged sites, and also including such DNA analogues as Peptide Nucleic Acids (PNA), Locked Nucleic Acids (LNA), Xeno Nucleic Acids (XNA) (a family of sugar-modified forms of DNA, including Hexitol Nucleic Acid (HNA)), Glycol Nucleic Add (GNA), etc., and also including the biochemically similar RNA molecule along with synthetic RNA and modified forms of RNA. All these biochemically closely related forms are implied by the use of the term DNA, in the context of referring to the data storage molecule used in a DNA storage system, including a template single strand, a single strand with oligomers bound thereon, double-stranded DNA, and double strands with bound groups such as groups to modify various bases. In addition, as used herein, the term DNA may refer to the single-stranded forms of such molecules, as well as double helix or double-stranded forms, including hybrid duplex forms, including forms that containing mismatched or non-standard base pairings, or non-standard helical forms such as triplex forms, as well as molecules that are partially double-stranded, such as a single-stranded DNA bound to an oligonucleotide primer, or a molecule with a hairpin secondary structure. In various embodiments, DNA refers to a molecule comprising a single-stranded DNA component having bound oligonucleotide segments and/or perturbing groups that can act as the substrate for a probe molecule, such as a polymerase, to process, and in doing so, generate distinguishable signals in a monitored electrical parameter of a molecular sensor.

DNA sequences as written herein, such as GATTACA, refer to DNA in the 5' to 3' orientation, unless specified otherwise. For example, GATTACA as written herein represents the single-stranded DNA molecule 5'-G-A-T-T-A-C-A-3'. In general, the convention used herein follows the standard convention for written DNA sequences used in the field of molecular biology.

As used herein, the term "oligonucleotide" or "binding oligonucleotide" refers to a short segment of DNA, or analog forms described above, having a length in the range of 3 to 100 bases, or 5 to 40 bases, or 10 to 30 bases, which can hybridize with a complementary sequence contained in a template strand. Such hybridization may be through perfect Watson-Crick base-paring matches, or may involve mismatches or nonstandard base pairings.

As used herein, the term "probe molecule" refers to a molecule electrically wired between two electrodes in a pair of spaced apart electrodes in a molecular sensor, capable of interacting with molecules in the environment around the sensor to provide perturbations in a monitored electrical parameter of the molecular sensor relating to the molecular interactions. A probe molecule herein may comprise a polymerase molecule, or any other processive enzyme such as a helicase or exonuclease. In a molecular sensor herein used as a DNA reading device, a probe molecule may be conjugated to a bridge molecule that is directly wired across two spaced apart electrodes in a pair of electrodes by direct bonds between the bridge molecule and the electrodes.

As used herein, the term "polymerase" refers to an enzyme that catalyzes the formation of a nucleotide chain by incorporating DNA or DNA analogues, or RNA or RNA analogues, against a template DNA or RNA strand. The term polymerase includes, but is not limited to, wild-type and mutant forms of DNA polymerases, such as Klenow, E. coli Pol I, Bst, Taq, Phi29, and T7, wild-type and mutant forms of RNA polymerases, such as T7 and RNA Pol I, and wild-type and mutant reverse transcriptases that operate on an RNA template to produce DNA, such as AMV and MMLV. A polymerase is a choice for a probe molecule in a molecular sensor herein usable as a DNA reader.

As used herein, a "bridge molecule" refers to a molecule bound between two spaced-apart electrodes in a pair of electrodes, to span the electrode gap between the two and complete an electrical circuit of a molecular sensor. In various embodiments, a bridge molecule has roughly the same length as the electrode gap, such as 1 nm to 100 nm, or in some cases, about 10 nm. Bridge molecules for use herein may comprise double-stranded DNA, other analog DNA duplex structures, such as DNA-RNA, DNA-PNA or DNA-LNA or DNA-XNA duplex hybrids, peptides, protein alpha-helix structures, antibodies or antibody Fab domains, graphene nanoribbons or carbon nanotubes, silicon nanowires, or any other of a wide array of molecular wires or conducting molecules known to those skilled in the art of molecular electronics. A bridge molecule herein may be described as having a "first" and "second" end, such as a base at or near the 3' end and a base at or near the 5' end of a DNA molecule acting as a bridge molecule. For example, each end may be chemically modified such that the first end of a bridge molecule bonds to a first electrode and the second end of a bridge molecule bonds to a second electrode in a pair of spaced-apart electrodes. This nomenclature aids in visualizing a bridge molecule spanning an electrode gap and bonding to each electrode in a pair of spaced-apart electrodes. In various embodiments, the first and second ends of a bridge molecule may be chemically modified so as to provide for self-assembly between the bridge molecule and a probe molecule such as a polymerase, and/or between the bridge molecule and one or both electrodes in a pair of electrodes. In a non-limiting example, the ends of a bridge molecule are bonded to each of two electrodes in a pair of spaced apart electrodes by thiol (—SH)-gold bonds.

As used herein, the term "sensor molecular complex" or "sensor probe complex" refers to the combination of a probe molecule and a bridge molecule, with the two molecules conjugated together, and the assemblage wired into the sensor circuit, or any combination of more than two molecules that together are wired into the sensor circuit.

As used herein, the term "dNTP" refers to both the standard, naturally occurring nucleoside triphosphates used in biosynthesis of DNA (i.e., dATP, dCTP, dGTP, and dTTP), and natural or synthetic analogues or modified forms of these, including those that carry base modifications, sugar modifications, or phosphate group modifications, such as an alpha-thiol modification or gamma phosphate modifications, or the tetra-, penta-, hexa- or longer phosphate chain forms, or any of the aforementioned with additional groups conjugated to any of the phosphates, such as the beta, gamma or higher order phosphates in the chain. In general, as used herein, "dNTP" refers to any nucleoside triphosphate analogue or modified form that can be incorporated by a polymerase enzyme as it extends a primer, or that would enter the active pocket of such an enzyme and engage transiently as a trial candidate for incorporation.

As used herein, "buffer," "buffer solution" and "reagent solution" refers to a solution which provides an environment in which a molecular sensor can operate and produce signals from supplied DNA templates. In various embodiments, the solution is an aqueous solution, which may comprise dissolved, suspended or emulsified components such as salts, pH buffers, divalent cations, surfactants, blocking agents, solvents, template primer oligonucleotides, other proteins that complex with the polymerase of the sensor, and also possibly including the polymerase substrates, i.e., dNTPs, analogues or modified forms of dNTPs, and DNA molecule substrates or templates. In non-limiting examples, a buffer is used to hydrate and suspend DNA molecules that have been left in a lyophilized state in a DNA information library, in order to provide the DNA to a DNA reader for decoding of stored information.

As used herein, "binary data" or "digital data" refers to data encoded using the standard binary code, or a base 2 {0,1} alphabet, data encoded using a hexadecimal base 16 alphabet, data encoded using the base 10 {0-9} alphabet, data encoded using ASCII characters, or data encoded using any other discrete alphabet of symbols or characters in a linear encoding fashion.

As used herein, "digital data encoded format" refers to a series of binary digits, or other symbolic digits or characters that come from the primary translation of DNA sequence features used to encode information in DNA, or the equivalent logical string of such classified DNA features. In some embodiments, information to be archived as DNA may be translated into binary data, or may exist initially as binary data, and then this data may be further encoded with error correction and assembly information, into the format that is directly translated into the code provided by the distinguishable DNA sequence features. This latter association is the primary encoding format of the information. Application of the assembly and error correction procedures is a further, secondary level of decoding, back towards recovering the source information.

As used herein, "distinguishable DNA sequence features" means those features of a data-encoding DNA molecule that, when processed by a molecular sensor, such as one comprising a polymerase, produces distinct signals corresponding to the encoded information. Such features may be, for example, different bases, different modified bases or base analogues, different sequences or sequence motifs, or combinations of such to achieve features that produce distinguishable signals when processed by a sensor polymerase.

As used herein, a "DNA sequence motif" refers to either a specific letter (base) sequence, or a pattern, representing any member of a specific set of such letter sequences. For example, the following are sequence motifs that are specific letter sequences: GATTACA, TAC, or C. In contrast, the following are sequence motifs that are patterns: G[A/T]A is a pattern representing the explicit set of sequences {GAA, GTA}, and G[2-5] is a pattern referring to the set of sequences {GG, GGG, GGGG, GGGGG}. The explicit set of sequences is the unambiguous description of the motif, while pattern shorthand notations such as these are common compact ways of describing such sets. Motif sequences such as these may be describing native DNA bases, or may be describing modified bases, in various contexts. In various contexts, the motif sequences may be describing the sequence of a template DNA molecule, and/or may be describing the sequence on the molecule that complements the template.

As used herein, "sequence motifs with distinguishable signals," in the cases of patterns, means that there is a first motif pattern representing a first set of explicit sequences, and any of said sequences produces the first signal, and there is a second motif pattern representing a second set of explicit sequences, and any of said sequences produces the second signal, and the first signal is distinguishable from the second signal. For example, if motif G[A/T]A and motif G[3-5] produce distinguishable signals, it means that any of the set {GAA, GTA} produces a first signal, and any of the set {GGG, GGGG, GGGGG} produces a second signal that is distinguishable from the first signal.

As used herein, "distinguishable signals" refers to one electrical signal from a sensor being discernably different than another electrical signal from the sensor, either quantitatively (e.g., peak amplitude, signal duration, and the like) or qualitatively (e.g., peak shape, and the like), such that the difference can be leveraged for a particular use. In a non-limiting example, two current peaks versus time from an operating molecular sensor are distinguishable if there is more than about a $1 \times 10^{-10}$ Amp difference in their amplitudes. This difference is sufficient to use the two peaks as two distinct binary bit readouts, e.g., a 0 and a 1. In some instances, a first peak may have a positive amplitude, e.g., from about $1 \times 10^{-10}$ Amp to about $20 \times 10^{-10}$ Amp amplitude, whereas a second peak may have a negative amplitude, e.g., from about 0 Amp to about $-5 \times 10^{-10}$ Amp amplitude, making these peaks discernably different and usable to encode different binary bits, i.e., 0 or 1.

As used herein, a "data-encoding DNA molecule," or "DNA data encoding molecule," refers to a DNA molecule synthesized to encode data within the DNA's molecular structure, which can be retrieved at a later time.

As used herein, "reading data from DNA" refers to any method of measuring distinguishable events, such as electrical signals or other perturbations in a monitored electrical parameter of a circuit, which correspond to molecular features in a synthetic DNA molecule that were built into the synthetic DNA to encode information into the DNA molecule.

As used herein, "electrodes" refer to nano-scale electrical conductors (more simply, "nano-electrodes"), disposed in pairs and spaced apart by a nanoscale-sized electrode gap between the two electrodes in any pair of electrodes. In various embodiments, the term "electrode" may refer to a source, drain or gate. A gate electrode may be capacitively coupled to the gap region between source and drain electrodes, and comprise a "buried gate," "back gate," or "side gate." The electrodes in a pair of spaced-apart electrodes may be referred to specifically (and labeled as such in various drawing figures) as the "source" and "drain" electrodes, "positive" and "negative" electrodes, or "first" and "second" electrodes. Whenever electrodes in any of the drawing figures herein are labeled "positive electrode" and "negative electrode," it should be understood the polarity indicated may be reversed, (i.e., the labels of these two elements in the drawings can be reversed), unless indicated otherwise, (such as an embodiment where electrons may be flowing to a negative electrode). Nano-scale electrodes in a pair of electrodes are spaced apart by an electrode gap measuring about 1 nm to 100 nm, and each electrode may have other critical dimensions, such as width, height, and length, also in this same nanoscale range. Such nano-electrodes may be composed of a variety of materials that provide conductivity and mechanical stability. They may be comprised of metals, or semiconductors, for example, or of a combination of such materials. Metal electrodes may comprise, for example, titanium, chromium, platinum, or palladium. Pairs of spaced-apart electrodes may be disposed on a substrate by nano-scale lithographic techniques.

As used herein, the term "conjugation" refers to a chemical linkage, (i.e., bond), of any type known in the chemical arts, e.g., covalent, ionic, Van der Waals, etc. The conjugations of a probe molecule, such as a polymerase, to a bridge molecule, such as a double-stranded DNA molecule, or conjugations between a bridge molecule to an electrode or a metal deposit on an electrode, may be accomplished by a diverse array of conjugation methods known to those skilled in the art of conjugation chemistry, such as biotin-avidin couplings, thiol-gold couplings, cysteine-maleimide couplings, gold binding peptides or material binding peptides, click chemistry coupling, Spy-SpyCatcher protein interaction coupling, or antibody-antigen binding (such as the FLAG peptide tag/anti-FLAG antibody system), and the like. Conjugation of a probe molecule to each electrode in a pair of spaced-apart electrodes comprises an "electrical connection" or the "electrical wiring" of the probe molecule into a circuit that includes the probe molecule and the pair of electrodes. In other words, the probe molecule is conjugated to each electrode in a pair of electrodes to provide a conductive pathway between the electrodes that would be otherwise be insulated from one another by the electrode gap separating them. A conductive pathway is provided by electron delocalization/movement through the chemical bonds of the probe molecule, such as through C—C bonds. Conjugation sites engineered into a probe molecule, such as a polymerase, by recombinant methods or methods of synthetic biology, may in various embodiments comprise any one of a cysteine, an aldehyde tag site (e.g., the peptide motif CxPxR), a tetracysteine motif (e.g., the peptide motif CCPGCC), and an unnatural or non-standard amino acid (NSAA) site, such as through the use of an expanded genetic code to introduce a p-acetylphenylalanine, or an unnatural crosslinkable amino acid, such as through the use of RNA- or DNA-protein cross-link using 5-bromouridine, (see Gott, J. M., et al., *Biochemistry*, 30 (25), 6290-6295 (1991)).

As used herein, the term "amplification" refers to molecular biology methods that make one or more copies of a DNA molecule, and that, when performed on a pool of suitable DNA molecules collectively achieve copying of the pool. Such copying methods include converting a DNA molecule to RNA, or vice-versa. Such methods include all forms of exponential copying, such as PCR, in which the number of copies produced from an initial set of templates grows exponentially with cycle number or time. This includes the many variants or extensions of PCR known to those skilled in molecular biology. These include, for example, isothermal methods and rolling circle methods and methods that rely on nicking or recombinase to create priming sites, or amplification methods such as LAMP, DMA or RPA. Such methods also include linear amplification methods, in which the number of copies produced grows linearly with cycle number or time, such as T7 amplification or using a single primer with thermocycling or with isothermal means of reinitiating polymerase extension of a primer. This includes use of degenerate primers or random primers. Amplification as used herein also explicitly includes the special case of creation of the complementary strand of a single-stranded template, when such complementary strand is also used to represent the stored information in the processes of data storage—for example, in the context of readers that read both strands in the process of recovering the stored information. Such a complementary strand may remain in the double-stranded physical conformation with its complement in the storage DNA molecule, or may exist separated from its complementary strand in the storage system, in either case this constitutes amplification, i.e. copying, of the primary template, for information storage purposes. This is distinguished from the case where a DNA reader creates a complementary strand in the course reading data from a single-stranded template, which is not amplification as the term is used herein—for in this case, such a strand is merely a byproduct of the reading process, and not itself used as an information encoding molecule from which information is potentially extracted. DNA readers that create such byproduct strands include the polymerase molecular electronics readers described herein and illustrated in FIGS. 8-12 and 24-26. As used herein, such DNA reader systems are amplification-free.

Figure 1:
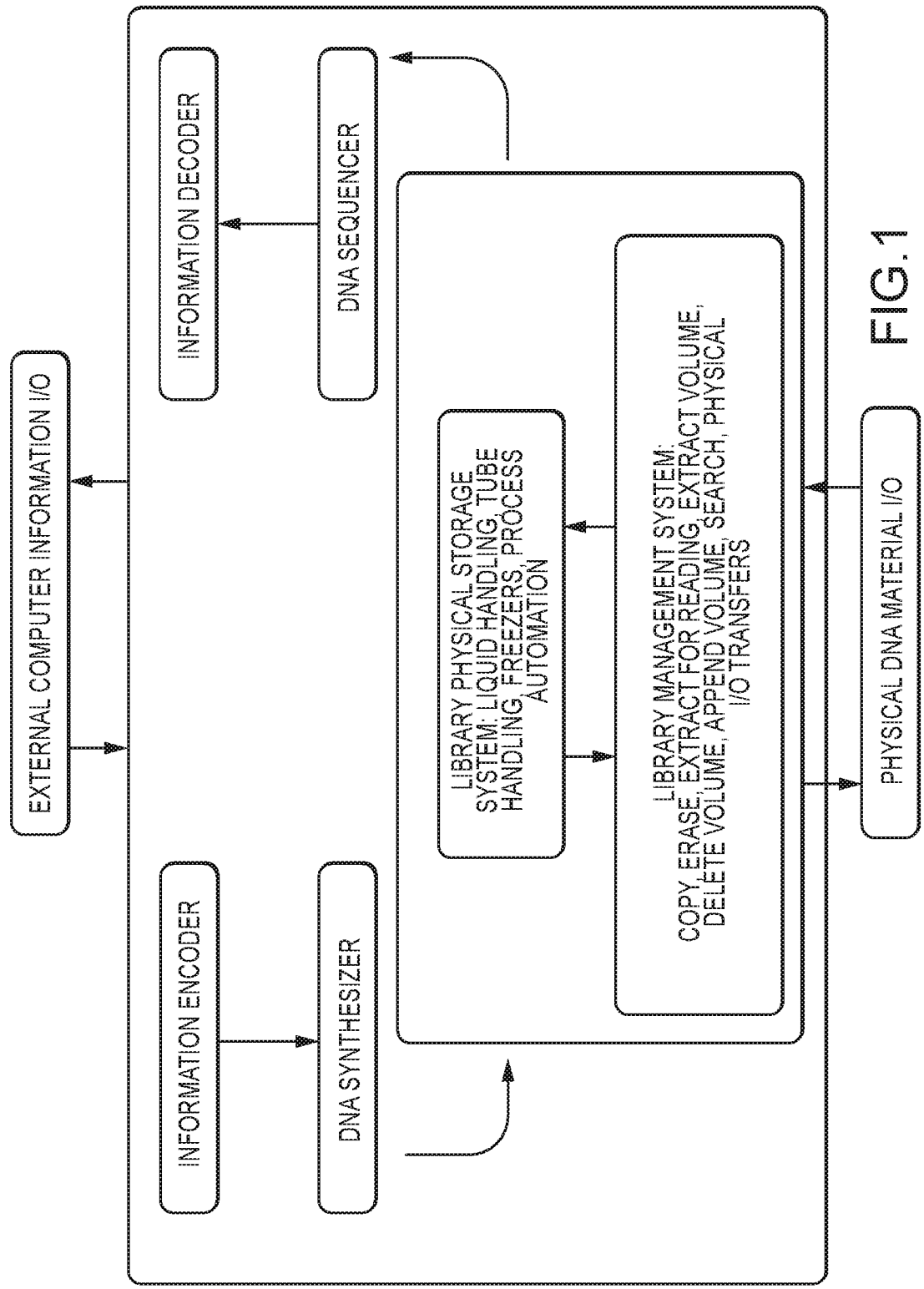
FIG. 1 illustrates an embodiment of an amplification-free DNA digital data storage system.

Amplification-Free DNA Digital Data Storage:

General aspects of amplification-free DNA data storage methods, apparatus and systems, in accordance with the present disclosure and usable for archiving and later accessing stored data, are disclosed in reference to the various drawing figures:

FIG. 1 illustrates an embodiment of an amplification-free DNA information storage system in accordance with the present disclosure. As illustrated in FIG. 1, an amplification-free DNA storage system comprises an information encoder/decoder algorithm, a DNA writing device (synthesizer), a DNA reading device (sequencer), and a library management subsystem for managing physical DNA molecules in the library physical storage to support archival operations. This example shows the major elements of a DNA storage system, including the physical system used to handle and maintain the DNA material during storage, and which carries out operations on the stored archive, such as copying. An external computer provides a high level control of the system, supplying information for storage, and receiving extracted information. Information is encoded as DNA sequences, synthesized into DNA molecules, stored, and then read, decoded and output. In addition, such a system is capable of physical I/O of the DNA archive material samples as well.

Figure 2:
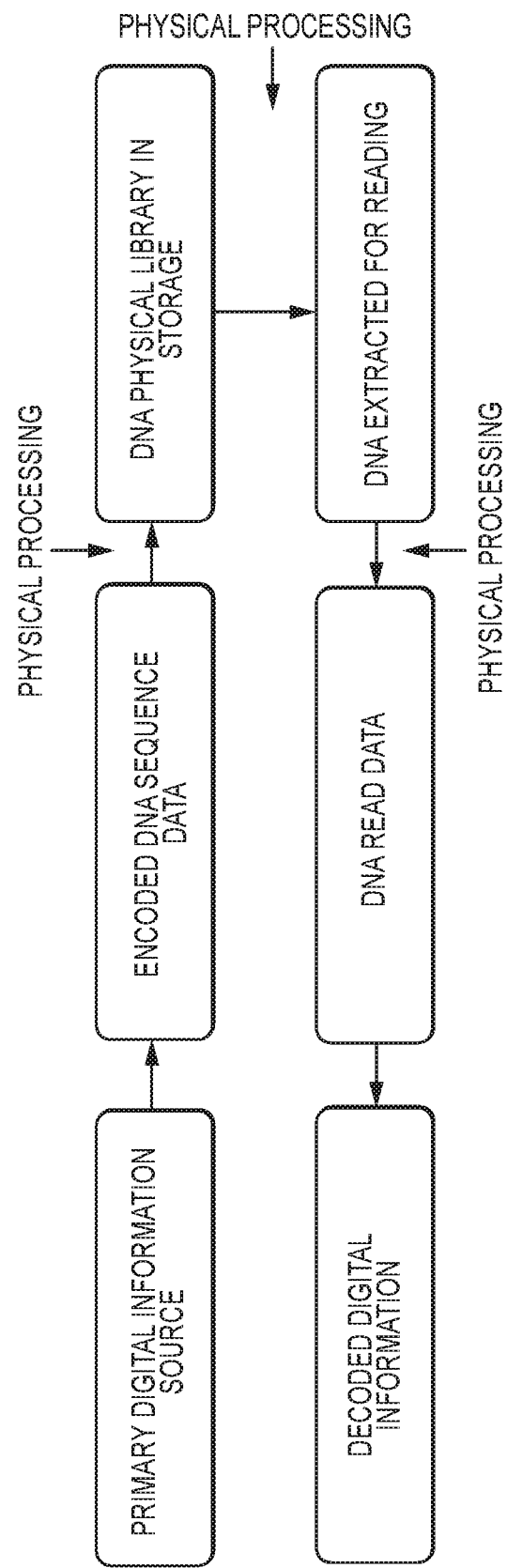
FIG. 2 illustrates a general process flow of data input and retrieval for an embodiment of an amplification-free DNA digital data storage system.

FIG. 2 illustrates primary DNA storage system information phases and processes, including the major phases of information existing in the overall system (depicted in FIG. 2 as boxes), along with the primary operations transitioning from one form to another (depicted in FIG. 2 by arrows). As shown in FIG. 2, the elements of writing, reading and library management each comprise steps of physically processing DNA molecules.

Figure 3:
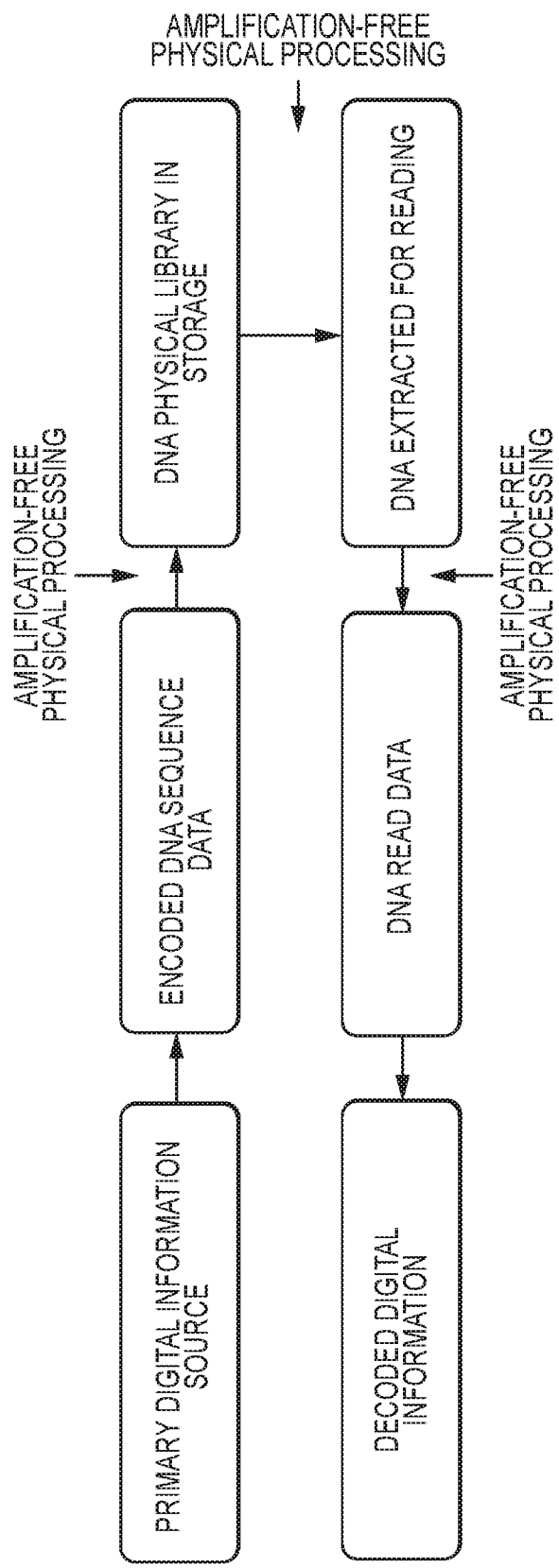
FIG. 3 illustrates a constrained process flow of data input and retrieval for an embodiment of an amplification-free DNA digital data storage system.

As indicated in FIG. 3, one aspect of the present system is that these processes (of FIG. 2) are free of any amplification of the stored DNA. That is, the DNA storage system is amplification-free. As discussed herein in more detail, various methods and apparatus provide for the amplification-free elements depicted in FIG. 3. In various embodiments, the DNA storage system is entirely amplification-free. That is, all of the processes illustrated in FIG. 2 are amplification-free. In other embodiments, a DNA storage system in accordance with the present disclosure may comprise an amplification-free element, but the system may not be entirely amplification-free overall. Nonetheless, there are still separate benefits provided by the amplification-free elements within a system that is not entirely amplification-free. Such a system that is not entirely amplification-free, but that comprises at least one amplification free process, is referred to herein as a "reduced-amplification" DNA information storage system.

Each major element of a DNA data storage system in accordance with the present disclosure is detailed herein below, including how each element of the system relates to, or involves, DNA amplification, and how the relevant amplification-free elements can be configured for a DNA data storage system.

In various aspects of the present disclosure, a DNA information storage system comprises: an encoder/decoder; a DNA writing device; and a DNA reading device.

Encoder/Decoder:

In various aspects, the encoder/decoder provides two functions: the encoder portion translates given digital/binary information or data into a specific set of DNA sequence data that are inputs to the DNA writer. Second, the decoder portion translates a given set of DNA sequences of the type provided by the DNA reader back into digital information.

FIG. 4 illustrates several binary encoding schemes (herein referred to as "BES") for converting binary data into DNA sequences. Other encoding schemes of use herein include those schemes capable of supporting error detection and error correction. In these example encoding scenarios, the originating digital data that is to be stored as DNA will typically originate as electronic binary data. In various examples, information (e.g., language, music, etc.) can first be converted to electronic binary data. This originating binary data will then be divided into segments, augmented by reassembly data, and transformed by error correcting encodings appropriate for DNA data storage to produce actual binary data payload segments, (such as exemplified in FIG. 4), which then require translation to DNA sequences for subsequent DNA synthesis to produce the physical storage molecules. As will be discussed in more detail below, a DNA logical structure comprises a data payload segment wherein specific data is encoded. In various embodiments, a data payload segment comprises the actual primary digital data being stored along with metadata for the storage method, which may comprise data related to proper assembly of such information fragments into longer strings, and/or data related to error detection and correction, such as parity bits, check sums, or other such information overhead.

Primary translation from binary to DNA sequence is what, in various embodiments, is performed by binary encoding schemes (BES), such as those exemplified in FIG. 4. These encoding schemes provide primary translation from a digital data format, such as a binary data format, to a DNA molecular sequence format, via first producing a list of distinguishable signaling features that imply corresponding DNA segments, which are assembled for the encoding DNA molecule. Choosing which BES is appropriate depends, in part, on the type of distinguishable signal features and their arrangements, (as discussed below in the context of FIG. 8 and illustrated in the inset of FIG. 8). As discussed herein, BES that comprises converting one bit of digital binary data to more than one DNA base are preferred, at least for the sake of reducing errors that would otherwise occur in both DNA writing and DNA reading.

FIG. 4 illustrates several such primary encodings, beginning with an exemplary binary data payload, a particular 32-bit word "00101001100111001111101000101101," and converting the binary data to one or more distinguishable signal features for the encoded DNA molecule. As illustrated in FIG. 4, BES1 is the encoding of 2 bits of data into 1 DNA letter, e.g., encoding 1 bit into 2 distinguishable signaling features F1 and F2, for use with a DNA reading sensor that can distinguish these features; BES2 is the encoding of two binary digits into two bases (one DNA letter per one binary bit), e.g., encoding combinations of two binary bits 00, 01, 10 and 11 into four features, F1, F2, F3 and F4, for use with a DNA reading sensor that distinguishes these features; and BES3 shows an example where the length of the sequence tract is used to encode information, which is appropriate for cases where such sequence runs produce distinguishable signals from the DNA reading sensor. BES3 encodes two binary digits into two runs of bases, AA and CCC, (one run of DNA letters per one binary bit). For example, BES3 encodes the binary strings 0, 1 and 00 into 3 distinguishable features F1, F2 and F3. BES4 and BES5 illustrate the possible use of additional DNA bases such as modified bases of base analogues, denoted here as X, Y, Z, and W. If such analogues produce distinguishable signals from the DNA reader, this can be used as in BES4 to implement a binary code using two such distinguishable analogues. BES5 uses a total of 8 distinguishable DNA letters to represent 3 bits of binary data, using DNA molecules composed of 4 native bases and 4 modified bases, to encode the eight possible I/O 3-bit states, (one DNA base or modified base per 3-bits of data). BES6 illustrates the use of sequence motifs to encode binary information, (one DNA sequence motif per one binary bit), in such a case where such motifs produce distinguishable signal traces.

Encoding schemes for use herein must have a cognate sensor, such as a polymerase-based molecular sensor, capable of distinguishing the signals of the encoding features, so that the choices of BES are directly related to the properties of the sensor in distinguishing features. Digital data formats or alphabets other than binary, such as hexadecimal, decimal, ASCII, etc., can equally well be encoded into DNA signaling features by similar schemes as the BES of FIG. 4. Schemes more sophisticated than those shown, in terms of optimal information density, such as Lempel-Ziv encoding, can highly efficiently convert and compress data from one alphabet into another. In general, for converting a binary or other digital data payload string or collection of strings into a DNA sequence string, or collection of such strings, the methods of lossless and lossy encoding or compression can be used to devise schemes for the primary conversion from input digital data payloads to DNA data payloads.

In an exemplary embodiment, a polymerase-based molecular electronics sensor produced distinguishable signals in a monitored electrical parameter of the sensor when the sensor encountered the distinguishable signaling features of oligonucleotides 5'-CCCC-3', 5'-GGGG-3', and 5'-AAAA-3', when bound to the respective reverse complement template segments F1=5'-GGGG-3', F2=5'-CCCC-3', and F3=5'-TTTT-3', presented in a synthetic DNA molecule provided in a suitable buffer to the sensor. In this embodiment, a binary encoding scheme was used wherein the bit 0 was encoded as GGGG (i.e., F1), the bit 1 was encoded as CCCC, i.e., F2, and the binary string 00 was encoded as TTTT i.e., F3. Note this encoding scheme included the encoding of 00 as TTTT, i.e., encoding as the data string 00 rather than as two consecutive data bits of 0, which would have encoded as GGGGGGGG. This encoding scheme was then used to encode an input binary data payload of "01001" into a nucleotide sequence for incorporation in the synthetic DNA molecule. The conversion to a feature sequence of F1-F2-F3-F1 began by dividing the input data string of binary data 01001 into the segments 0, 1, 00, and 1, and converting these data segments into a DNA data payload segment of the encoded DNA molecule as 5'-GGGGCCCCTTTTGGGG-3' (SEQ ID NO:3). In other embodiments, there may be "punctuation" sequence segments inserted between the distinguishable signal features, which do not alter the distinguishable features, e.g., bound oligonucleotides, which provide benefits such as accommodating special properties or constraints of the DNA synthesis chemistry, or to provide spacers for added time separation between signal features, or reduced steric hindrance, or to improve the structure of the DNA molecule. For example, if A were such a punctuation sequence, the DNA encoding sequence would become 5'-AGGGGACCCCATTTTAGGGGA-3' (SEQ ID NO:4). In general, such insertion of punctuation sequences or filler sequences may be part of the process of translating from a digital data payload to the encoding DNA sequence to be synthesized.

In various embodiments, information as binary data such as 010011100010 may be encoded using three states A, B, C, wherein 0 is encoded as A, 1 is encoded as B, and 00 is encoded as C whenever 00 occurs, (i.e., such as not to encode 00 as AA). In accordance with this scheme, the binary word 010011100010 is equivalent to the encoded form ABCBBBCABA.

In general, for converting a binary or other digital data payload string or collection of strings into a DNA sequence string or collection of such strings, many of the methods of lossless and lossy encoding or compression, e.g., those well known in computer science, can be used to devise schemes for the primary conversion of input digital data payloads to DNA sequence data payloads, as strings of distinguishable feature DNA segments, generalizing the examples of FIG. 4. In this broader context, the BES schemes exemplified in FIG. 4 illustrate the type of feature elements that could become symbols of an alphabet for data encoding, such as standard bases, modified bases, or sequence motifs or runs, provided that such elements have a cognate reader sensor.

FIG. 5 illustrates the relationships between physical DNA molecules and the digital data encoded therein. Physical DNA may exist in single-stranded or double-stranded form, depending, for example, on the details of the storage system. The sequence data payload, in the logical structure shown, represents the binary data, including error correction and addressing information, and it comprises only a portion of the sequence of the physical DNA molecule. There may be additional LEFT and RIGHT sequence segments relating to the physical handling of DNA, such as binding sites for specific complementary oligonucleotides, regions that carry other forms of commonly used binding groups useful for DNA manipulation, such as biotin sites, or segment that provide spatial separation, or sequence segments used to calibrate properties of the reading or writing systems. Since the encoder/decoder process is generally performed on data and not on physical DNA, it typically does not itself require or prescribe any form of physical amplification of DNA.

With continued reference to FIG. 5, the DNA logical structure shown is an example structure of an information-carrying DNA fragment. In this example, a PRIMER segment contains primer target/structure. Further, an L-BUF- FER segment may contain signal calibration sequence for the DNA reader, or buffering sequence prior to the DATA PAYLOAD segment, containing information storing encoded sequence and related error correction sequence such as parity bits. R-BUFFER may contain additional calibration sequence, as well as buffer sequence allowing for the probe molecule (e.g., a polymerase) to avoid getting too close to the end of the template when reading DNA. L-ADAPTER and R-ADAPTER may be sequence elements related to the storage or manipulation of the associated DNA segment, such as adapters for outer priming sites for PCR amplification, or hybridization based selection, or representing a surrounding carrier DNA for this insert, including insertion into a host organism genome as a carrier. The data payload portion of the logical structure in general may include the actual primary data being archived as well as metadata for the storage method, such as relating to the assembly of this information into larger strings, or error detection and correction.

DNA Writing Device:

In various embodiments, a DNA writing device for use herein takes a given set of input DNA sequence data and produces the DNA molecules having these sequences. For each desired sequence, multiple DNA molecules representing that sequence are produced. The multiplicity of molecules produced can be in the ranges of 10's, 100's, 1000's, millions, billions or trillions of copies of DNA molecules for each desired sequence. All of these copies representing all the desired sequences may be pooled into one master pool of molecules. It is typical of such DNA writing systems that the writing is not perfect, and if N molecules are synthesized to represent a given input sequence, not all of these will actually realize the desired sequence. For example, they may contain erroneous deletions, insertions, or incorrect or physically damaged bases. Such a system will typically rely on some primary means of synthesizing DNA molecules, such as comprising chemical reactions and a fluidic system for executing the processes on a large scale in terms of the number of distinct sequences being synthesized, (see, for example, Kosuri and Church, "Large Scale de novo DNA Synthesis: Technologies and Applications," *Nature Methods,* 11: 499-509, 2014). Non-limiting examples of methods and devices for synthesizing DNA molecules include commercial technology offered by Agilent Technologies and Twist BioScience.

FIG. 6 illustrates methods of synthesizing DNA molecules. In various embodiments, primary methods of synthesizing DNA co-synthesize many instances of the same DNA sequence without using any amplification procedures. Such methods perform a number of physically or chemically isolated reactions, wherein each isolated region includes many molecular start sites for the synthesis of each target sequence. In FIG. 6, the molecular start sites are indicated as "M" and are located, for example, on a solid support surface as shown. The distinct target sequences, "N," are produced in distinct isolated reaction regions along the surface, reacting all the start sites within the same reaction, wherein these reactions may be applied in time serially or in parallel for the different sequence targets, such as depending on the system used. These coupling reactions, e.g., from A to B to C in FIG. 6, add one or more of the desired bases to the molecules growing at the start sites of that region. This approach includes methods such as classical phosphoramidite DNA synthesis, as well as methods that may rely on enzymatic addition of bases, such as methods utilizing a terminal transferase enzyme to achieve base addition.

In various embodiments, nucleotides can be preferentially selected for incorporation in nucleotide sequences based on their ease of synthesis in the writing process that forms molecules, reduced propensity to form secondary structure in the synthesized molecules, and/or ease in reading during the data decoding process. In various aspects, bad writing motifs and bad reading motifs are avoided in the selection of nucleotides for incorporation into nucleotide sequences, with a focus on incorporating segments in the nucleotide sequence that will produce mutually distinguishable signals when that nucleotide sequence is read to decode the encoded information. For example, in reading a nucleotide sequence, A and T are mutually distinguishable, C and G are mutually distinguishable, A, C and G are mutually distinguishable, AAA and TT are mutually distinguishable, A, GG and ATA are mutually distinguishable, and C, G, AAA, TTTT, and GTGTG are mutually distinguishable. These and many other sets of nucleotide and nucleotide segments provide mutually distinguishable signals in a reader, and thus can be considered for incorporation in a nucleotide sequence when encoding a set of information into a nucleotide sequence.

Additionally, there are nucleotide segments that are difficult to write, and thus should be avoided when encoding a set of information into a nucleotide sequence. In various embodiments, encoding of a set of information into a nucleotide sequence comprises the use of one of the remaining distinguishable feature sets as the encoding symbols, such as may correspond to binary 0/1, trinary 0/1/2 or quaternary 0/1/2/3 code, etc., along with an error correcting encoding to define the set of information in a way that avoids the hard to read and hard to write features. In this way, overall performance of an information storage system is improved.

DNA Reading Device:

In various aspects, the DNA reading device used herein is a device that takes a pool of DNA molecules and produces a set of measured signals for each of the molecules sampled or selected from this pool. Such signals are then translated into a DNA sequence, or otherwise used to characterize the base patterns or motifs present in the DNA molecules. Current methods for reading data stored in DNA may rely on commercial next-generation DNA sequencers for the primary recovery of sequences from DNA samples. Such readers actually survey only a small portion of the DNA molecules introduced into the system, so that only a small fraction will undergo an actual read attempt. Thus, amplification prior to DNA reading is common, given that most input DNA molecules are never analyzed, and are simply wasted. Furthermore, many methods of DNA sequencing have an amplification step as a fundamental part of the process that amplifies DNA onto a surface or a bead in preparation for sequencing, such as exemplified by the commercial Illumina HiSeq System (Illumina, Inc.), the 454 System (Roche, Inc.), or the Ion Torrent System (Thermo Fisher, Inc.), or as is done in classical Sanger sequencing, such as using a thermocycling terminator sequencing reaction to produce sufficient input material required to meet the limits of the detection process. Further, there may be amplification steps performed in nanopore sequencing. Other methods may use amplification to add tags for sequencing.

DNA sequencing methods may also separately rely on one or more rounds of amplification procedures during the sample preparation phase. Such methods have been used for the addition of adapter DNA segments to support subsequent processing. Also, some sequencing methods at least require that a single-stranded template have its complementary strand present for sequencing, such as the "Circular Consensus Sequencing" of Pacific BioSciences, Inc., or the "2D" hairpin sequencing of Oxford Nanopore Technologic, Inc. Such a method, if presented with a single-stranded template as input, requires a process with at least one round of extension, a form of amplification, to create the complementary strand before actual sequencing can begin. In addition, methods that require a relatively large amount of input template for the primary sequencing process, such as nanopore sequencing with inefficient pore loading, also may require amplification of input DNA to achieve the require input amount lower limits.

DNA Library Management:

In various embodiments, DNA library management comprises a collection of operational procedures and related methods and apparatus carried out on physical DNA. Some such procedures relate to the mechanics of physical storage and retrieval of the DNA, such as drying down DNA from solution, re-suspending dried DNA into solution, and the transfer and storage of the physical quantities of DNA, such as into and out from freezers. Other procedures relate to the information storage management, such as making copies of data, deleting data, and selecting subsets of the data, all of which entail physical operations on the DNA material. Copying DNA or selecting DNA from a pool are generally performed using PCR amplification or linear amplification methods, thus common methods for library management may rely on amplification of DNA. For example, for a library prepared with PCR primer sites in place, an entire archive can be copied by taking a representative sample of the DNA and then PCR amplifying this up to the requisite amount for a copy. For further example, for a library prepared with volume-specific PCR primers, a volume from the library can be selected by using PCR primers to amplify up just the desired volume from a small DNA sample representing the entire library.

Motivations for Amplification in DNA Digital Data Storage:

DNA information storage systems envisioned from the above elements (DNA writer, DNA reader) may not work effectively at a specific single molecule level, and this motivates the use of amplification. That is, if there were a target DNA data storage sequence, such as GATTACA, it would not be feasible to make only a single physical molecule representing that sequence, then archive and handle the single molecule, and then read data from that single molecule. The infeasibility is due to the many sources of molecular structure error, loss of molecules, and limits of signal detection that exist in many such component processes. Thus, it is frequently proposed that there be amplification of the single molecule, at various stages in the process, to provide many more trial molecules to engage in all these processes. Thus, the goal achieved herein is to provide specific processes that individually or collectively remove the need for amplification steps in the various processes that comprise the DNA data storage system.

Benefits of Amplification-Free Methods and Apparatus in DNA Data Storage:

There are many benefits to amplification-free processes in a DNA information storage system. In general, amplification of DNA in the context of an information storage system will add cost, time, and operational complexity to the system, directly from the demands of the procedure. Amplification also typically amplifies some sequences more than others, and thus it may introduce representational bias into the data in storage system that could result in loss of information or inaccurate information, or an increase in the time or cost to recover information. Amplification can also produce errors in the DNA sequences, as the enzymes involved can make errors during the copying process, or can create chimeric molecules that contain sequence parts of different template DNAs, or partial molecules that are not complete copies. Thus amplification can produce errors in the data, or spurious "noise" molecules. DNA amplification can also lead to contamination, as the large quantities of DNA generated during amplification can contaminate other non-amplified samples and result in a substantial fraction of the total DNA content in such samples coming from the source of contamination. Thus, amplification could produce a "corruption" of stored data. Amplification methods also typically require one, two, or more flanking primer sequences at the ends of the DNA molecules to support the priming and enzymatic extension processes used to achieve amplification. Such primer sequences, which are typically in the range of 6 to 30 bases in length, must be synthesized into the DNA molecules, and thus this increases the cost, complexity and potential for errors in the DNA writing processes.

Amplification also generally cannot reproduce DNA modifications, of which there are a great many known in nucleic acid chemistry and which are used in the methods described herein. Thus, the use of amplification at any point in the DNA data storage system greatly limits the ability to use this great diversity of modified DNA, which could otherwise be used to improve the performance of a DNA data storage system. It is thus a benefit of amplification-free systems that such systems enable the use of such modified forms of DNA to be used as the information storage molecule. For example, modified DNA may comprise substituent groups on the DNA bases that increase signal to noise in a sensor when the DNA is read by the sensor, thereby greatly improving the power of the reading system. DNA modifications can be used to enhance the writing process, the stability of the resulting molecules, or to enhance the ability to manipulate and read data from the molecules. Use of modified DNA can provide data security or encryption, by having detectable modifications that are known only to trusted parties, or that only special reading systems could read. There are many types of modifications known to those skilled in such chemistry, which could potentially be used to enhance the capabilities of DNA data storage system, such as modified bases, modifications to the DNA backbone, such as in Peptide Nucleic Acids (PNAs), or thiol-phosphate or iodo-phosphate modifications of the backbone, or other DNA analogs such as Locked Nucleic Acids (LNAs), or diverse Xeno Nucleic Acids (XNAs), or modifications to the sugar ring, or methylated bases, or labeled bases, or the addition of other chemical groups at various sites of the DNA molecule, such as biotin or other conjugation or binding groups, or groups that create stronger signals for the reader.

A DNA digital data storage system in accordance with the present disclosure benefits from having lower operational costs by being entirely amplification-free or by comprising at least one amplification-free subsystem. It is a further benefit of the present system that the time it takes to store and/or recover information may be reduced. It is a further benefit that the system may have lower complexity, and consequently lower total ownership costs, lower risks of failure, or greater mean time between failures. It is a further benefit that the representation biases inherent in amplification processes are avoided, so that in the writing, extracting or reading DNA, the diverse sequences involved get more equal representation in these respective processes and in the overall system for storing and retrieving information. It is a further benefit to avoid the forms of introduced error or data corruption that are contributed by amplification. It is a further benefit to avoid the need to synthesize amplification primer sequences into the DNA molecules. It is a further benefit that potential contamination of other DNA data storage samples by amplification products is eliminated, thereby increasing system integrity, robustness, efficiency and security. It is a further benefit that amplification-free DNA information systems or subsystems therein remain compatible with the use of modified DNA, which may comprise modifications to the bases, sugars or backbone of the DNA, and which may provide for more effective reading systems (e.g., enhanced sensor signals) or more effective writing systems (e.g., more efficient synthesis chemistry), or which may provide more options for encoding information into DNA.

Methods of Avoiding Amplification in Writing:

In various embodiments, synthetic methods for writing DNA are provided that co-synthesize many instances of physical DNA molecules for each desired sequence. FIG. 6 shows a synthesis process intended to produce DNA molecules representing N target sequences from M distinct start sites for each target sequence. The process then comprises cyclical synthesis reactions that successively add one base or base segments in parallel to these M sites via regionally or chemically isolated and localized bulk reactions. Ideally, M DNA molecules are produced, all representing the target DNA sequence. For such cyclical, successive base addition processes, co-synthesized replicates of each target DNA sequence are naturally produced, and thus they can provide for an amplification-free process for writing up to M physical instances of each target DNA sequence. Such methods can be part of an amplification-free DNA storage system. Examples of such methods of DNA synthesis include ink-jet printer synthesis processes for printing of DNA oligonucleotides, such as has been done commercially by Twist Bioscience, Inc. and by Agilent, Inc., light-directed parallel synthesis of DNA oligonucleotides, such as has been done commercially by Affymetrix, Inc. and Nimblegen, Inc., as well as many approaches to operating a large number of small-volume or micro-fluidic classical phosphoramidite DNA synthesis reactions, such as has been done by Applied Biosystems, Inc. in their 3900 DNA Synthesizer (48 parallel synthesis columns). Thus, by directly co-synthesizing a greater number of molecules of each target sequence within such a synthesis process, amplification of these synthesis products post-synthesis to produce a desired number of copies is avoided.

Methods of Avoiding Amplification in Reading:

When reading DNA using present sequencing technologies, there is often a requirement to amplify the input DNA. In some methods, this occurs because the method requires larger input amounts, and therefore requires a grossly larger quantity of DNA than would be typically available from various sample sources. In other methods, the creation of the sequencing library includes amplification steps. In yet other methods, commonly known as clonal sequencing methods, many copies of the molecule to be sequenced must be produced directly and localized on a support as an integral part of the sequencing process, such as the DNA clusters used in the Solexa/HiSeq instruments (Illumina, Inc.), the DNA "SNAP or ISP" beads used in the Ion Torrent instruments (Thermo Fisher, Inc.), or the DNA beads required by the ABI SOLiD instruments (Life Technologies, Inc.), or the DNA beads used in the 454 instruments (Roche, Inc.). Such amplification requirements can be eliminated by using a suitable single-molecule sequencing method. In such methods, a single DNA molecule is analyzed by a sensor to produce the fundamental sequence read or data extraction from the molecule. Such methods in principle do not require amplifying the DNA molecules prior to analysis by the sensor. Thus, utilizing a suitable single molecule DNA reading sensor provides the means to achieve amplification-free reading. Such single molecule methods of DNA sequencing are illustrated in FIGS. 24 and 25.

Also of note are methods that use a carbon nanotube having a polymerase attached thereon to produce electrical signals, as in the sensor illustrated in FIG. 25. Note, however, that while in principle such single-molecule sequencing systems could provide for amplification-free reading of DNA, as used commercially, such systems often require amplification in their established protocols. For example, the Oxford Nanopore Minion Sequencer requires microgram quantities of input DNA in the standard protocol, which would require some form of amplification to achieve in the context of DNA data storage. Also, the preferred sequencing mode of the Oxford System "2D" sequencing requires having a double-stranded molecule because it reads both strands to produce a more accurate consensus sequence after joining them with a hairpin adapter in the sample preparation phase. This typically would require an enzymatic amplification step to synthesize the complementary DNA strand for the primary single-stranded synthetic storage molecule. Other sequencers may require double-stranded input DNA, and thus would typically require an amplification step to create the complementary strand from the primary single-stranded synthetic storage molecule.

An embodiment for a single molecule DNA reader not requiring any amplification of the DNA to be read is a molecular electronics sensor deployed on a CMOS sensor pixel array chip, as illustrated in FIGS. 7-23 and 25, and further described below.

Methods of Avoiding Amplification in DNA Archive Management:

The major operations a DNA data storage archive management system may comprise are considered below.

1. DNA Storage Archive Operations

For a given archive, it may be desirable to perform the following operations:

Create a copy of the archive;
Append data to the archive;
Readout a targeted volume from the archive;
Delete a volume from the archive; and
Search the archive.

In various embodiments, a DNA archive in accordance with the present disclosure exists in its primary physical state as a pool (i.e., a mixture) of DNA molecules, with each desired DNA sequence represented by a number of molecular exemplars. This pool of DNA molecules could be stored in a dry state, or in solution phase. In any case, the archive can be temporarily brought up to working temperatures in a compatible buffer solution to perform these operations. These operations would be performed efficiently by the physical storage system, which may include automation for handling of tubes, liquid handling, performing biochemical reactions, and the other procedures related to maintaining and manipulating the physical archive material.

These storage-related operations can be achieved without amplification, in contrast to doing these operations as they would commonly be done with amplification, as follows:

2. Copying

Copying an archive may be performed without any amplification by simply taking an aliquot of the stock solution. This provides a functional copy as long as a sufficient amount is taken to support future retrieval of information, and also to perhaps support limited numbers of further archive operations, such as further copying. For contrast, copying would more commonly be done via amplification, such as by including in the encoding DNA molecules amplification primer sites, and thus a small sample from the stock can be taken, followed by priming and amplifying, in linear or exponential amplification reactions, to obtain a substantial amount of material representing a functional copy of the original archive. Thus, a beneficial way to avoid such amplification processes for copying an archive is provided.

Copying of an archive may also be performed without amplification by using an amplification-free DNA reading system to read all the information from the archive, and then using an amplification-free DNA writing system to write all of the information into a new DNA archive, thereby achieving a DNA data copy of the original DNA data archive.

3. Appending

Appending data to the archive or merging archives can be achieved simply by pooling in and mixing with the additional DNA or archive material. This does not require amplification.

4. Targeted Reading

Working with individual "volumes" within an archive can be performed in an amplification-free manner by encoding into the DNA molecules sequence-specific oligonucleotide binding sites, with a different identifier/binding sequence for each volume to be made so accessible. Then, to readout a specific volume, hybridization-based capture could be used to select out specific DNA fragments with desired binding sequences. This process can be amplification free. Volume identifiers could also be added by synthesizing DNA with nucleotide modifications, so the relevant binding targets are not via DNA-sequence specific hybridization per se, but in other modifications on the bases used in the synthesis. For example, use of biotinylated bases, or bases with various hapten modifications, PNAs, non-classical DNA bases, or segments that carry epitope targets for antibody binding, or the use of PNA primer sites for improved binding affinity, all similarly provide selective ability to bind or manipulate subsets of the DNA via the corresponding interaction partners for these modifications intentionally introduced in the synthesis. These amplification-free targeting methods are all in contrast to targeted reading that relies on PCR-like processes to amplify out the target volume of interest.

Another embodiment of amplification-free targeted reading is the process whereby the archive, or a representative sample of the archive, is first presented to an amplification-free reader, which obtains reads sampling from the information content of the entire archive. Presuming the reads have a volume identifier in them, the read data from the desired volume are selected informatically from all such read data, thereby achieving the targeted reading through informatics selection. Another such embodiment relies on a reader that can in real-time read the volume identifier on a fragment, and either halts, or rejects and acquires another DNA fragment, if the identifier is not in the target volume, but otherwise completes the read if it detects the target volume identifier, achieving targeted reading. This is a dynamic informatics selection, which has the benefit of reading less unneeded information in the course of reading the targeted volume. Readers that can provide this capability include the molecular electronics sensor described in detail below, as well as certain embodiments of nanopore sequencing sensors.

5. Searching

Search of an archive for a literal input string can be achieved by encoding the search string or strings of interest into DNA form, synthesizing a complementary form or related primers for the desired DNA sequences and using hybridization extract from the archive of these desired sequence fragments. The hits can be identified by quantifying the amount of DNA recovered, or by using the DNA data reader to survey the recovered material. The search could report either presence or absence, or could recover the associated fragments containing the search string for complete reading. In contrast, searching methods that rely on PCR-like processes to amplify out the search target or to capture such targets and then amplify the results are to be avoided.

Embodiments of Amplification-Free Reading:

In various embodiments, amplification-free DNA reading herein comprises an all-electronic measurement of a single DNA molecule as it is processed by a polymerase or other probe molecule integrated into an electrical circuit that monitors an electrical parameter of the sensor circuit, such as the current. In an embodiment for DNA data storage reading, these sensors are deployed on a CMOS sensor array chip, with a large pixel array that provides the current measurement circuitry. Such a sensor chip may have millions of sensors, each processing successive DNA molecules, so that the required amount of input DNA may be as low as millions of total molecules. This provides for highly scalable, fast reading of DNA molecules without the need to pre-amplify the DNA, or amplify a specific target DNA molecule it as part of the reading process.

In various embodiments of the DNA information storage system herein, the DNA reading device comprises a massively parallel DNA sequencing device, which is capable of high speed reading of bases from each specific DNA molecule such that the overall rate of reading stored DNA information can be fast enough, and at high enough volume, for practical use in large scale archival information retrieval. The rate of reading bases sets a minimum time on data retrieval, related to the length of stored DNA molecules.

FIG. 7 shows an embodiment of a molecular electronic sensing circuit for a molecular electronics sensor capable of amplification-free DNA reading in which a molecule completes an electrical circuit and an electrical circuit parameter is measured versus time to provide a signal, wherein variations in signal reflect interactions of the molecule with other molecules in the environment. As illustrated in FIG. 7, a molecular electronics sensor circuit 1 comprises a circuit in which a single probe molecule 2, (or alternatively, a sensor complex comprising two or a small number of molecules), forms a completed electrical circuit by spanning the electrode gap 9 between a pair of spaced-apart nano-scale electrodes 3 and 4. Electrodes 3 and 4 may be positive and negative electrodes, or source and drain electrodes, and in this case are disposed on a support layer 5. The sensor molecule may be electrically conjugated in place to each of the electrodes by specific attachment points 6 and 7. In certain aspects, an electronic parameter 100 of the circuit is measured as the sensor molecule 2 interacts with various interacting molecules 8 to provide signals 101 in the measured electronic parameter. The measured parameter 100 may comprise current (i) passing between the electrodes and through the sensor molecule 2 versus time, with the electrical signals 101 in the measured parameter indicative of molecular interactions between the interacting molecules 8 and the sensor molecule 2, as illustrated by the plot of (i) versus (t) in FIG. 7.

FIG. 8 illustrates an embodiment of a polymerase-based molecular electronics sensor for use herein as a DNA reader device. A sensor, such as illustrated in FIG. 8, and comprising a polymerase or other processive enzyme, produces distinguishable signals in the monitored current over time when the polymerase encounters distinct molecular features on the DNA (abbreviated in FIG. 8 as "FEAT 1", "FEAT 2", and so forth). Such distinct molecular features can be used in planned arrangements to encode information into synthetic DNA molecules, which can in turn be read via the sensor knowing that distinguishable signals will be see in the monitored electrical parameter. In various embodiments, the molecular complex of an individual sensor circuit comprises a single polymerase enzyme molecule that engages with a target DNA molecule to produce electrical signals as it processes the DNA template. Under appropriate conditions, such a polymerase will produce distinguishable electrical signal features, corresponding to specific distinct features of a template DNA molecule, such as illustrated in FIG. 8 by two different peak shapes/amplitudes in the signal trace. Such distinguishable signal features can therefore be used to encode information in synthetic DNA molecules, through a great variety of encoding schemes, such as those of FIG. 4, discussed above, and therefore such a sensor provides the reader for encoded data.

FIG. 9 illustrates an embodiment where the polymerase molecule is conjugated to a bridge molecule conjugated at its ends to source and drain electrodes to span the gap between the electrode pair. That is, the sensor comprises a molecular sensor complex further comprising the polymerase and the bridge molecule. The sensor may further comprise a buried gate electrode as illustrated, which can be used to further modulate the sensitivity of the circuit. Current between the electrodes is the measured electrical parameter. When the polymerase engages a proper template, such as a primed, single-stranded DNA molecule, in the presence of suitable buffer solution and dNTPs as shown, the activity of the polymerase in synthesizing a complementary strand causes perturbations in the measured signals related to the detailed kinetics of the enzyme activity. In this case, the plot of current through the electrodes versus time provides a signal with distinguishable features (such as amplitude variations) corresponding to structural features of the DNA molecule being processed. In this embodiment, two different sequence motifs AA and CCC are used in an encoded DNA molecule to provide two distinguishable signals when encountered by the polymerase. In this way, the motifs AA and CCC provide a means to encode binary bits 0/1 into the template DNA, such as by using AA for the binary bit 0 and using CCC for the binary bit 1. Importantly, useful encoding and reading of information is possible even without single base resolution of DNA sequences, by instead relying on distinguishable sequence motifs, which is a clear advantage to using a single bit/single DNA base BES which necessitates single base resolution in reading.

FIG. 10 shows the detailed protein anatomy and DNA engagement of one of the exemplary polymerase enzymes for use as the probe molecule of a molecular sensor herein, specifically the *E. coli* Klenow fragment. The structure shown is PDB ID 1KLN. The detailed structure and how it engages the template DNA inform the choice of how to best conjugate the enzyme into the circuit, so as not to interfere with its interaction with DNA, and to position the signaling portions of the protein or DNA near to the molecular bridge for enhanced signal generation via proximity. The helix, sheet and loop portions of the enzyme are pointed out in this conformation wherein the DNA is engaged with the enzyme.

FIG. 11 shows embodiments of a molecular sensor 130A, usable as a DNA reading device, wherein the polymerase enzyme 134A is conjugated to a molecular bridge molecule 133A, at a conjugation point 135A representing a bond between a specific site on the enzyme 134A and a specific site on the bridge molecule 133A. As shown, the bridge molecule 133A is bonded to each of the spaced-apart electrodes to span the electrode gap 139A. The bridge molecule 133A comprises first and second ends functionalized to bond to each of the electrodes in the pair of electrodes at conjugation points 131A and 132A.

FIG. 12 shows the molecular structure of one specific embodiment of a polymerase-based molecular sensor 130B for reading DNA in a DNA information storage and retrieval system, wherein the polymerase 134B is conjugated to a bridge molecule 133B comprising a 20 nm long (=6 helical turns) double-stranded DNA. The sensor 130B further comprises a pair of spaced apart chromium electrodes 138B and 139B, disposed on a substrate layer, such as $SiO_2$, and spaced apart by about 10 nm. On each electrode 138B and 139B are deposits of gold 131B that participate in the bonding of the bridge molecule to each of the electrodes. The DNA bridge molecule 133B shown is conjugated to the gold-on-chromium electrodes through thiol groups on first and second ends of the DNA bridge, binding to gold via sulfur-gold bonds 132B, and wherein the polymerase 134B is conjugated to the DNA bridge molecule 133B at a centrally located biotinylated base on the DNA bridge 135B, bound to a streptavidin molecule 136B, in turn bound to the polymerase 134B via a specific biotinylated site 135B on the polymerase 134B. In this way, the streptavidin 136B links the polymerase 134B to the DNA bridge molecule 133B by way of two biotin-streptavidin linkages 135B. The processive enzyme molecular sensor 130B is illustrated translocating a DNA substrate molecule 137B. As discussed, the DNA substrate molecule 137B may be encoded with information comprising arrangements of signaling features such as bound DNA oligonucleotide segments or perturbing groups.

In various embodiments of a molecular electronics sensor for use herein, the polymerase may be a native or mutant form of Klenow, Taq, Bst, Phi29 or T7, or may be a reverse transcriptase. In various embodiments, the mutated polymerase forms will enable site specific conjugation of the polymerase to the bridge molecule, arm molecule or electrodes, through introduction of specific conjugation sites in the polymerase. Such conjugation sites engineered into the protein by recombinant methods or methods of synthetic biology may, in various embodiments, comprise a cysteine, an aldehyde tag site (e.g., the peptide motif CxPxR), a tetracysteine motif (e.g., the peptide motif CCPGCC), or an unnatural or non-standard amino acid (NSAA) site, such as through the use of an expanded genetic code to introduce a p-acetylphenylalanine, or an unnatural cross-linkable amino acid, such as through use of RNA- or DNA-protein crosslink using 5-bromouridine.

In various embodiments, the bridge molecule may comprise double-stranded DNA, other DNA duplex structures, such as DNA-PNA or DNA-LNA or DNA-RNA duplex hybrids, peptides, protein alpha-helix structures, antibodies or antibody Fab domains, graphene nanoribbons or carbon nanotubes, or any other of a wide array of molecular wires or conducting molecules known to those skilled in the art of molecular electronics. The conjugations of polymerase to such molecules, or of such molecules to the electrodes, may be by a diverse array of conjugation methods known to those skilled in the art of conjugation chemistry, such as biotin-avidin couplings, thiol-gold couplings, cysteine-maleimide couplings, gold or material binding peptides, click chemistry coupling, Spy-SpyCatcher protein interaction coupling, antibody-antigen binding (such as the FLAG peptide tag/anti-FLAG antibody system), and the like. Coupling to electrodes may be through material binding peptides, or through the use of a SAM (Self-Assembling-Monolayer) or other surface derivatization on the electrode surface to present suitable functional groups for conjugation, such as azide or amine groups. The electrodes comprise electrically conducting structures, which may comprise any metal, such as gold, silver, platinum, palladium, aluminum, chromium, or titanium, layers of such metals in any combination, such as gold on chromium, or semiconductors, such as doped silicon, or in other embodiments, a contact point of a first material on a support comprising a second material, such that the contact point is a site that directs chemical self-assembly of the molecular complex to the electrode.

In various embodiments, electrical parameters measured in a sensor, such as the sensor illustrated in FIG. 12, can in general be any electrical property of the sensor circuit measurable while the sensor is active. In one embodiment, the parameter is the current passing between the electrodes versus time, either continuously or sampled at discrete times, when a voltage, fixed or varying, is applied between the electrodes. In various embodiments, a gate electrode is capacitively coupled to the molecular structure, such as a buried gate or back gate, which applies a gate voltage, fixed or variable, during the measurement. In various other embodiments the measured parameter may be the resistance, conductance, or impedance between the two electrodes, measured continuously versus time or sampled periodically. In various aspects, the measured parameter comprises the voltage between the electrodes. If there is a gate electrode, the measured parameter can be the gate voltage.

In various embodiments, the measured parameter in a molecular electronics sensor, such as the sensor of FIG. 12, may comprise a capacitance, or the amount of charge or voltage accumulated on a capacitor coupled to the circuit. The measurement can be a voltage spectroscopy measurement, such that the measurement process comprising capturing an I-V or C-V curve. The measurement can be a frequency response measurement. In all such measurements, for all such measured parameters, there are embodiments in which a gate electrode applies a gate voltage, fixed or variable, near the molecular complex during the measurement. Such a gate will typically be physically located within a micron distance, and in various embodiments, within a 200 nm distance of the molecular complex. For the electrical measurements, in some embodiments there will be a reference electrode present, such as a Ag/AgCl reference electrode, or a platinum electrode, in the solution in contact with the sensor, and maintained at an external potential, such as ground, to maintain the solution at a stable or observed potential, and thereby make the electrical measurements better defined or controlled. In addition, when making the electrical parameter measurement, various other electrical parameters may be held fixed at prescribed values, or varied in a prescribed pattern, such as, for example, the source-drain electrode voltage, the gate voltage if there is a gate electrode, or the source-drain current.

The use of a sensor, such as the sensor illustrated in FIG. 12, to measure distinguishable features of a DNA molecule requires the polymerase to be maintained in appropriate physical and chemical conditions for the polymerase to be active, to process DNA templates, and to produce strong, distinguishable signals above any background noise (i.e., high signal-to-noise ratio, or "SNR"). To achieve this, the polymerase may reside in an aqueous buffer solution. In various embodiments, a buffer solution may comprise any combination of salts, e.g., Nalco or KCl, pH buffers, Tris-HCl, multivalent cation cofactors, Mg, Mn, Ca, Co, Zn, Ni, Fe or Cu, or other ions, surfactants, such as Tween, chelating agents such as EDTA, reducing agents such as DTT or TCEP, solvents, such as betaine or DMSO, volume concentrating agents, such as PEG, and any other component typical of the buffers used for polymerase enzymes in molecular biology applications and known to those skilled in the field of molecular biology. The sensor signals may also be enhanced by such buffers being maintained in a certain range of pH or temperature, or at a certain ionic strength. In various embodiments, the ionic strength may be selected to obtain a Debye length (electrical charge screening distance) in the solution favorable for electrical signal production, which may be, for example, in the range of from about 0.3 nm to about 100 nm, and in certain embodiments, in the range of from about 1 nm to about 10 nm. Such buffers formulated to have larger Debye lengths may be more dilute or have lower ionic strength by a factor of 10, 100, 1000, 100,000 or 1 million relative to the buffer concentrations routinely used in standard molecular biology procedures such as PCR. Buffer compositions, concentrations and conditions (pH, temperature, or ionic strength, for example) may also be also selected or optimized to alter the enzyme kinetics to favorably increase the signal-to-noise ratio (SNR) of the sensor, the overall rate of signal production, or overall rate of information production, in the context of reading data stored in DNA molecules. This may include slowing down or speeding up the polymerase activity by these methods, or altering the fidelity or accuracy of the polymerase. This optimal buffer selection process consists of selecting trial conditions from the matrix of all such parameter variations, empirically measuring a figure of merit, such as related to the discrimination of the distinguishable features, or to the over speed of feature discrimination when processing a template, and using various search strategies, such as those applied in statistical Design Of Experiment (DOE) methods, to infer optimal parameter combinations.

The use of a sensor such as the sensor of FIG. 12 to measure distinguishable features of a DNA molecule requires the polymerase be provided with a supply of dNTPs so that the polymerase can act processively on a template single-stranded DNA molecule to synthesize a complementary strand. The standard or native dNTPs are dATP, dCTP, dGTP, and dTTP, which provide the A, C, G, and T base monomers for polymerization into a DNA strand, in the form required for the enzyme to act on them as substrates. Polymerase enzymes, native or mutant, may also accept analogues of these natural dNTPs, or modified forms, that may enhance or enable the generation of the distinguishable signals.

In various aspects of DNA reading herein, if a system reads a DNA molecule at a speed of 1 base per 10 minutes, as is representative of current next generation, optical dye-labeled terminator sequencers, then reading a 300 base DNA molecule takes at least 3,000 minutes (50 hours), aside from any time required to prepare the sample for reading. Such relatively slower systems therefore favor storing information in a larger number of shorter reads, such as 30 base reads that could be read in 5 hours. However, this requires a larger number of total reads, so the system must support billions or more such reads, as it the case on such sequencers. The current generation of optical massively parallel sequencers, read on the order of 3 billion letters of DNA per 6-minute cycle, or roughly the equivalent of 1 billion bits per minute, or 2 MB per second, although for data stored as 100 base DNA words, this would also require 600 minutes (5 hours). This can be seen to be a relatively low rate of data reading, although within a practical realm, as atypical book may contain 1 MB of textual data. The overall rate is practical, but the slow per base time makes this highly inefficient for reading a single book of data, and ideally matched to bulk reading of 36,000 books in parallel, over 5 hours. Thus, there is also a lack of scalability in this current capability, and also a high capital cost of the reading device (optical DNA sequencers cost in the $100,000 to $1,000,000 range presently). More critically, on such current systems, the cost of sequencing a human genome worth of DNA, 100 billion bases, is roughly $1,000, which means the cost of reading information is $1,000 per 200 Giga-bits, or $40 per GB. This is radically higher than the cost of reading information from magnetic tape storage or CDs, which is on the order of $1 per 10,000 GB, or $0.0001 per GB, 400,000 fold less costly. Thus the cost of reading DNA should be reduced by several orders of magnitude, even by 1,000,000 fold, to make this attractive for large scale, long term archival storage, not considering other advantages. Such improvements may indeed be possible, as evidenced by the million-fold reduction in costs of sequencing that has already occurred since the first commercial sequencers were produced.

In various embodiment, the DNA reader of the present system comprises substantially lower instrument capital costs, and higher per-base reading speed, and greater scalability in total number of reads per run, compared to currently available optical next generation sequencing instruments. In various aspects, the reading device for use herein is based on a CMOS chip sensor array device in order to increase the speed and scalability and decrease the capital costs. An embodiment of such a device comprises a CMOS sensor array device, wherein each sensor pixel contains a molecular electronic sensor capable of reading a single molecule of DNA without any molecular amplification or copying, such as PCR, required. In various embodiments, the CMOS chip comprises a scalable pixel array, with each pixel containing a molecular electronic sensor, and such a sensor comprising a bridge molecule and polymerase enzyme, configured so as to produce sequence-related modulations of the electrical current (or related electrical parameters such as voltage, conductance, etc.) as the enzyme processes the DNA template molecule.

An exemplary molecular sensor and chip combination usable as a DNA reader device in the present DNA data storage system is depicted in FIGS. 12, 13, and 18-23. As discussed, FIG. 12 illustrates an exemplary molecular sensor comprising a bridge and probe molecular sensor complex further comprising a bridge of double-stranded DNA having about a 20 nm length (~60 bases), with thiol groups at both 5' ends for coupling to gold contacts on a metal electrode. The embodiment of FIG. 12 comprises a polymerase enzyme coupled to a molecular wire comprised of DNA, which plugs into a nano-electrode pair to form a sensor capable of producing sequence-related signals as the polymerase enzyme processes a primed DNA template.

As illustrated in FIG. 13, such a nano-sensor can be placed by post-processing onto the pixels of a CMOS sensor pixel array, which further comprises all the supporting measurement, readout and control circuitry needed to produce these signals from a large number of sensors operating in parallel. FIG. 13 illustrates an embodiment of various electrical components and connections in molecular sensors.

In the upper portion of the figure, a cross-section of an electrode-substrate structure 300 is illustrated, with attachment to an analyzer 301 for applying voltages and measuring currents through the bridge molecule of the sensor. In the lower portion of the figure, a perspective view of electrode array 302 is illustrated, usable for bridging circuits. Each pair of electrodes comprises a first metal (e.g., "Metal-1"), and a contact dot or island of a second metal (e.g., "Metal-2") at each electrode end near the gap separating the electrodes. In various examples, Metal-1 and Metal-2 may comprise the same metal or different metals. In other aspects, the contact dots are gold (Au) islands atop metal electrodes comprising a different metal. In various experiments, contact dots comprise gold (Au) beads or gold (Au)-coated electrode tips that support self-assembly of a single bridge molecule over each gap between electrode pairs, such as via thiol-gold binding.

FIGS. 14A-14C show drawings of electron micrograph (EM) images of electrodes comprising gold metal dot contacts for bridge binding in DNA sensors. In this example, electrodes are on a silicon substrate, and were produced via e-beam lithography. FIG. 14A shows an array of titanium electrodes with gold dot contacts. FIG. 14B shows an electrode gap of about 7 nm with gold dot contacts and with about a 15 nm gold-to-gold spacing in a closer-up EM image. In FIG. 14C, a close-up EM shows gold dots of approximately 10 nm in size positioned at the tips of the electrodes.

FIG. 15 sets forth current versus time plots obtained by measuring DNA incorporation signals with the sensor of FIG. 12. The plots show the current signals resulting from the sensor being supplied with various primed, single-stranded DNA sequencing templates and dNTPs for incorporation and polymerization. In each case, the major signal spikes represent signals from discrete incorporation events, wherein the polymerase enzyme adds another base to the extending strand. At the upper left of FIG. 15, the template is 20 T bases; at the upper right, the template is 20 G bases; at the lower left, the template is 20 A bases; and at the lower right, the template is 20 C bases. The approximate rate of incorporation observed is about 10-20 bases per second, consistent with standard enzyme kinetics except for the lower rate of ~1 base per second due to rate limiting factors (e.g., lower dNTP concentration).

FIG. 16 shows experimental data obtained from the sensor of FIG. 12 in which specific sequence motifs produced signals that are usable to encode 0/1 binary data. The sensor of FIG. 12 comprises the Klenow polymerase conjugated to a DNA bridge, which produces distinguishable signals from the encoding DNA sequence motifs 20A, 3C and 30A in the experimental template DNA. Such signals were produced by using the sensor of FIG. 12 in conjunction with a standard 1× Klenow buffer and relatively high concentration of dTTP, (10 µM), and 100 times lower concentration of the other dNTPs. The lower concentration of the other dNTPs, notably the low dGTP concentration, facilitates the distinguishable signal from the CCC region via the concentration-limited rate of incorporation. The result is that the poly-A tract has a high spike signal feature, and the poly-C tract has a low trough signal feature, which are readily distinguishable. The peaks and trough are usable to encode 0/1 binary data in the simple manner illustrated, with 0 encoded by the poly-A tract and read from the high peak signals having several seconds duration, and 1 encoded by the CCC tract and read from the low trough features having several seconds duration.

The use of the sensors of the present disclosure to measure distinguishable features of a DNA molecule requires the polymerase be provided with primed, single-stranded template DNA molecules as a substrate for polymerization of a complementary strand, in the course of generating the associated signals. In the context of encoding information in synthetic DNA molecules, these template molecules may be wholly chemically synthetic, and can therefore be provided with chemical or structural modifications or properties beyond those of native DNA, which may be used to enable or enhance the production of distinguishable signals for various embodiments. The polymerase, native or an engineered mutant, can accept as a substrate a great many such modified or analogue forms of DNA, many of which are well known to those skilled in the field of molecular biology. The use of such modifications to the template DNA can be used to create features with distinguishable signals.

In various embodiments, the DNA supplied to the polymerase as a template comprises some form of primed (double-stranded/single-stranded transition) site to act as an initiation site for the polymerase. For the purpose of storing digital data in DNA, in various embodiments, this priming will be pre-assembled into the encoding molecule, so that no further sample preparation is needed to prime the DNA template molecules.

Since the secondary structure in a DNA template can interfere with the processive action of a polymerase, it may be advantageous to reduce, avoid or eliminate secondary structure in the DNA data encoding template molecules used in DNA data reader sensors. Many methods to reduce secondary structure interference are known to those skilled in the field of molecular biology. Methods to reduce, avoid or eliminate secondary structure include, but are not limited to: using polymerases that possess strong secondary structure displacing capabilities, such as Phi29 or Bst or T7, either native or mutant forms of these; adding to the buffer solvents such as betaine, DMSO, ethylene glycol or 1,2-propanediol; decreasing the salt concentration of the buffer; increasing the temperature of the solution; and adding single strand binding protein or degenerate binding oligonucleotides to hybridize along the single strand. Methods such as these can have the beneficial effect of reducing secondary structure interference with the polymerase processing the encoding DNA and producing proper signals.

Additional methods available to reduce unwanted secondary structure for DNA data reading in accordance with the present disclosure comprise adding properties to DNA molecules produced by synthetic chemistry. For example, in some embodiments of the present disclosure, the data encoding the DNA molecule itself can be synthesized from base analogues that reduce secondary structure, such as using deaza-G (7-deaza-2'-deoxyguanosine) in place of G, which weakens G/C base pairing, or by using a locked nucleic acid (LNA) in the strand, which stiffens the backbone to reduce secondary structure. A variety of such analogues with such effects are known to those skilled in the field of nucleic acid chemistry.

Further methods are available in the present disclosure to reduce unwanted secondary structure for the DNA data reading sensor, because the DNA data encoding scheme determines the template sequence, and thus there is potential to choose the encoding scheme to avoid sequences prone to secondary structure. Such Secondary Structure Avoiding ("SSA") encoding schemes are therefore a beneficial aspect of the present disclosure. In general, for encoding schemes as described herein, which use distinguishable signal sequence features as the encoding elements, to the extent there are options in the choice of encoding schemes, all such alternative schemes could be considered, and the schemes that produce less (or the least) secondary structure would be favored for use. The alternative schemes are assessed relative to a specific digital data payload, or statistically across a representative population of such data payloads to be encoded.

For example, the importance of SSA encoding is illustrated in the embodiment where the sensor provides three distinguishable signal sequence features: AAAAA, TTTTT, and CCCCC. If all three features are used in encoding in the same strand (or on other strands), there is a strong potential for the AAAAA and TTTTT encoding elements, being complementary, to hybridize and lead to secondary structure, either within the strand or between DNA strands. Thus, if the data were instead encoded entirely by the scheme where the bit 0 encodes to AAAAA and the bit 1 encodes to CCCCC, (i.e., ignoring the use of TTTTT completely), all potential secondary structure is avoided. Thus, this encoding (or the other SSA choice, the bit 0 encoding to TTTTT and the bit 1 encoding to CCCCC) is preferred over a scheme that uses self-complementary sequences, even though information density is reduced by giving up one of the three available encoding elements. Thus, in general, SSA codes can be used when there are encoding options and when there is a potential for DNA secondary structure to form. As shown in this example, desirable SSA codes to reduce DNA secondary structure may be less information dense than what is theoretically possible for the distinguishable signal states. However, this tradeoff can result in a net gain of information density, or related overall cost or speed improvements, by avoiding data loss related to DNA secondary structure.

In various embodiments, methods for reducing secondary structure comprises the use of binding oligonucleotides to protect the single strand, wherein the oligonucleotides are chosen with sequence or sequence composition that will preferentially bind to the encoding features. Such binding oligonucleotides may more effectively protect the single strand and general degenerate oligonucleotides. For example, in the case described above with three distinguishable signal sequence features AAAAA, TTTTT, and CCCCC, all three could be used as encoding features, and they could be protected in single-stranded form by binding the template to the oligonucleotides TTTTT, AAAAA, and GGGGG, or to enhanced binding analogues of these, such as RNA, LNA or PNA forms, instead of DNA. Thus, use of binding oligonucleotides that preferentially bind to the encoding features is another means to mitigate unwanted secondary structure effects, although such binding oligonucleotides must be used with strand-displacing polymerases, such as native or mutant forms of Klenow, Bst or Phi29, such that the oligonucleotides themselves do not interfere. A further method for avoiding secondary structure is to prepare the information encoding DNA in primarily double-stranded form, with a nick or gap at the primer site for polymerase initiation, and the rest of the molecule in duplex form (with or without a hairpin bend) so that the DNA molecule exists in solution in a substantially duplex form, free of secondary structure due to single-strand interactions, within or between molecules.

In various embodiments, DNA molecules used to encode information for reading by the cognate molecular sensor can be prepared with architecture facilitating the reading process as well as the encoding and decoding processes. Various embodiments of DNA architecture are illustrated in FIG. 17. Illustrated is a representative physical form of a primed single-stranded DNA template (at the top of the drawing), along with the logical forms of an information encoding molecule for use in a digital data storage system. Exemplary forms may include Left and Right Adapters (shown as "L ADAPTOR" and "R ADAPTOR"), to facilitate manipulation of the information coding DNA molecules, a primer (e.g., pre-primed or self-priming, shown as "PRIMER"), left and right buffer segments (shown as "L-BUFFER" and "R-BUFFER") and a data payload segment ("DATA PAYLOAD").

With continued reference to FIG. 17, the adapters may comprise, for example, primers for universal amplification processes, used to copy the stored data, or may comprise hybridization capture sites or other selective binding targets, for targeted selection of molecules from a pool. In various embodiments, a primer segment contains primer target/structure, the L-BUFFER segment may contain a signal calibration sequence for the reader, or a buffering sequence prior to the DATA PAYLOAD segment, which contains information storing encoded sequence and related error correction sequence such as parity bits, as well as metadata for the storage method, such as related to the assembly of this information into larger strings. In various aspects, the R-BUFFER may contain an additional calibration sequence, as well as a buffer sequence preventing the polymerase enzyme getting too close to the end of the template when reading data. In various embodiments, the L-ADAPTER and R-ADAPTER may be sequence elements related to the storage or manipulation of the associated DNA segment, such as adapters for outer priming cites for PCR amplification, or hybridization based selection, or representing a surrounding carrier DNA for this insert, including insertion into a host organism genome as a carrier. In various embodiments, the adapters may comprise surrounding or carrier DNA, for example in the case of DNA data molecules stored in live host genomes, such as in bacterial plasmids or other genome components of living organisms.

With further reference to FIG. 17, the L-BUFFER and R-BUFFER segments may comprise DNA segments that support the polymerase binding footprint, or the segments may comprise various calibration or initiation sequences used to help interpret the signals coming from the data payload region. These buffer segments may contain molecular barcode sequences that are used to distinguish unique molecules, or to identify replicate molecules that are derived from the same originating single molecule. One such method of barcoding, known to those skilled in DNA oligo synthesis, comprises the addition of a short random N-mer sequence, typically 1 to 20 bases long, made for example by carrying out synthesis steps with degenerate mixtures of bases instead of specific bases.

With continued reference to FIG. 17, DNA logical structures comprise a data payload segment wherein specific data is encoded. In various embodiments, a data payload segment comprises the actual primary digital data being stored along with metadata for the storage method, which may comprise data related to proper assembly of such information fragments into longer strings, and/or data related to error detection and correction, such as parity bits, check sums, or other such information overhead.

In various aspects of the present disclosure, a DNA data payload of interest is processed by a polymerase sensor multiple times to provide a more robust recovery of digital data from DNA storage. In other aspects, a collection of such payloads on average are processed some expected number of multiple times. These examples benefit from a more accurate estimation of the encoding distinguishable features by aggregating the multiple observations. Multiple processing also has the benefit of overcoming fundamental Poisson sampling statistical variability to ensure that, with high confidence, a data payload of interest is sampled and observed at least once, or at least some desirable minimal number of times.

In various embodiments, the number of such repeat interrogations is in the range of 1 to about 1000 times, or in the range of about 10 to 100 times. Such multiple observations may comprise: (i) observations of the same physical DNA molecule by the polymerase sensor, and/or (ii) one or more polymerase sensors processing multiple, physically distinct DNA molecules that carry the same data payload. In the latter case, such multiple, physically distinct DNA molecules with the same data payload may be the DNA molecules produced by the same bulk synthesis reaction, the molecules obtained from distinct synthesis reactions targeting the same data payload, or replicate molecules produced by applying amplification or replication methods such as PCR, T7 amplification, rolling circle amplification, or other forms of replication known to those skilled in molecular biology. The aggregation of such multiple observations may be done through many methods, such as averaging or voting, maximum likelihood estimation, Bayesian estimation, hidden Markov methods, graph theoretic or optimization methods, or deep learning neural network methods.

In various embodiments of the present disclosure, digital data stored in DNA is read at a high rate, such as approaching 1 Gigabyte per second for the recovery of digital data, as is possible with large scale magnetic tape storage systems. Because the maximum processing speed of a polymerase enzyme is in the range of 100-1000 bases per second, depending on the type, the bit recovery rate of a polymerase-based sensor is limited to a comparable speed. Thus, in various embodiments millions of sensors are deployed in a cost effective format to achieve the desired data reading capacity.

In various embodiments, many individual molecular sensors are deployed in a large scale sensor array on a CMOS sensor pixel array chip, which is the most cost-effective, semiconductor chip manufacturing process. FIG. 18 illustrates an embodiment of a fabrication stack usable to create a massively parallel array of molecular sensors on a chip. In this example, the sensor measurement circuitry is deployed as a scalable pixel array as a CMOS chip, a nano-scale lithography process is used to fabricate the nano-electrodes, and molecular self-assembly chemical reactions, in solution, are used to establish the molecular complex on each nano-electrode in the sensor array. The result of this fabrication stack is the finished DNA reader sensor array chip indicated at the bottom of FIG. 18. In various embodiments, the nanoscale lithography is done using a high resolution CMOS node, such as a 28 nm, 22 nm, 20 nm, 16 nm, 14 nm, 10 nm, 7 nm or 5 nm nodes, to leverage the economics of CMOS chip manufacturing. In contrast, the pixel electronics may be done at a coarser node better suited to mixed signal devices, such as 180 nm, 130 nm, 90 nm, 65 nm, 40 nm, 32 nm or 28 nm. Alternatively, the nano-electrodes may be fabricated by any one of a variety of other fabrication methods known to those skilled in the art of nanofabrication, such as e-beam lithography, nano-imprint lithography, ion beam lithography, or advanced methods of photolithography, such as any combinations of Extreme UV or Deep UV lithography, multiple patterning, or phase shifting masks.

FIG. 19 illustrates an embodiment of a high-level CMOS chip pixel array architecture for a DNA reader in more detail at the left of the drawing figure. The CMOS chip pixel array architecture comprises a scalable array of sensor pixels, with associated power and control circuitry and major blocks such as Bias, Analog-to-Digital convertors, and timing. The inset in the figure shows an individual sensor pixel as a small bridged structure representing a single polymerase molecular sensor, and where this individual electronic sensor is located in the pixel array. FIG. 19 also illustrates (at the right side of the figure) the details of an embodiment of a polymerase molecular electronics sensor circuit pixel in the array. As illustrated, a complete sensor circuit comprises a trans-impedance amplifier, voltage-biasable source, drain, and (optionally) gate electrodes, and a reset switch, along with a polymerase enzyme electrically connected between the source and drain electrodes (with or without bridge and/or arm molecules). The feedback capacitor illustrated is optional to improve stability of the amplifier. The output of the pixel circuit (the measurable electronic parameter) in this embodiment is current, which is monitored for perturbations relating to the activity of the polymerase. That is, the current output from the trans-impedance amplifier is the measurable electrical parameter for this sensor pixel that is monitored for perturbations. It should be noted that one of the two electrodes can be grounded, in which case a biasable voltage is supplied across the electrodes.

FIG. 20 illustrates an embodiment of an annotated chip design layout file and the corresponding finished chip for comparison. In FIG. 20, (A), at left, is the finished design of an embodiment of the CMOS pixel array of FIG. 19 with 256 pixels, annotated to show the location of the Bias 190, Array 191 and Decoder 192 regions of the chip. The design layout also comprises a test structures 193 region. In FIG. 20, (B), at right, is a drawing of an optical microscope image of the corresponding finished chip based on the final design, produced at TSMC, Inc. semiconductor foundry (San Jose, Calif.) with the TSMC 180 nm CMOS process, with no passivation layer.

FIG. 21 shows illustrations of scanning electron microscope (SEM) images of the finished CMOS chip 200 of FIG. 20 (256 pixel array, 2 mm×2 mm), which clearly shows the sub-optical surface features of the 80 µm pixel 201, and notably the exposed vias (the source, gate, and drain) where the nano-electrodes can be deposited by post-processing and electrically connected into the amplifier circuit as shown in FIG. 19, at right. The furthest right drawing of a 100 nm SEM image 202 in FIG. 21 shows an e-beam lithography fabricated pair of spaced apart nanoelectrodes with a molecular complex in place. The sketch 203 at the bottom right of FIG. 21 is an illustration of the processive enzyme molecular electronics sensor comprising a polymerase molecular complex 207, spaced apart electrodes 204 and 205, each labeled by a gold dot contact, wherein the electrode gap 206 is about 10 nm.

In various embodiments of a DNA reader device, use of a CMOS chip device in conjunction with nano-scale manufacturing technologies, ultimately yield a much low cost, high throughput, fast, and scalable system. For example, sensors such as this can process DNA templates at the rate of 10 or more bases per second, 100 or more times faster than current optical sequencers. The use of CMOS chip technology ensures scalability and low system cost in a mass-producible format that leverages the enormous infrastructure of the semiconductor industry. As noted, whatever error modes or accuracy limitations may exist in a DNA sensor, or that may arise at faster reading speed (e.g., by modifying the enzyme or buffer or temperature or environmental factors, or sample data at lower time resolution), can be compensated for in the overall encoder/decoder-reader-writer framework described.

In various embodiments of the present disclosure, a DNA reader chip for use herein comprises at least 1 million sensors, at least 10 million sensors, at least 100 million sensors, or at least 1 billion sensors. Recognizing that at a typical sensor data sampling rate of 10 kHz, and recording 1 byte per measurement, a 100 million sensor chip produces raw signal data at a rate of 1 Terabyte (TB) per second. In considering how many sensors are desirable on a single chip, one critical consideration is the rate at which such a chip can decode digital data stored in DNA compared to the desirable digital data reading rates. It is, for example, desirable to have digital data read out at a rate of up to about 1 Gigabyte per second. Note that each bit of digital data encoded as DNA will require multiple signal measurements to recover, given that a feature of the signal use used to store this information, so this raw signal data production rate for the measured signal will be much higher that the recovery rate of encoded digital data. For example, if 10 signal measurements are required to recover 1 bit of stored digital data, and each measurement is an 8-bit byte, that is a factor of 80 bits of signal data to recover 1 bit of stored digital data. Thus, digital data reading rates are anticipated to be on the order of 100 times slower than the sensor raw signal data acquisition rate. For this reason, achieving desirable digital data reading rate of 1 Gigabyte/sec would require nearly 0.1 TB/sec of usable raw signal data. Further, given that not all the sensors in a single chip may be producing usable data, the need for chips that produce up to 1 TB/sec of raw data is desirable, based on the desired ultimate digital data recover rates from data stored as DNA. In various embodiments, such recovery rates correspond to a 100 million sensor pixel chip.

In various embodiments of the present disclosure, multiple chips are deployed within a reader system to achieve desired system-level digital data reading rates. The DNA data reader chip of FIG. 18 is, in various embodiments, deployed as part of a complete system for reading digital data stored in DNA.

The features of an embodiment of a complete system are illustrated in FIG. 22. In various aspects, and with reference to FIG. 22, a complete digital data reading system comprises a motherboard with a staging area for an array of multiple chips, in order to provide data reading throughput beyond that of the limitations of a single chip. Such chips are individually housed in flow cells, with a fluidics liquid handling system that controls the additional and removal of the sensor system liquid reagents. In addition, the fluidic system receives DNA encoding data in solution form, originating from a data repository source. The motherboard would also comprise a suitable first stage data processing unit, capable of receiving and reducing raw signal data at very high rates, such as exceeding 1 TB per second, exceeding 10 TB per second, or exceeding 100 TB per second, indicated as a primary signal processor. This primary processor may comprise one, multiple, or combinations of a FPGA, GPU, or DSP device, or a custom signal processing chip, and this may optionally be followed by stages of similar such signal processors, for a processing pipeline. Data output of this primary pipeline is typically transferred to a fast data storage buffer, such as a solid state drive, with data from here undergoing further processing or decoding in a CPU-based sub-system, from which data is buffered into a lower speed mass storage buffer, such as a hard drive or solid state drive or array of such drives. From there it is transferred to an auxiliary data transfer computer sub-system that handles the subsequent transfer of decoded data to a destination. All these system operations are under the high-level control of an auxiliary control computer that monitors, coordinates and controls the interplay of these functional units and processes.

In some embodiments, chips within the reader system may be disposable, and replaced after a certain duty cycle, such as 24 hours to 48 hours. In other embodiments, the chips may be reconditioned in place after such a usage period, whereby the molecular complex, and possibly conjugating groups, are removed, and then replaced with new such components through a serious of chemical solution exposures. The removal process may comprise using voltages applied to the electrodes to drive removal, such as an elevated violated applied to the electrodes, or an alternating voltage applied to the electrodes, or a voltage sweep. The process may also comprise the use chemicals that denature, dissolve or dissociate or otherwise eliminate such groups, such as high molarity urea, or guanidine or other chaotropic salts, proteases such as Proteinase K, acids such as HCl, bases such as KOH or NaOH, or other agents well known in molecular biology and biochemistry for such purposes. This process may also include the use of applied temperature or light to drive the removal, such as elevated temperature or light in conjunction with photo-cleavable groups in the molecular complex or conjugation groups.

FIG. 23 illustrates n embodiment of a cloud based DNA data archival storage system, in which the complete reader system such as outlined in FIG. 22 is deployed in aggregated format to provide the cloud DNA reader server of the overall archival storage and retrieval system. FIG. 23 shows a cloud computing system, with a standard storage format (upper left). Such a standard cloud computing system is provided with DNA archival data storage capability as indicated. Some cloud-based DNA synthesis system can accept binary data from the cloud computer, and produce the physical data encoding DNA molecules. This server stored the output molecules in a DNA data storage archive, lower right, where typically the physical DNA molecules that encode data could be stored in dried or lyophilized format, or in solution, at ambient temperature or cooled or frozen. From this archive, when data is to be retrieved, a DNA sample from the archive is provided to the DNA data reader server, which outputs decoded binary data back to the primary cloud computer system. This DNA data reader server may be powered by a multiplicity of DNA reader chip-based systems of the kind indicated in FIG. 22, in combination with additional computers that perform the final decoding of the DNA derived data back to the original data format of the primary cloud storage system.

FIGS. 24, 25 and 26 illustrate the related use of other single-molecule DNA readers that may support amplification-free reading, and that comprise a polymerase (or other processive enzyme) in the sensor. FIG. 26 illustrates a zero mode wave guide polymerase optical sensor, in cross section.

In various embodiments, a molecular electronics sensor comprises the configuration illustrated in FIG. 24. In this case, fundamental electronic measurements are made by a nanopore ionic current sensor that consists of electrodes on either side of a membrane, a pore localized in the membrane, and an aqueous solution phase residing on both sides of the pore. In this embodiment, the pore regulates the passage of ionic current (indicated by the dashed arrow and the "i"). The pore may comprise a biological protein nanopore, native or mutated, and the membrane may comprise a lipid membrane, or synthetic analogue thereof. The pore may also comprise a solid state pore, with the membrane comprising a thinned membrane composed of a solid material such as SiN or Teflon. The pore may have electrodes of the same polarity, or, as illustrated, opposite polarity. As shown in FIG. 24, the polymerase molecule is further complexed with the pore, as part of a molecular complex involving a small number of molecules embedded through the membrane as part of the pore and to provide a conjugation to the polymerase. As the polymerase processes a DNA template, the ionic current through the pore is modulated by this activity, producing distinguishable signal features that correspond to distinct sequence features. Aside from a different geometry of the nano-electrical measurement, the considerations are otherwise identical to those already reviewed herein. That is, nano-pore current sensor versions of the polymerase-based DNS digital data reader are of similar use herein. In various embodiments, the polymerase is directly and specifically conjugated to the pore, and wherein modified dNTPs are used to produce distinguishable signals from DNA sequence features. For producing signals in a nanopore sensor, such dNTP modifications may comprise groups on the γ-phosphate of the dNTP, which can occlude the pore while the dNTP is undergoing incorporation by the polymerase, thereby resulting in current suppression features. In various embodiments, such modifications comprise extending the tri-phosphate chain to 4, 5, 6 or up to 12 phosphates, and adding terminal phosphate groups, or groups to any of phosphates at position 2 or more, which are removed by polymerase incorporation, such groups including polymers that may occlude the pore by entering pore, such as comprising PEG polymers or DNA polymers. The polymerase conjugation to the pore may comprise any one of possible conjugation chemistries, such as a molecular tether, or Spy-SpyCatcher protein-based conjugation system, or the like.

In various embodiments, a molecular electronic sensor for reading DNA comprises a carbon nanotube. As illustrated in FIG. 25, the bridge molecule comprises a carbon nanotube (represented by the bold horizontal bar in FIG. 25 bridging the gap between positive and negative electrodes). In various aspects, the carbon nanotube bridge comprises a single or multi-walled carbon nanotube, and is conjugated to the polymerase molecule at a specific site using any of many possible conjugation chemistries. Such a conjugation may, for example, comprise a pyrene linker to attach to the nanotube via π-stacking of the pyrene on the nanotube, or may comprise attachment to a defect site residing in the carbon nanotube. In this case, the current passing through a carbon nanotube molecular wire is known to be highly sensitive to other molecules in the surrounding environment. It is further known that current passing through a carbon nanotube is sensitive to the activity of an enzyme molecule properly conjugated to that nanotube, including polymerase enzymes. For this particular embodiment, all the aspects of the present disclosure put forth above apply in this instance, to provide a carbon nanotube based sensor for reading digital data stored in DNA molecules, including the related beneficial aspects, encoding schemes, chip formats, systems and cloud based DNA digital data storage systems.

An alternative sensor that produces optical signals is a Zero Mode Waveguide sensor, such as the sensor illustrated in FIG. 26. Such a sensor may comprise a single polymerase as shown, conjugated to the bottom of the metallic well, in the evanescent zone of the excitation field applied to the thin substrate, in a Total Internal Reflection mode. The polymerase is provided with primed template and dNTPs with dye labels on the cleavable phosphate group. When such a dNTP is incorporated, the dye label is held in the evanescent field, and is stimulated to emit photons of the corresponding dye energy spectrum or color. The result is that, under appropriate conditions, such a sensor may produce distinguishable optical signals as indicated, which can be used to encode digital information into DNA molecules. The distinguishable signals here may be photon emissions of a different energy distribution, or color, or emissions with different distinguishable spectra, or different duration or intensity or shape of the spectra versus time, or any combination of such elements that result in distinguishable features. For this Zero Mode Waveguide sensor embodiment indicated in FIG. 26, all the aspects of the disclosure put forth above in the various embodiments also apply in this instance, to provide a Zero Mode Waveguide-based sensor for reading digital data stored in DNA molecules, and the related beneficial aspects, encoding schemes, chip formats (in this case, optical sensor chips, such as image sensor chips), systems and cloud based DNA digital data storage systems may apply to such a sensor.

Further Embodiments

In various embodiments, an amplification-free DNA archival storage system comprises: (i) an amplification-free subsystem for writing DNA data molecules; (ii) an amplification-free subsystem for managing the DNA data molecules; and (iii) an amplification-free subsystem for reading DNA data molecules.

In various embodiments, a reduced-amplification DNA archival storage system comprises an amplification-free subsystem for writing DNA data molecules.

In various embodiments, a reduced-amplification DNA archival storage system comprises an amplification-free subsystem for managing the DNA data molecules.

In various embodiments, a reduced-amplification DNA archival storage system comprises an amplification-free subsystem for reading the DNA data molecules.

In various embodiments, the amplification-free subsystem for writing DNA data molecules comprises the use of isolated, localized, phosphoramidite synthesis reactions.

In various embodiments, the amplification-free subsystem for managing DNA data molecules comprises the taking of aliquots for copying without amplification.

In various embodiments, the amplification-free subsystem for managing DNA data molecules comprises the use of hybridization for selecting volumes or searching for data, without amplification.

In various embodiments, the amplification-free subsystem for reading DNA data molecules comprises the use of a single molecule DNA sequencing system.

In various embodiments, the amplification-free subsystem for reading DNA data molecules comprises the use of a molecular electronic sensor that performs single molecule analysis of DNA.

In various embodiments, the amplification-free subsystem for reading DNA data molecules comprises the use of a molecular electronic sensor that comprises a polymerase, and performs single molecule analysis of DNA.

In various embodiments, the amplification-free subsystem for reading DNA data molecules comprises the use of a plurality of molecular electronic sensors deployed as a sensor array on a CMOS sensor pixel chip.

In various embodiments, a cloud based DNA data storage information system comprises any of the above amplification-free or reduced amplification subsystems.

In various embodiments, a method for retrieving data in an amplification-free DNA data storage and retrieval system comprises: a. obtaining a sample from the DNA molecular storage archive; and, b. reading the DNA data from the sample with an amplification free reader.

In various embodiments, a method of amplification-free DNA data storage comprises: a. writing DNA data with an amplification-free method; b. manipulating the archive with amplification free methods; and c. reading the DNA data with an amplification-free DNA reader.

In various embodiments, these methods above are performed using cloud-based systems.

In various embodiments, an apparatus for retrieving data in an amplification-free DNA data storage system comprises an amplification-free DNA reader device for reading the data encoded in a DNA molecule.

In various embodiments, an apparatus for amplification-free DNA data storage comprises: a. apparatus for writing DNA data with an amplification-free method; b. apparatus for manipulating the archive with amplification free methods; and c. apparatus for reading the DNA data with an amplification free reader.

Amplification-free DNA information storage methods, apparatus and systems are provided. References to "various embodiments", "one embodiment", "an embodiment", "an example embodiment", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described. After reading the description, it will be apparent to one skilled in the relevant art(s) how to implement the disclosure in alternative embodiments.

Benefits, other advantages, and solutions to problems have been described with regard to specific embodiments. However, the benefits, advantages, solutions to problems, and any elements that may cause any benefit, advantage, or solution to occur or become more pronounced are not to be construed as critical, required, or essential features or elements of the disclosure. The scope of the disclosure is accordingly to be limited by nothing other than the appended claims, in which reference to an element in the singular is not intended to mean "one and only one" unless explicitly so stated, but rather "one or more." Moreover, where a phrase similar to 'at least one of A, B, and C' or 'at least one of A, B, or C' is used in the claims or specification, it is intended that the phrase be interpreted to mean that A alone may be present in an embodiment, B alone may be present in an embodiment, C alone may be present in an embodiment, or that any combination of the elements A, B and C may be present in a single embodiment; for example, A and B, A and C, B and C, or A and B and C.

All structural, chemical, and functional equivalents to the elements of the above-described various embodiments that are known to those of ordinary skill in the art are expressly incorporated herein by reference and are intended to be encompassed by the present claims. Moreover, it is not necessary for a device or method to address each and every problem sought to be solved by the present disclosure, for it to be encompassed by the present claims. Furthermore, no element, component, or method step in the present disclosure is intended to be dedicated to the public regardless of whether the element, component, or method step is explicitly recited in the claims. No claim element is intended to invoke 35 U.S.C. 112(f) unless the element is expressly recited using the phrase "means for." As used herein, the terms "comprises", "comprising", or any other variation thereof, are intended to cover a non-exclusive inclusion, such that a molecule, composition, process, method, or device that comprises a list of elements does not include only those elements but may include other elements not expressly listed or inherent to such molecules, compositions, processes, methods, or devices.

We claim:

1. A method of archiving information, the method comprising:
   converting the information into one or more nucleotides using an encoding scheme, the nucleotides predetermined to generate distinguishable signals relating to the information in a measurable electrical parameter of a molecular electronics sensor, that does not require amplifying DNA molecules prior to analysis;
   assembling the one or more nucleotides into a nucleotide sequence; and
   synthesizing a pool of replicate DNA molecules without amplification of the DNA molecules, wherein each replicate DNA molecule incorporates the nucleotide sequence and a single DNA molecule can be analyzed by the molecular electronics sensor to produce a sequence read or data extraction without amplifying the DNA molecules prior to analysis by the sensor; and
   retrieving the information using the molecular electronics sensor.

2. The method of claim 1, wherein the information comprises a string of binary data.

3. The method of claim 2, wherein the encoding scheme converts one or more 0/1 bits of binary data within the string of binary data into a sequence motif comprising more than one nucleotide.

4. The method of claim 3, wherein the step of converting the information comprises dividing the string of binary data into segments, wherein each segment encodes one sequence motif.

5. The method of claim 4, wherein the binary data bit 0 encodes a homopolymer of A, and the 20 binary data bit 1 encodes a homopolymer of C.

6. The method of claim 1, wherein at least one of the one or more nucleotides comprises a modified nucleotide.

7. The method of claim 1, wherein the one or more nucleotides comprise nucleotides that are resistant to secondary structure formation in the replicate DNA molecules compared to a variant of the same nucleotides.

8. The method of claim 1, wherein the encoding scheme comprises any one or combination of BES1, BES2, BES3, BES4, BES5 and BES6.

9. The method of claim 1, wherein the bridge molecule comprises a double-stranded DNA molecule.

10. A method of archiving information, the method comprising:
converting the information into one or more nucleotides using an encoding scheme, the nucleotides predetermined to generate distinguishable signals relating to the information in a measurable electrical parameter of a molecular electronics sensor;
assembling the one or more nucleotides into a nucleotide sequence; and
synthesizing a pool of replicate DNA molecules without amplification of the DNA molecules, wherein each replicate DNA molecule incorporates the nucleotide sequence
exposing at least one of the replicate DNA molecules to the molecular electronics sensor without prior amplification of the DNA molecules;
generating the distinguishable signals; and
converting the distinguishable signals into the information,
wherein the molecular electronics sensor comprises a pair of spaced-apart electrodes and a molecular sensor complex attached to each electrode to form a sensor circuit, wherein the molecular sensor complex comprises a bridge molecule electrically wired to each electrode in the pair of spaced-apart electrodes and a probe molecule conjugated to the bridge molecule.

11. The method of claim 10, wherein the step of exposing at least one of the replicate DNA molecules to the molecular electronics sensor comprises suspending the pool of DNA molecules in a buffer, taking an aliquot of the buffer, and providing the aliquot to the sensor.

12. The method of claim 11, wherein the buffer solution comprises modified dNTPs.

13. The method of claim 10, wherein the bridge molecule comprises a double-stranded DNA molecule.

14. The method of claim 10, wherein i) the bridge molecule comprises a double-stranded DNA molecule and ii) the probe molecule comprises a polymerase and the measurable electrical parameter of the sensor is modulated by enzymatic activity of the polymerase while processing any one of the replicate DNA molecules.

15. The method of claim 10, wherein the measurable electrical parameter of the sensor comprises a source-drain current between the spaced-apart electrodes and through the molecular sensor complex.

16. The method of claim 10, wherein the probe molecule comprises a polymerase and wherein the measurable electrical parameter of the sensor is modulated by enzymatic activity of the polymerase while processing any one of the replicate DNA molecules.

17. The method of claim 16, wherein the polymerase comprises the Klenow Fragment of *E. coli* Polymerase I, and wherein the bridge molecule comprises a double-stranded DNA molecule.

18. The method of claim 16, wherein the bridge molecule comprises a double-stranded DNA molecule.

19. A method of archiving and retrieving a string of binary data in an amplification-free DNA information storage and retrieval system, the method comprising:
dividing the string of binary data into segments of at least one binary bit;
assigning each segment to a sequence motif, each sequence motif comprising at least two nucleotides, the sequence motifs predetermined to generate distinguishable signals in a measurable electrical parameter of a molecular electronics sensor;
assembling the sequence motifs into a nucleotide sequence;
synthesizing a pool of replicate DNA molecules using an amplification-free DNA writing method on a solid support, each replicate DNA molecule incorporating the nucleotide sequence;
suspending the pool of DNA molecules in a buffer;
taking an aliquot of the buffer;
providing the aliquot to the sensor without prior amplification of the DNA molecules;
generating the distinguishable signals; and
converting the distinguishable signals into the string of binary data,
wherein the sensor comprises a pair of spaced apart electrodes and a molecular sensor complex attached to each electrode to form a molecular electronics circuit, wherein the molecular sensor complex comprises a bridge molecule electrically wired to each electrode in the pair of spaced-apart electrodes and a probe molecule conjugated to the bridge molecule.

20. A method of claim 19, wherein multiple copies of target sequence are co-synthesized to avoid amplification after synthesis.

* * * * *

```
                              SEQUENCE LISTING

<160> NUMBER OF SEQ ID NOS: 10

<210> SEQ ID NO 1
<211> LENGTH: 5
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (1)..(5)
<223> OTHER INFORMATION: Xaa = any amino acid

<400> SEQUENCE: 1

Cys Xaa Pro Xaa Arg
1               5

<210> SEQ ID NO 2
<211> LENGTH: 6
<212> TYPE: PRT
<213> ORGANISM: Artificial Sequence
<220> FEATURE:
<223> OTHER INFORMATION: peptide motif

<400> SEQUENCE: 2

Cys Cys Pro Gly Cys Cys
1               5

<210> SEQ ID NO 3
<211> LENGTH: 16
<212> TYPE: DNA
<213> ORGANISM: Artificial Sequence
<220> FEATURE:
<223> OTHER INFORMATION: encoded DNA molecule

<400> SEQUENCE: 3
ggggcccctt ttgggg                                                     16

<210> SEQ ID NO 4
<211> LENGTH: 21
<212> TYPE: DNA
<213> ORGANISM: Artificial Sequence
<220> FEATURE:
<223> OTHER INFORMATION: encoded DNA molecule

<400> SEQUENCE: 4
aggggacccc attttagggg a                                               21

<210> SEQ ID NO 5
<211> LENGTH: 16
<212> TYPE: DNA
<213> ORGANISM: Artificial Sequence
<220> FEATURE:
<223> OTHER INFORMATION: encoded DNA molecule

<400> SEQUENCE: 5
acgcgctatt ggagtc                                                     16

<210> SEQ ID NO 6
<211> LENGTH: 32
<212> TYPE: DNA
```

```
<213> ORGANISM: Artificial Sequence
<220> FEATURE:
<223> OTHER INFORMATION: encoded DNA molecule

<400> SEQUENCE: 6
aacacaacca acccaacccc cacaaacacc ac                                    32

<210> SEQ ID NO 7
<211> LENGTH: 81
<212> TYPE: DNA
<213> ORGANISM: Artificial Sequence
<220> FEATURE:
<223> OTHER INFORMATION: encoded DNA molecule

<400> SEQUENCE: 7
aaaacccaac ccaaaacccc ccaaaacccc ccccaaaac cccccccc cccaacccca         60 aaaaacccaa cccccaacc c                                                 81

<210> SEQ ID NO 8
<211> LENGTH: 11
<212> TYPE: DNA
<213> ORGANISM: Artificial Sequence
<220> FEATURE:
<223> OTHER INFORMATION: encoded DNA molecule
<220> FEATURE:
<221> NAME/KEY: misc_feature
<222> LOCATION: (1)..(11)
<223> OTHER INFORMATION: n = modified base of base analogues

<400> SEQUENCE: 8
cgtcntngct t                                                           11

<210> SEQ ID NO 9
<211> LENGTH: 15
<212> TYPE: DNA
<213> ORGANISM: Artificial Sequence
<220> FEATURE:
<223> OTHER INFORMATION: encoded DNA molecule

<400> SEQUENCE: 9
aacccaaaac ccccc                                                       15

<210> SEQ ID NO 10
<211> LENGTH: 53
<212> TYPE: DNA
<213> ORGANISM: Artificial Sequence
<220> FEATURE:
<223> OTHER INFORMATION: encoded DNA molecule

<400> SEQUENCE: 10
aaaaaaaaaa aaaaaaaaaa cccaaaaaaa aaaaaaaaaa aaaaaaaaaa aaa             53
```